US 9,683,244 B2

(12) United States Patent
Weaver et al.

(10) Patent No.: US 9,683,244 B2
(45) Date of Patent: Jun. 20, 2017

(54) ALPHAVIRUS COMPOSITIONS AND METHODS OF USE

(71) Applicant: The Board of Regents of the University of Texas System, Austin, TX (US)

(72) Inventors: Scott C. Weaver, Galveston, TX (US); Farooq Nasar, Pearland, TX (US); Rodion V. Gorchakov, Houston, TX (US); Hilda Guzman, Galveston, TX (US); Naomi Forrester, Galveston, TX (US); Gustavo Palacios, New Market, MD (US); Ian W. Lipkin, New York, NY (US); Robert B. Tesh, Galveston, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 467 days.

(21) Appl. No.: 13/923,527

(22) Filed: Jun. 21, 2013

(65) Prior Publication Data
US 2014/0056938 A1  Feb. 27, 2014

Related U.S. Application Data

(63) Continuation-in-part of application No. PCT/US2011/066996, filed on Dec. 22, 2011.

(60) Provisional application No. 61/459,989, filed on Dec. 22, 2010.

(51) Int. Cl.
*C12N 7/00* (2006.01)
*C12N 15/86* (2006.01)

(52) U.S. Cl.
CPC .............. *C12N 15/86* (2013.01); *C12N 7/00* (2013.01); *C12N 2770/36121* (2013.01)

(58) Field of Classification Search
None
See application file for complete search history.

(56) References Cited

U.S. PATENT DOCUMENTS

| 6,592,874 B2 | 7/2003 | Schlesinger et al. ...... 424/218.1 |
| 7,771,979 B2 * | 8/2010 | Polo ..................... C07K 14/005 424/205.1 |
| 2004/0018514 A1 | 1/2004 | Kunst et al. .................. 435/6.11 |
| 2008/0260698 A1 | 10/2008 | Weaver et al. .............. 424/93.6 |

FOREIGN PATENT DOCUMENTS

| WO | WO 98/36779 A2 | 8/1998 |
| WO | WO/98/36889 | 8/1998 |

OTHER PUBLICATIONS

International Preliminary Report on Patentability, PCT/US2011/066996, Jul. 4, 2013.
Fornadel et al., *Vector Borne Zoonotic Dis.* 2011, 11(8):1173-9.
Hahn et al., *Proc Natl Acad Sci USA.* 1988, 85(16):5997-6001.
International Preliminary Report on Patentability in International Application No. PCT/US2011/066996 dated Jul. 4, 2013.
International Search Report and Written Opinion in International Application No. PCT/US2011/066996 dated May 11, 2012.
Muriu et al., *Malar J.* 2008, 7:43.
Weaver et al., *J. Virol.* 1997, 71:613-623.

* cited by examiner

*Primary Examiner* — Michelle S Horning
(74) *Attorney, Agent, or Firm* — Norton Rose Fulbright US LLP

(57) ABSTRACT

Embodiments are directed compositions related to Eilat virus and uses thereof.

8 Claims, 16 Drawing Sheets

| Virus | nsP1 CSE | |
|---|---|---|
| Eilat | CAUGGUCACCCCGAAUGACCACGCCAAUGCGAGACCCUUCUCCCAUUGCGC | SEQ ID NO:7 |
| Trocara | GCA....UG.C........U.....C......G......CUG.. | SEQ ID NO:8 |
| Aura | GCA......U.........U.....C...G......G..CUG.. | SEQ ID NO:9 |
| Whataroa | GCA...C..G..A......U.....C...U......G..CUG.. | SEQ ID NO:10 |
| Sindbis | GCA.....U..A.......U.....C...A..A...U..CUG.. | SEQ ID NO:11 |
| WEE | GCA....UGAC..C.....U.....C......A...U..GUG.. | SEQ ID NO:12 |
| EEE | GCA....UGAC........U.........U..G.G.U..CCUA. | SEQ ID NO:13 |
| VEE | GCA....UGAU........U.........C..G.G.U..CUG.. | SEQ ID NO:14 |
| Chikungunya | GCA.....AU.........U.........C......G..CUA.. | SEQ ID NO:15 |
| Ross River | GCA.....A..U.......U.........C...G..U..CUG.. | SEQ ID NO:16 |
| Una | GCA.....A..........U.........C......G..CCU.. | SEQ ID NO:17 |
| Semliki Forest | GCA.....A..A.......U..G..C......A...U..CCUG. | SEQ ID NO:18 |
| Middelburg | GCA.....A..........U..A......C......G..CCUU. | SEQ ID NO:19 |
| Barmah Forest | GCA.AC..A..A..C...U..AC..C...G..G.G.U..CCUU. | SEQ ID NO:20 |
| Ndumu | GCA.....A..........U.....A......G.G.U..CCUU. | SEQ ID NO:21 |
| SES | GCA.....A..U.......U.........C......U..CUU.. | SEQ ID NO:22 |
| SPD | .AUAGGU.GU.U..C....U..GCC........U.G..C.UG.. | SEQ ID NO:23 |

| Virus | nsP1/nsp2 | nsP2/nsP3 | nsP3/nsP4 | Capsid/E3 | E3/E2 | |
|---|---|---|---|---|---|---|
| Eilat | DIGG/ALVE | GVGA/APSY | GAGG/YIFS | TVEW/SAIV | RARR/AVAP | SEQ ID NO:24, 25, 26, 27, 28 |
| Trocara | ...A/....D | .I.C/..... | .V../..... | ..K./...AT | .PK./STEL | SEQ ID NO:29, 30, 31, 32, 33 |
| Aura | .A.A/..... | .S../..... | .V../..... | ..../.RAI | .HV./STPT | SEQ ID NO:34, 35, 36, 37, 38 |
| Whataroa | ...A/..... | ..../..... | .V../..... | .E../..AA | .HK./SITD | SEQ ID NO:39, 40, 41, 42, 43 |
| Sindbis | ...A/..... | ..../..... | ..../..... | .E../..AP | .SK./S.ID | SEQ ID NO:44, 45, 46, 47, 48 |
| WEE | EA.A/GS.. | EA.R/..A. | E../..A/ | SES./.LVT | .QK./SITD | SEQ ID NO:49, 50, 51, 52, 53 |
| EEE | EA.A/GS.. | EA.R/..A. | E../..A/ | SEP./.LAT | .T../DLDT | SEQ ID NO:54, 55, 56, 57, 58 |
| VEE | EA.A/GS.. | EA.C/..../ | D../..A/ | CEQ./.LVT | .K../STEE | SEQ ID NO:59, 60, 61, 62, 63 |
| Chikungunya | RA.A/GII. | RA.C/..../ | R../..A/ | AE./..LAI | .Q../SIKD | SEQ ID NO:64, 65, 66, 67, 68 |
| Ross River | RA.A/GV.. | TA.C/..../ | R../..A/ | .E../..AL | .H../S.TE | SEQ ID NO:69, 70, 71, 72, 73 |
| Una | RA.A/GV.. | TA.C/..A. | R../..A/ | ..../..PL | .H../S.TQ | SEQ ID NO:74, 75, 76, 77, 78 |
| Semliki Forest | HA.A/GV.. | TA.C/..../ | R../..A/ | SE../..PL | .H../S.SQ | SEQ ID NO:79, 80, 81, 82, 83 |
| Middelburg | RA.A/GV.N | TA.C/..../ | R../..A/ | .E../T.L. | .R../GLTE | SEQ ID NO:84, 85, 86, 87, 88 |
| Barmah Forest | RA.E/GV.. | PA.S/..A. | R../..A/ | S../..AA | .PK./S..H | SEQ ID NO:89, 90, 91, 92, 93 |
| Ndumu | RA.A/GV.. | RA../..A. | R../..A/ | ..../..AA | .H../.AQH | SEQ ID NO:94, 95, 96, 97, 98 |
| SES | RA.A/GV.. | PA.T/..N. | R../..A/ | ..../..LT | .GK./S...S | SEQ ID NO:99, 100, 101, 102, 103 |
| SPD | GA.A/TIID | M.../..G. | .L../..../ | AIP./TRAP | .RK./...ST | SEQ ID NO:104, 105, 106, 107, 108 |

| Virus | subgenomic promoter | |
|---|---|---|
| Eilat | CCCUCUACAACUAACCUAAAUAGU | SEQ ID NO:109 |
| Aura | A.......GGUGGU..........A | SEQ ID NO:110 |
| Whataroa | AG......GG.GGU..........A | SEQ ID NO:111 |
| Sindbis | AU......GGUGGU.......... | SEQ ID NO:112 |
| WEE | ........GG...G.......... | SEQ ID NO:113 |
| EEE | ........GG...G.......... | SEQ ID NO:114 |
| VEE | .U......GG.......G...G.A | SEQ ID NO:115 |
| Chikungunya | .UU.....GG.GGU...G...G.G | SEQ ID NO:116 |
| Ross River | A.......GGUGGU..........A | SEQ ID NO:117 |
| Semliki Forest | A.......GG.GGU....G..U.G | SEQ ID NO:118 |
| Middelburg | A.......GG.GGU.......... | SEQ ID NO:119 |
| Barmah Forest | AU......GGUGGU.......... | SEQ ID NO:120 |
| SES | .G......GG..GU..........A | SEQ ID NO:121 |
| SPD | ........GU.......U....U. | SEQ ID NO:122 |

B)

| Virus | 3' CSE | |
|---|---|---|
| Eilat | AAUUGUUUUUAAUAUUCC | SEQ ID NO:123 |
| Aura | .U................ | SEQ ID NO:124 |
| Sindbis | .U..........C..... | SEQ ID NO:125 |
| WEE | .U...........A.... | SEQ ID NO:126 |
| EEE | .U................ | SEQ ID NO:127 |
| VEE | .U................ | SEQ ID NO:128 |
| Ross River | G...............UAC | SEQ ID NO:129 |
| Semliki Forest | ....G............. | SEQ ID NO:130 |
| Middelburg | CUA...G..........C. | SEQ ID NO:131 |
| Barmah Forest | .U..GU..........UAC | SEQ ID NO:132 |
| SPD | CUA...G.....A....U.AAUAC | SEQ ID NO:133 |

FIGs. 3A-3B

| Virus | E1 fusion peptide | | Ribosomal binding site | |
|---|---|---|---|---|
| Eilat | GVYPFMWGGAQCFCDTEN | SEQ ID NO:135 | KPGKRERTALRLQAD | SEQ ID NO:152 |
| Trocara | .....................ES.. | SEQ ID NO:136 | ...Q.M.MKFE.. | SEQ ID NO:153 |
| Aura | ......L...........S.. | SEQ ID NO:137 | ...Q.....KFE.. | SEQ ID NO:154 |
| Whataroa | ..................S.. | SEQ ID NO:138 | ...Q.MV.K.E.. | SEQ ID NO:155 |
| Sindbis | ..................S.. | SEQ ID NO:139 | ...Q.M...K.E.. | SEQ ID NO:156 |
| WEE | ........Y............ | SEQ ID NO:140 | ...Q.MCMK.ES. | SEQ ID NO:157 |
| EEE | ........Y............ | SEQ ID NO:141 | ...Q.MCMK.ES. | SEQ ID NO:158 |
| VEE | ........Y........S... | SEQ ID NO:142 | ...Q.MVMK.ES. | SEQ ID NO:159 |
| Chikungunya | ........Y........S... | SEQ ID NO:143 | ...R.....MCMKIEN. | SEQ ID NO:160 |
| Ross River | ........Y........S... | SEQ ID NO:144 | ...R.....MCMKIEN. | SEQ ID NO:161 |
| Una | ......L.Y........S... | SEQ ID NO:145 | NL.......MCMKIEN. | SEQ ID NO:162 |
| Semliki Forest | ........Y........S... | SEQ ID NO:146 | .........MCMKIEN. | SEQ ID NO:163 |
| Middelburg | ......L.Y........S... | SEQ ID NO:147 | .........KCMKIEN. | SEQ ID NO:164 |
| Barmah Forest | ........Y........NS.. | SEQ ID NO:148 | ...M.....NCMKIEN. | SEQ ID NO:165 |
| Ndumu | ........Y........SS.. | SEQ ID NO:149 | .........KCMKIES. | SEQ ID NO:166 |
| SES | .....Y..Y........S... | SEQ ID NO:150 | .........ACMKIES. | SEQ ID NO:167 |
| SPD | N...LL..A.H....S... | SEQ ID NO:151 | R...EV.ISVKCARQ | SEQ ID NO:168 |

| MIAF | Eilat Antigen Ht/Ho* |
|---|---|
| Trocara | 8/≥256 |
| Aura | 8/≥256 |
| Sindbis | 16/≥256 |
| Whataroa | <8/16 |
| WEE | <8/≥128 |
| Fort Morgan | <8/≥256 |
| Highlands J | <8/64 |
| EEE | 8/≥256 |
| VEE | 16/≥256 |
| VEE IIIA (Mucambo) | <8/≥256 |
| VEE IV (Pixuna) | <8/≥256 |
| VEE II (Everglades) | <8/≥256 |
| Mayaro | <8/≥256 |
| Una | <8/≥256 |
| Bebaru | <8/≥256 |
| Ross River | <8/≥256 |
| Getah | <8/≥256 |
| Chikungunya | <8/≥256 |
| O'nyong-nyong | <8/≥256 |
| Semliki Forest | <8/≥256 |
| Middelburg | <8/≥256 |
| Ndumu | <8/≥256 |
| Barmah Forest | <8/≥256 |

B)

| Antigen | Eilat Antibody Ht/Ho* |
|---|---|
| Trocara | 20/10240 |
| Sindbis | 40/5120 |
| WEE | 40/2560 |
| EEE | 20/2560 |
| Aura | <20/5120 |
| Mayaro | <20/5120 |
| Una | <20/5120 |
| Getah | <20/10240 |
| Chikungunya | <20/5120 |
| Semliki Forest | <20/2560 |

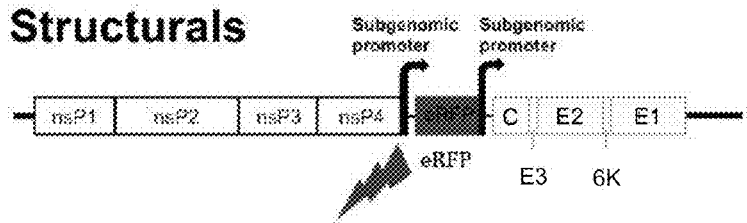
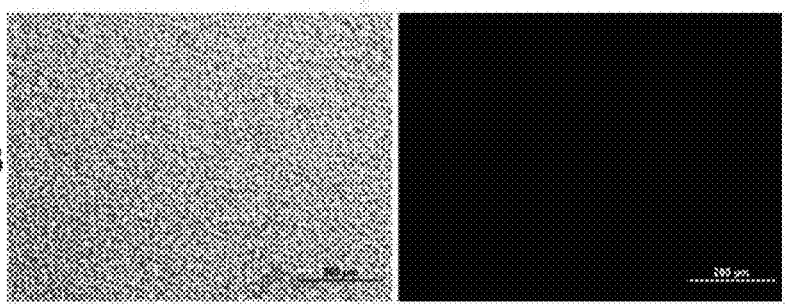
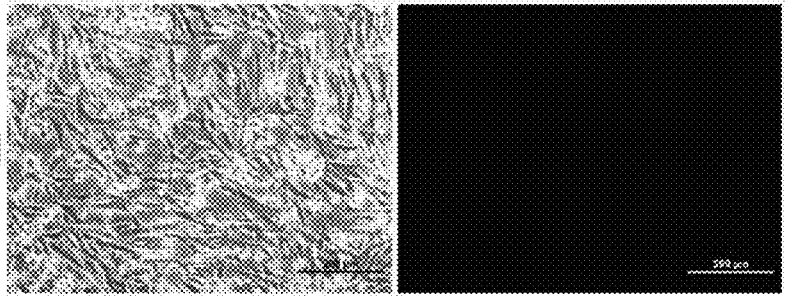
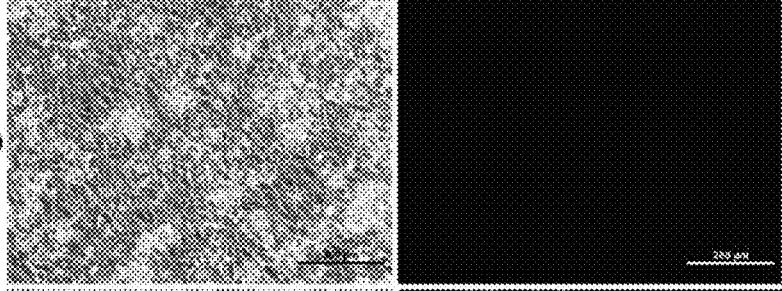
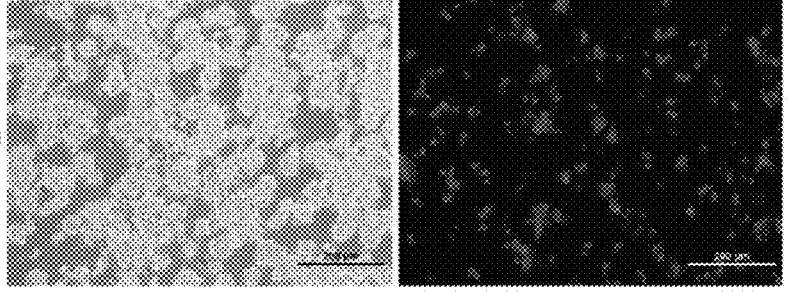
FIGs. 12A-12B

FIGs. 13A-13B

SEQUENCE LISTING

<160> NUMBER OF SEQ ID NOS: 133

<210> SEQ ID NO 1
<211> LENGTH: 11634
<212> TYPE: DNA
<213> ORGANISM: Eilat virus
<220> FEATURE:
<221> NAME/KEY: 5'UTR
<222> LOCATION: (1)..(56)
<220> FEATURE:
<221> NAME/KEY: misc_feature
<222> LOCATION: (57)..(7304)
<223> OTHER INFORMATION: Non-structural protein coding region
<220> FEATURE:
<221> NAME/KEY: misc_feature
<222> LOCATION: (7387)..(11088)
<223> OTHER INFORMATION: Structural protein coding region
<220> FEATURE:
<221> NAME/KEY: 3'UTR
<222> LOCATION: (11089)..(11634)

<400> SEQUENCE: 1
ataggctgca cattacacat tagaaatcgt aacgtagcct tccactttca tcgaacatgg    60
agaaaccaac tgttaacgtc gacgtagacc cccaaagtcc gttcgtactg cagttgcaga   120
aacacttccc ccagtttgag atagtggcta acatggtcac cccgaatgac cacgccaatg   180
cgagagcctt ctcccattgc gccagtaaac tgatcgaagc ggaggtacct gttaccacgc   240
cgatcatcga catagggagc gcacctgctc gtagaatgta ttccgagcac cgctaccact   300
gcgtttgccc tatgaaatgc ccagaagatc cggaccgcct taccacctat gcgaaccgcc   360
ttgtcgaaaa cgccacgaag atcgctaaca aacggctaga cgctaagcta caagacctta   420
agcaagtctt agaaactcct gacatagaaa cggactcgat ctgcttccac gacgacgcta   480
catgccgttg ggtagcggag gtctctgtca tgcaggacgt gtacatagac gcccccagct   540
ctatctacca ccaagcacta aaaggcatcc gcaaaatata ctggattggc ttcgacacca   600
cgccgttcat gttcaaagca ctcgccggat cttacccctc gtacaacacc aactgggccg   660
acgagaaagt actcgaagca cgaaacatcg gcctatgcag taccacactg agcgaaggat   720
cgacagggaa actgtcgatc atgcgaaaga agagattgtt acctggtgct caggtctact   780
tttctgttgg gtcaacactg taccctgaaa accgctccaa tcttatgagt tggcacctcc   840

```
cttccgtgtt ccatctgaag ggtagaaacg cattcacttg ccgctgtgac acagtggtca    900
actgcgacgg ttacgtggtt aagaaaataa ccattagccc caacctcata ggtacaccag    960
caggatacgc ggtgactaac aacagtgagg gattcttact ttgtaaagtc actgacactg    1020
tacgcggcga acgggtttcg ttccccgtgt gcatgagtat accggcaacc atctgcgacc    1080
aaatgactgg catactagcc acagacataa acccggaaga cgcacaaaaa ctgctggttg    1140
ggctcaacca gcgtattgtc gtcaacgaaa agaccaaccg aaacgtcaac acgatgcaga    1200
accatcttct accggcagta gcacaaggat ttagcaaatg ggccaaggaa cgcaaagcag    1260
acggagacga cgagaaacat ctcgggactc gtgaacgctc cttaaccttc ggatgtctct    1320
gggcgtttag gaccaagaaa gtacactcat tctaccgccc acctggtaca cagaccatcg    1380
tcaaggtgga atcagtgttc acagcgtcgc cccttgccat ccccatccgg caaacatctt    1440
tgcctatctc actgcgcctg aagcttaaga tggcgatagc aaagaagcaa aacaacccca    1500
tcgctactat cacacagacg caaattacga acgccatcga attccaaaaa gaagctactg    1560
aaacggcgcg cgcggttgaa ctcaacaatg ctctcccgcc cctgcgtgcc accgaacagg    1620
atccgacacc ttctgtagaa cacgtcgtct gcgaggtaga agaactctcc gacgacatcg    1680
gcggggcgct ggtcgagacc ccacgtggac acgtgcgaat cttaccccag ccaaccgatg    1740
tcaaggtagg gaactacctt gtcatctccc cgcaagctgt gcttcgaaac gataaattaa    1800
gtagactaca ccccctagca gagcaaataa aggtcatcac acacaccggg cgcaagggcc    1860
gatacgaagt ggcgccgtat agcggaaaaa tgctactacc atgcggtacc tccgtcccat    1920
ggcctcagtt ctgcgcactt gctgaaagtg caacccagt gttcaacgaa cgagaaatga    1980
tcgaccgtaa attagcgtat atcgcacagc acggcccagc cttgaacaca gacgaggaac    2040
aatacaaggt tatcaaagca tcagcagcag acagcgaata cgtgttcgac atcgaccgaa    2100
tgaggtgcgt gccgacaaaa gaggcaaacg gtctagtatt ggtaggggaa ctcacacaac    2160
caccctacca cgaactcgct atgcagggtc tatatactag accagccgca ccctatccaa    2220
tagagaccat aggtgtcatc ggcacgccag gctccgggaa atcagcgatc attaagaaca    2280
ccgtcaccac caaagacctc gtcactagtg gcaagaaaga gaactgcaaa gagatagaaa    2340
ctgacgtact ccgccttcgc aacctcgtca ttaagagccg cacggtggac tccgtgctac    2400
tcaacggttg cacccaagag gtagacgttc tacacgtaga cgaggcattc gcgtgtcacg    2460
ccggaacgtt gttagctctc atcgctatcg taaaaccgcg ttgtaaagta gtactgtacg    2520
gagacccgaa acaatgcggc ttcttcaatc tcatgcagat caaagtccat ttcaacaacc    2580
cggaggttga cgtctgctcc caattacact acaagtatat atccaggcgc tgcatcctgc    2640
ctgtcaccgc catcgtatct tccatacatt acgacggcaa aatgcgcaca acgaacaccg    2700
ccgaccaacg tatagagatt gatactacag ggacctcgaa gccgaaaccg accgacctca    2760
tcctcacatg cttccgcgga tgggttaaac agctccaact cgagtatccc cgtaacgaag    2820
taatgaccgc agccgcctct caaggcctga cccgtaaacg tgtatatgct gtccgctaca    2880
aggtcaatga gaacccctc tacgcctta cttcagaaca cgtgaacgtg ctgcttacca    2940
ggacggaaca tacctagta tggaaaacgc tacaaggaga tccatggatc aagcacctgt    3000
ccaatgtacc gaaaggaaac ttctccgcga cggtcgacga atggcacgcc gagcacgaac    3060
gcatcatgaa cgccatccgc atgcccaccc ccgaagtcaa tgccttctct tgtaagacta    3120
acgtatgctg ggcgaaggca cttgtaccgg tcttggcgac cgctggtctg aagctctctg    3180
gcgcccaatg gacagagctg ttcccccaat tcgaaagaga cgaaccgcac tcagctacgt    3240
```

```
ttgctcttga cgtcttatgc ataaagtact tcggaatgga cctcactagc ggcatcttcg   3300
ccaaaccgac agtgcccttg accttccacc cggtaagccg ttatcacccg caagcacact   3360
gggacaacgc caacggagaa caacgctacg gattcgaccc tgacatcgcc aaggcactcg   3420
cacgccgatt cccagtgttc tctcaggccg ctaaaggaca tgccatctca cctatccttg   3480
gtacgacgca cactctttca agccgcgaca actacgtgcc cgtcaaccgt attgtcccgc   3540
acacactgaa aggagagtac acgtatgtca aacaagattc ccttgcatcc gttctctctg   3600
ctgtgcaagc attttcagtc ttagttgtct cgtcagagcc catcgcgagc gccacgaagc   3660
aaatcacttg ggtggccccg ctaggcacag ccggctgcat acacacgcac aggctgccct   3720
ggggcttccc aaaaatgtcg ttacacgatg ccgtggcagt caatatggag accgaatacc   3780
gaggacatca ctaccagcaa tgcgaagatc acgtcgccat cctcaagacc ctgggcaagt   3840
ctgccctcgc caacctaaga cctggcggca ccctgattct gcgcacctac ggttacgcgg   3900
accgcaacag cgagaatgta atcactgcac ttgcccgcaa gttcgcgaga gtaactgcag   3960
tcaggtctag taaccccctca agcaataccg aaatctactt gatcttcagg aaattcgaca   4020
acaaccgatc cagacagttt accttgcatc atcttaaccg cgcgatttcc gcgctctacg   4080
aaagtccatg cgaccccgac ggagtgggcg ccgccccatc atactcggtg atcagaggcg   4140
acataaccgc gactaactcc cacgccattg tcgtccctgt cacgccggag cgaaaagacg   4200
gcgtgtatcg cgcttgtagc aagaaatggg gccccctacc tcgcctggag tggaccgaag   4260
gtgccacctt gttctcgccc ggttcaccag ccactctgca agtatgtgta ccctcgctcc   4320
agaatacgga cactacatca acccagcaag cctaccgcgc catcgccaaa gttgtcgtcg   4380
acgagcagat tccgtcacta tctctacccg tcctcaccat gaagaagacc ggcacagcag   4440
acaccgtatc agaatccttg aaccacctag ttaccgctct ggaccaaacc gatgcaaatg   4500
taactattta ctgtctcgac aaaagcaggc tcataaaaat caaggaagta attgcacgca   4560
aggaagccgt caccgagctt atcgacgacg acctagaaat cgacgaggaa ctgacatggg   4620
tccaccccga tagctgccta cgcaaccgca ccggttttag caccgacaaa ggaaaactgt   4680
actcatatct ggaagggacc aagttccacc agatggccaa ggacttcgca gagattaggt   4740
cactattccc tgacgagatg gaagctaacg aacacatatg ctcactcatc ttaggggaaa   4800
cgatagatgg catccgagaa cgctgtccag tgacagacaa tccgccatca tcaccgccca   4860
agactgtacc ctgcttgtgc atgtacgcca tgaccccaga acgcgcccta cggctcaaga   4920
gcaattctgt cacccaaatc acagtctgct cgtccttcgt tctcaagaag caccacatca   4980
aaggggtaca gaagatccaa tgcacggcac ctatgttatt caacccgaca ccattaactt   5040
ccaggacggt ccgcactccg ccacaagtct cagcacgagc cgcactcgat cttcctcccg   5100
ttgcacctat gccttctgta cctgcaccgg ttagcctgac gcctacgagg cgtgcaccac   5160
caccgcccct taccaaacga cccgttgtcg tacgtccgtc gacgcctcca ccgccgccac   5220
cagtacgcca gacaccaacg ccagtgctcg cgccacggac tggttctacg gcagcaccca   5280
ctccgacgcc acgcctctcg ttatctacgg accagccatc cgtagacatt tcgttcggag   5340
acttttcccc cgcagaaacg atgtctttga tgctgtcgtc ccctggctct gacaccgcca   5400
gtatcacctt cggtgacttc gacgaggacg aggtagaatc tatagtagga cgggaatatt   5460
gactaaccgg agcgggaggg tacatatttt cttcagacac cggcagtggg catttacaac   5520
aacgttcggt ccttcaaaac cgcacgaccg agacaattat agagcgagtc acacatgacc   5580
```

```
gcatccacgc cccacagctc aatgaagcca gggaagaagt tctgaagtta aagtaccaaa   5640
tgtatccctc cgacgctaac aaaagtaggt accgcgcccg caaagtagag aaccaaaaag   5700
ccatatgcat cagccgcctc acggcaggta gccgcagtta ttctttcgga acaacagaag   5760
ccgaatgcta cagagaaact taccctgcag tcatgtactc gtcttcgcta ccatcctcct   5820
actcggcgcc gaccacggct gtggctgtgt gcaacgcgta tctggcagct aattacccca   5880
ccgtcgcctc gtatcagatc actgacgagt acgacgcgta cttagacatg gtcgacggta   5940
ctatggcttg cttagacaca gcgtccttca acccttctaa actaaggagt tttccgaagg   6000
tccacaagta tctggaacct actatccgta gtgcagtacc atctcccttc cagaatacac   6060
tacaaaacgt tctaactgcc gccactaagc gtaactgtaa cgtcacccaa atgcgcgagc   6120
taccgacact cgattctgcc gcatttaacg tagagtgctt taggaaatac gcctgcaaca   6180
acgactactg gcaagaatat gcggataaac ctatccgcat aactacggaa tacgtcaccg   6240
cctacgttgc caagctaaag ggacctaaag ctgccgcctt gttttccaaa acacacgact   6300
taccggcgct cggcgaagta cctatggacc gcttcgtcat ggacatgaag agagacgtta   6360
aagtgacccc tggcagtaag cacaccgaag aacgcccgaa agttcaggta attcaagcag   6420
ctgaacctct ggccactgcc tacttatgcg gcatccatcg tgaactggtc cggcgactca   6480
ctgctgcgct ccttcccaac atccacactc tttttgacat gtccgcagag gacttcgacg   6540
ccacactggc ccaccacttc aaaaagggcg accccgtact ggaaacagac atagcatcct   6600
tcgacaaaag tcaggatgac gccttagcac tcacagggct aatgatcctg gaggacctag   6660
gagtagacca gcccctcatg gacctgatcg aggcagcttt cggagatata accagcacgc   6720
acctacccac cggagcacgt ttccggtttg cgccatgat gaagtctggt atgtttctta   6780
ccctgttcat caacaccgtc cttaacgtgg taatagccag ccgtgtatta gaagacaagt   6840
taacgcactc cgcctgcgcc gcattcatcg gcgacgacaa catcatacac ggagtcatat   6900
ctgaccgtat aatggctgac cgatgcgcta catggatgaa tatggaagtc aaaattatag   6960
acgcggtcat gggagactac cctccctatt tctgtggcgg gttcctcatc atagacagcg   7020
tgaccaacac cgcatgccga gtcgccgacc ccctgaagag actattcaaa cttgggaagc   7080
cgcttaccgc ggacgacgac cacgacgatg accggagaag agccctcgag gatgaaacta   7140
aagcatggtt tcgggtaggg atcagagaag gcatcaccgc cgccgtatca tcaagatacg   7200
aagtcgacaa catactgccc gttctcttag cccttagaac ctttgcttta tctacgcgca   7260
acttctctgc cttacgggga acacttaaga ccctctacaa ctaacctaaa tagtgcgcgt   7320
attatcaata ctactagcac actattaccc gtgtacgtac caacggcact acttgcacaa   7380
gtcaacatgt tccgcaccaa taacaaccgc caacgtcgtc aacagccacg ctcccgcagg   7440
caacgttcac cctcgcggcc cctgcagcgc cgacaagacg atgcactctc caaacaggtc   7500
cgcgccctaa ctaccgcagt tcagaaacta gtggtggcag gaaatcgccg cccaccgcct   7560
tccccccgag ccaaggcgcc tggaccagcc caaccacgac cagctaaagc gcccgtcaaa   7620
actccagcca agagaggacc agcccctaag cgtaaacccg gaaagagaga acgtaccgcg   7680
ctccgcctgc aggcagaccg agtcttcccc gtcgttaatg acaaacaagt cacgtcggc    7740
tatgctgtag cgctggaagg gcgtgtcatg aagcctttgc acgtcaaggg cactattgac   7800
caccctctcc ttgcctcact caagtttacc aaatccacgt ccttcgacat ggagtacgcc   7860
gctctaccaa ccaccatgcg ctctgaagcc tttgcttaca ccagcgagca cccagacggg   7920
ttctacagct gggtccatgg cgccgtacag tgcaccaacg ggcgcttctc catccctaca   7980
```

```
ggggcaggag gccctggcga cagcggcagg ccaatcctcg acaacacagg caaagtcgta    8040
gcccttgtcc ttggaggtgc aaatgaaggc actcgcacgt ctctctcggt agtcacgtgg    8100
aacaagtcag gcaccgcagc caagaccaca cccgacgaca cagtggagtg gtccgccatc    8160
gtgaccgcac tttgcgtact cggcaacgcc tccttcactt gcaccgagcc accgatttgc    8220
ttcgacaccc atccaggaga caccctcggc atgctcgagg acaacgtcga ccaccccatg    8280
tactatgacc ttatgtacgc cgccctacta tgtaaccacc agcaaaaacg agcccgtaga    8340
gccgtcgccc cgaaaccgga cgaatatcgc cttgcgtctc cctacgtggg gcgatgcgca    8400
gcatgctcaa acggcatcac ctgcttcagc cccatcaagc ttgaatccgt atggacaaca    8460
ccacacagct cggtcctaaa aatgcaacta tcggtacttt tcggtataga cgaaacaggc    8520
aaattggaca acacagtcct cagttacatg tccccgacgg agcatacggt gaaaagcatg    8580
ccgatcacgg cactaaccgc atccacaacc ggaccatgta tcatcacggc cacacgaggc    8640
tatttcgcgc tggcacagtg cccaccaggt gacgtgctca ctgtagcaat gggctctcat    8700
cactgctcca ttgagtccga gcacctcaga ccctcagtgg gtcgcgaaga attcgcctct    8760
acaccgctcc acggcgtccg gcgcccgtgc tctacctatg acgccgccaa atacaccagc    8820
acttctgaaa tgaccctcca ccgcgccaaa ccgcaggcct cagactcact cctgtctatc    8880
gtaaacgaca ctgtccaaat caccgtgtcg tccaacctga ccgtcagtta cgagtgcctc    8940
tgcgacggct accactccgg cttcgtacgt gcaacaacac ttatccctgg atgcactaat    9000
accaaccaat gcattgcatc cgtaaacgac aagacgcgct ggtatcccaa cacggacgac    9060
ttcatcagac acaccgacca cagccccaga ggtaaaatca acgttccttt cccgctagag    9120
gcaggtgaat gcctggtccc gctagcccgc tccccagcta tccggtactc ccgaaatgag    9180
gtggagctca cactggtcac gacccgtaag gccctttttgt ccacacggca actcggctcc    9240
gaaccaaacg caacctctga gtggatcaca tcctccactc gtcggacctt ttacttgcct    9300
gccgcagggc tagagttcac ttggggtaac aacgaccccg tccgcgtttg gcctcaagcc    9360
tcagccgacg gggatgcgca cggtctccca cacgaaatcg ttgcgtacta ttacagcagg    9420 tccctctct tcaccatcgt ggccgtcacc cttatctctg caatcgtgct cgcctcgctg    9480
gccttctgtt gctgcaagtg gacctctttc cgatccgcac tccgctcgcc atacgccctg    9540
gcaccgaacg caaccgtacc catgtgtctc acattgctgt gctgcatccg tcaagcaaaa    9600
gcagacacat acttcgacgc cgccagctat ctctggaaca actaccagcc gctattctgg    9660
gcacagttgg cgataccaac cgcctccatt tttgtgctct ttaaatgctg ctcactcgcc    9720 gtggctttt tagctgttgt gggcgcatcg cttcccctag caagcgccca cgaacatgcg    9780
gccaatgttc ccaactctcc actcttgtcg tataaagccg tcgttacacg ccctggatat    9840
acaccccttg ccctagaaat tcgggttttg gaaaaccgta tccaaccgac aacactcacc    9900
cactattaca cttgctccta ccgcaccgta gtcccgtcgc ctacggtcaa atgctgtggt    9960
agtttgcagt gcggttcttc cagtctaccc gattaccgct gcaaggtgtt caccggagta   10020
tacccattta tgtggggagg ggcccagtgt ttctgcgata ctgagaactc ccaaatgagt   10080
gagagttacg tcgacaagga cccgtcctgc cctaccgacc acgcggaagc ggtagccacc   10140
cagaaccccg tggtacgcgc cacactacag atcactatag caacgccac tactcgcacc   10200 gacgtgtacg ttaacggcgt ttcaccgagc tacactaatg gagcgaaagt cattgccggg   10260
ccgctctcct ctgtatggag tcctttcgca gacaaggtgg tcatctacca gaggcgcgtt   10320
```

-continued

```
tacaatcacg cgttccccga atatggtgcc ggcactcctg gcactttcgg cgacctccaa  10380
ctccccagcc ttcgcgccaa ggactttttc gccaacaccg ggctagtcct caatcgaccc  10440
gacacttctt cgctgcacgt gccgtacaca caagtaccga gcgggtttgt cacctggaga  10500
gaccagcact tgcctgatct tcaacaaacc gctccatatg gctgcgccat ttcaagcagt  10560
ccgctgcagg caattaattg ctcgtacggc agtatccctg tgtccatcga cattcccgac  10620
gcctccttca cccgctcctt cgacgcacca tccgtttctt cactgaaatg cactcctatt  10680
gagtgcgtcc actcggccgg gtacggaggc cttctcagac tagactacgt cgccgacaag  10740
gccggcactt gcagtcttca ttcgcacagt gatgccgtcc ttatgaagga ttcactcctc  10800
agcattaacg caacgggatc ctacacaggt cttttctcga cggccagccc ccaagtcaag  10860
ttcaccatca ccctgtgctc ggcggaggtc agctgcgaga ctgcgtgcaa gccaccactc  10920
gaacacgcct catcacaccc gcacctgacg tcacagactt tcgactccgc tatatcaaca  10980
tccgcctgga catggttgct cagcctattc ggagggtcaa tatcacttgt gaccgtaggc  11040
atctttattg cggcagcctt gtacatcgtc aattgcagac gtcgctaaca ttatcactta  11100
agaacccgcc cacatatata gggctacata gttcacggga aagaacaacc ccctaatagt  11160
aacaaaacaa taaaagtaca aaaacaggta tcagcccctt agcgctgcat aatctatagt  11220
tcacgggaaa gaacaaaccc ctaatagtaa caaaactgca aaacacaaaa acaggtatca  11280
gccccttaga gctgcataat cacatagtcc acgggacaga tcaaccccct attagcaaca  11340
aaacacaaaa tcccaaaaac aggtataagt acccttagta cttactagta ctcactctag  11400
ttcacaggga agaacaaccc ctaaatagta actaaacaca aaacccaaaa acaggtatag  11460
gtacccttag tacctccaat ttgcccatcc atcgggcccg ctcaagccga actcacagag  11520
acgtaggccc cgaactccaa ggagacgtag ggataaaagt gctgaactca cagagacgta  11580
agcacaacaa tttgttttta atatttccaa aaaaaaaaaa aaaaaaaaaa aaaa        11634
```

<210> SEQ ID NO 2
<211> LENGTH: 7248
<212> TYPE: DNA
<213> ORGANISM: Eilat virus

<400> SEQUENCE: 2

```
atggagaaac caactgttaa cgtcgacgta gacccccaaa gtccgttcgt actgcagttg     60
cagaaacact tcccccagtt tgagatagtg gctaacatgg tcaccccgaa tgaccacgcc    120
aatgcgagag ccttctccca ttgcgccagt aaactgatcg aagcggaggt acctgttacc    180
acgccgatca tcgacatagg gagcgcacct gctcgtagaa tgtattccga gcaccgctac    240
cactgcgttt gccctatgaa atgcccagaa gatccggacc gccttaccac ctatgcgaac    300
cgccttgtcg aaaacgccac gaagatcgct aacaaacggc tagacgctaa gctacaagac    360
cttaagcaag tcttagaaac tcctgacata gaaacggact cgatctgctt ccacgacgac    420
gctacatgcc gttgggtagc ggaggtctct gtcatgcagg acgtgtacat agacgccccc    480
agctctatct accaccaagc actaaaaggc atccgcaaaa tatactggat tggcttcgac    540
accacgccgt tcatgttcaa agcactcgcc ggatcttacc cctcgtacaa caccaactgg    600
gccgacgaga aagtactcga agcacgaaac atcggcctat gcagtaccac actgagcgaa    660
ggatcgacag ggaaactgtc gatcatgcga aagaagagat tgttacctgg tgctcaggtc    720
tacttttctg ttgggtcaac actgtaccct gaaaaccgct ccaatcttat gagttggcac    780
ctcccttccg tgttccatct gaagggtaga aacgcattca cttgccgctg tgacacagtg    840
```

```
gtcaactgcg acggttacgt ggttaagaaa ataaccatta gccccaacct cataggtaca    900
ccagcaggat acgcggtgac taacaacagt gagggattct tactttgtaa agtcactgac    960
actgtacgcg gcgaacgggt ttcgttcccc gtgtgcatga gtataccggc aaccatctgc   1020
gaccaaatga ctggcatact agccacagac ataaacccgg aagacgcaca aaaactgctg   1080
gttgggctca accagcgtat tgtcgtcaac ggaaagacca accgaaacgt caacacgatg   1140
cagaaccatc ttctaccggc agtagcacaa ggatttagca aatgggccaa ggaacgcaaa   1200
gcagacggag acgacgagaa acatctcggg actcgtgaac gctccttaac cttcggatgt   1260
ctctgggcgt ttaggaccaa gaaagtacac tcattctacc gcccacctgg tacacagacc   1320
atcgtcaagg tggaatcagt gttcacagcg tcgccccttg ccatcccat ccggcaaaca    1380
tctttgccta tctcactgcg cctgaagctt aagatggcga tagcaaagaa gcaaaacaac   1440
cccatcgcta ctatcacaca gacgcaaatt acgaacgcca tcgaattcca aaaagaagct   1500
actgaaacgg cgcgcgcggt tgaactcaac aatgctctcc cgcccctgcg tgccaccgaa   1560
caggatccga caccttctgt agaacacgtc gtctgcgagg tagaagaact ctccgacgac   1620
atcgcgggg cgctggtcga gaccccacgt ggacacgtgc gaatcttacc ccagccaacc    1680
gatgtcaagg tagggaacta ccttgtcatc tccccgcaag ctgtgcttcg aaacgataaa   1740
ttaagtagac tacccccct agcagagcaa ataaaggtca tcacacacac cgggcgcaag    1800
ggccgatacg aagtggcgcc gtatagcgga aaaatgctac taccatgcgg tacctccgtc   1860
ccatggcctc agttctgcgc acttgctgaa agtgcaaccc tagtgttcaa cgaacgagaa   1920
atgatcgacc gtaaattagc gtatatcgca cagcacggcc cagccttgaa cacagacgag   1980
gaacaataca aggttatcaa agcatcagca gcagacagcg aatacgtgtt cgacatcgac   2040
cgaatgaggt gcgtgccgac aaaagaggca aacggtctag tattggtagg ggaactcaca   2100
caaccaccct accacgaact cgctatgcag ggtctatata ctagaccagc cgcaccctat   2160
ccaatagaga ccataggtgt catcggcacg ccaggctccg ggaaatcagc gatcattaag   2220
aacaccgtca ccaccaaaga cctcgtcact agtggcaaga agagaactg caaagagata    2280
gaaactgacg tactccgcct tcgcaacctc gtcattaaga gccgcacggt ggactccgtg   2340
ctactcaacg gttgcacccca agaggtagac gttctacacg tagacgaggc attcgcgtgt   2400
cacgccggaa cgttgttagc tctcatcgct atcgtaaaac gcgttgtaa agtagtactg    2460
tacggagacc cgaaacaatg cggcttcttc aatctcatgc agatcaaagt ccatttcaac   2520
aacccggagg ttgacgtctg ctcccaatta cactacaagt atatatccag gcgctgcatc   2580
ctgcctgtca ccgccatcgt atcttccata cattacgacg gcaaaatgcg cacaacgaac   2640
accgccgacc aacgtataga gattgatact acagggacct cgaagccgaa accgaccgac   2700
ctcatcctca catgcttccg cggatgggtt aaacagctcc aactcgagta tccccgtaac   2760
gaagtaatga ccgcagccgc ctctcaaggc ctgacccgta acgtgtata tgctgtccgc    2820
tacaaggtca atgagaaccc cctctacgcc tttacttcag aacacgtgaa cgtgctgctt   2880
accaggacgg aacatacct agtatggaaa acgctacaag gagatccatg gatcaagcac    2940
ctgtccaatg taccgaaagg aaacttctcc gcgacggtcg acgaatggca cgccgagcac   3000
gaacgcatca tgaacgccat ccgcatgccc accccgaag tcaatgcctt ctcttgtaag    3060
actaacgtat gctgggcgaa ggcacttgta ccggtcttgg cgaccgctgg tctgaagctc   3120
tctggcgccc aatggacaga gctgttcccc caattcgaaa gagacgaacc gcactcagct   3180
```

-continued

```
acgtttgctc ttgacgtctt atgcataaag tacttcggaa tggacctcac tagcggcatc    3240
ttcgccaaac cgacagtgcc cttgaccttc cacccggtaa gccgttatca cccgcaagca    3300
cactgggaca acgccaacgg agaacaacgc tacggattcg accctgacat cgccaaggca    3360
ctcgcacgcc gattcccagt gttctctcag gccgctaaag gacatgccat ctcacctatc    3420
cttggtacga cgcacactct ttcaagccgc gacaactacg tgcccgtcaa ccgtattgtc    3480
ccgcacacac tgaaaggaga gtacacgtat gtcaaacaag attcccttgc atccgttctc    3540
tctgctgtgc aagcattttc agtcttagtt gtctcgtcag agcccatcgc gagcgccacg    3600
aagcaaatca cttgggtggc cccgctaggc acagccggct gcatacacac gcacaggctg    3660
ccctggggct tcccaaaaat gtcgttacac gatgccgtgg cagtcaatat ggagaccgaa    3720
taccgaggac atcactacca gcaatgcgaa gatcacgtcg ccatcctcaa gaccctgggc    3780
aagtctgccc tcgccaacct aagacctggc ggcaccctga ttctgcgcac ctacggttac    3840
gcggaccgca acagcgagaa tgtaatcact gcacttgccc gcaagttcgc gagagtaact    3900
gcagtcaggt ctagtaaccc ctcaagcaat accgaaatct acttgatctt caggaaattc    3960
gacaacaacc gatccagaca gtttaccttg catcatctta accgcgcgat ttccgcgctc    4020
tacgaaagtc catgcgaccc cgacggagtg ggcgccgccc catcatactc ggtgatcaga    4080
ggcgacataa ccgcgactaa ctcccacgcc attgtcgtcc ctgtcacgcc ggagcgaaaa    4140
gacggcgtgt atcgcgcttg tagcaagaaa tggggccccc tacctcgcct ggagtggacc    4200
gaaggtgcca ccttgttctc gcccggttca ccagccactc tgcaagtatg tgtaccctcg    4260
ctccagaata cggacactac atcaacccag caagcctacc cgcgccatcg caaagttgtc    4320
gtcgacgagc agattccgtc actatctcta cccgtcctca ccatgaagaa gaccggcaca    4380
gcagacaccg tatcagaatc cttgaaccac ctagttaccg ctctggacca aaccgatgca    4440
aatgtaacta tttactgtct cgacaaaagc aggctcataa aaatcaagga agtaattgca    4500
cgcaaggaag ccgtcaccga gcttatcgac gacgacctag aaatcgacga ggaactgaca    4560
tgggtccacc ccgatagctg cctacgcaac cgcaccggtt ttagcaccga caaaggaaaa    4620
ctgtactcat atctggaagg gaccaagttc caccagatgg ccaaggactt cgcagagatt    4680
aggtcactat tccctgacga gatggaagct aacgaacaca tatgctcact catcttaggg    4740
gaaacgatag atggcatccg agaacgctgt ccagtgacag acaatccgcc atcatcaccg    4800
cccaagactg taccctgctt gtgcatgtac gccatgaccc cagaacgcgc cctacggctc    4860
aagagcaatt ctgtcaccca aatcacagtc tgctcgtcct tcgttctcaa gaagcaccac    4920
atcaaagggg tacagaagat ccaatgcacg gcacctatgt tattcaaccc gacaccatta    4980
acttccagga cggtccgcac tccgccacaa gtctcagcac gagccgcact cgatcttcct    5040
cccgttgcac ctatgccttc tgtacctgca ccggttagcc tgacgcctac gaggcgtgca    5100
ccaccaccgc cccttaccaa acgacccgtt gtcgtacgtc cgtcgacgcc tccaccgccg    5160
ccaccagtac gccagacacc aacgccagtg ctcgcgccac ggactggttc tacggcagca    5220
cccactccga cgccacgcct ctcgttatct acggaccagc catccgtaga catttcgttc    5280
ggagactttt cccccgcaga aacgatgtct ttgatgctgt cgtcccctgg ctctgacacc    5340
gccagtatca ccttcggtga cttcgacgag gacgaggtag aatctatagt aggacgggaa    5400
tattgactaa ccggagcggg agggtacata ttttcttcag acaccggcag tgggcattta    5460
caacaacgtt cggtccttca aaaccgcacg accgagacaa ttatagagcg agtcacacat    5520
gaccgcatcc acgccccaca gctcaatgaa gccagggaag aagttctgaa gttaaagtac    5580
```

-continued

```
caaatgtatc cctccgacgc taacaaaagt aggtaccgcg cccgcaaagt agagaaccaa    5640
aaagccatat gcatcagccg cctcacggca ggtagccgca gttattcttt cggaacaaca    5700
gaagccgaat gctacagaga aacttaccct gcagtcatgt actcgtcttc gctaccatcc    5760
tcctactcgg cgccgaccac ggctgtggct gtgtgcaacg cgtatctggc agctaattac    5820
cccaccgtcg cctcgtatca gatcactgac gagtacgacg cgtacttaga catggtcgac    5880
ggtactatgg cttgcttaga cacagcgtcc ttcaacccct ctaaactaag gagttttccg    5940
aaggtccaca agtatctgga acctactatc cgtagtgcag taccatctcc cttccagaat    6000
acactacaaa acgttctaac tgccgccact aagcgtaact gtaacgtcac ccaaatgcgc    6060
gagctaccga cactcgattc tgccgcattt aacgtagagt gctttaggaa atacgcctgc    6120
aacaacgact actggcaaga atatgcggat aaacctatcc gcataactac ggaatacgtc    6180
accgcctacg ttgccaagct aaagggacct aaagctgccg ccttgttttc caaaacacac    6240
gacttaccgg cgctcggcga agtacctatg gaccgcttcg tcatggacat gaagagagac    6300
gttaaagtga cccctggcag taagcacacc gaagaacgcc cgaaagttca ggtaattcaa    6360
gcagctgaac ctctggccac tgcctactta tgcggcatcc atcgtgaact ggtccggcga    6420
ctcactgctg cgctccttcc caacatccac actctttttg acatgtccgc agaggacttc    6480
gacgccacac tggcccacca cttcaaaaag ggcgaccccg tactgaaaac agacatagca    6540
tccttcgaca aaagtcagga tgacgcctta gcactcacag ggctaatgat cctggaggac    6600
ctaggagtag accagcccct catggacctg atcgaggcag ctttcggaga tataaccagc    6660
acgcacctac ccaccggagc acgtttccgg tttggcgcca tgatgaagtc tggtatgttt    6720
cttaccctgt tcatcaacac cgtccttaac gtggtaatag ccagccgtgt attagaagac    6780
aagttaacgc actccgcctg cgccgcattc atcggcgacg acaacatcat acacggagtc    6840
atatctgacc gtataatggc tgaccgatgc gctacatgga tgaatatgga agtcaaaatt    6900
atagacgcgg tcatgggaga ctaccctccc tatttctgtg gcgggttcct catcatagac    6960
agcgtgacca acaccgcatg ccgagtcgcc gaccccctga agagactatt caaacttggg    7020
aagccgctta ccgcggacga cgaccacgac gatgaccgga agagccct cgaggatgaa     7080 actaaagcat ggtttcgggt agggatcaga gaaggcatca ccgccgccgt atcatcaaga    7140
tacgaagtcg acaacatact gcccgttctc ttagccctta gaacctttgc tttatctacg    7200
cgcaacttct ctgccttacg gggaacactt aagaccctct acaactaa                7248
```

<210> SEQ ID NO 3
<211> LENGTH: 2414
<212> TYPE: PRT
<213> ORGANISM: Eilat virus

<400> SEQUENCE: 3

Met Glu Lys Pro Thr Val Asn Val Asp Val Asp Pro Gln Ser Pro Phe
1               5                   10                  15

Val Leu Gln Leu Gln Lys His Phe Pro Gln Phe Glu Ile Val Ala Asn
            20                  25                  30

Met Val Thr Pro Asn Asp His Ala Asn Ala Arg Ala Phe Ser His Cys
        35                  40                  45

Ala Ser Lys Leu Ile Glu Ala Glu Val Pro Val Thr Thr Pro Ile Ile
    50                  55                  60

Asp Ile Gly Ser Ala Pro Ala Arg Arg Met Tyr Ser Glu His Arg Tyr
65                  70                  75                  80

```
His Cys Val Cys Pro Met Lys Cys Pro Glu Asp Pro Asp Arg Leu Thr
             85                  90                  95
Thr Tyr Ala Asn Arg Leu Val Glu Asn Ala Thr Lys Ile Ala Asn Lys
            100                 105                 110
Arg Leu Asp Ala Lys Leu Gln Asp Leu Lys Gln Val Leu Glu Thr Pro
            115                 120                 125
Asp Ile Glu Thr Asp Ser Ile Cys Phe His Asp Asp Ala Thr Cys Arg
130                 135                 140
Trp Val Ala Glu Val Ser Val Met Gln Asp Val Tyr Ile Asp Ala Pro
145                 150                 155                 160
Ser Ser Ile Tyr His Gln Ala Leu Lys Gly Ile Arg Lys Ile Tyr Trp
            165                 170                 175
Ile Gly Phe Asp Thr Thr Pro Phe Met Phe Lys Ala Leu Ala Gly Ser
            180                 185                 190
Tyr Pro Ser Tyr Asn Thr Asn Trp Ala Asp Glu Lys Val Leu Glu Ala
            195                 200                 205
Arg Asn Ile Gly Leu Cys Ser Thr Leu Ser Glu Gly Ser Thr Gly
210                 215                 220
Lys Leu Ser Ile Met Arg Lys Arg Leu Leu Pro Gly Ala Gln Val
225                 230                 235                 240
Tyr Phe Ser Val Gly Ser Thr Leu Tyr Pro Glu Asn Arg Ser Asn Leu
            245                 250                 255
Met Ser Trp His Leu Pro Ser Val Phe His Leu Lys Gly Arg Asn Ala
            260                 265                 270
Phe Thr Cys Arg Cys Asp Thr Val Asn Cys Asp Gly Tyr Val Val
            275                 280                 285
Lys Lys Ile Thr Ile Ser Pro Asn Leu Ile Gly Thr Pro Ala Gly Tyr
            290                 295                 300
Ala Val Thr Asn Asn Ser Glu Gly Phe Leu Leu Cys Lys Val Thr Asp
305                 310                 315                 320
Thr Val Arg Gly Glu Arg Val Ser Phe Pro Val Cys Met Ser Ile Pro
            325                 330                 335
Ala Thr Ile Cys Asp Gln Met Thr Gly Ile Leu Ala Thr Asp Ile Asn
            340                 345                 350
Pro Glu Asp Ala Gln Lys Leu Leu Val Gly Leu Asn Gln Arg Ile Val
            355                 360                 365
Val Asn Gly Lys Thr Asn Arg Asn Val Asn Thr Met Gln Asn His Leu
370                 375                 380
Leu Pro Ala Val Ala Gln Gly Phe Ser Lys Trp Ala Lys Glu Arg Lys
385                 390                 395                 400
Ala Asp Gly Asp Asp Glu Lys His Leu Gly Thr Arg Glu Arg Ser Leu
            405                 410                 415
Thr Phe Gly Cys Leu Trp Ala Phe Arg Thr Lys Lys Val His Ser Phe
            420                 425                 430
Tyr Arg Pro Pro Gly Thr Gln Thr Ile Val Lys Val Glu Ser Val Phe
            435                 440                 445
Thr Ala Ser Pro Leu Ala Ile Pro Ile Arg Gln Thr Ser Leu Pro Ile
            450                 455                 460
Ser Leu Arg Leu Lys Leu Lys Met Ala Ile Ala Lys Lys Gln Asn Asn
465                 470                 475                 480
Pro Ile Ala Thr Ile Thr Gln Thr Gln Ile Thr Asn Ala Ile Glu Phe
            485                 490                 495
```

```
Gln Lys Glu Ala Thr Glu Thr Ala Arg Ala Val Glu Leu Asn Asn Ala
                500                 505                 510

Leu Pro Pro Leu Arg Ala Thr Glu Gln Asp Pro Thr Pro Ser Val Glu
            515                 520                 525

His Val Val Cys Glu Val Glu Glu Leu Ser Asp Asp Ile Gly Gly Ala
        530                 535                 540

Leu Val Glu Thr Pro Arg Gly His Val Arg Ile Leu Pro Gln Pro Thr
545                 550                 555                 560

Asp Val Lys Val Gly Asn Tyr Leu Val Ile Ser Pro Gln Ala Val Leu
                565                 570                 575

Arg Asn Asp Lys Leu Ser Arg Leu His Pro Leu Ala Glu Gln Ile Lys
            580                 585                 590

Val Ile Thr His Thr Gly Arg Lys Gly Arg Tyr Glu Val Ala Pro Tyr
        595                 600                 605

Ser Gly Lys Met Leu Leu Pro Cys Gly Thr Ser Val Pro Trp Pro Gln
        610                 615                 620

Phe Cys Ala Leu Ala Glu Ser Ala Thr Leu Val Phe Asn Glu Arg Glu
625                 630                 635                 640

Met Ile Asp Arg Lys Leu Ala Tyr Ile Ala Gln His Gly Pro Ala Leu
                645                 650                 655

Asn Thr Asp Glu Glu Gln Tyr Lys Val Ile Lys Ala Ser Ala Ala Asp
            660                 665                 670

Ser Glu Tyr Val Phe Asp Ile Asp Arg Met Arg Cys Val Pro Thr Lys
        675                 680                 685

Glu Ala Asn Gly Leu Val Leu Val Gly Glu Leu Thr Gln Pro Pro Tyr
        690                 695                 700

His Glu Leu Ala Met Gln Gly Leu Tyr Thr Arg Pro Ala Ala Pro Tyr
705                 710                 715                 720

Pro Ile Glu Thr Ile Gly Val Ile Gly Thr Pro Gly Ser Gly Lys Ser
                725                 730                 735

Ala Ile Ile Lys Asn Thr Val Thr Thr Lys Asp Leu Val Thr Ser Gly
            740                 745                 750

Lys Lys Glu Asn Cys Lys Glu Ile Glu Thr Asp Val Leu Arg Leu Arg
        755                 760                 765

Asn Leu Val Ile Lys Ser Arg Thr Val Asp Ser Val Leu Leu Asn Gly
        770                 775                 780

Cys Thr Gln Glu Val Asp Val Leu His Val Asp Glu Ala Phe Ala Cys
785                 790                 795                 800

His Ala Gly Thr Leu Leu Ala Leu Ile Ala Ile Val Lys Pro Arg Cys
                805                 810                 815

Lys Val Val Leu Tyr Gly Asp Pro Lys Gln Cys Gly Phe Phe Asn Leu
            820                 825                 830

Met Gln Ile Lys Val His Phe Asn Asn Pro Glu Val Asp Val Cys Ser
        835                 840                 845

Gln Leu His Tyr Lys Tyr Ile Ser Arg Arg Cys Ile Leu Pro Val Thr
        850                 855                 860

Ala Ile Val Ser Ser Ile His Tyr Asp Gly Lys Met Arg Thr Thr Asn
865                 870                 875                 880

Thr Ala Asp Gln Arg Ile Glu Ile Asp Thr Thr Gly Thr Ser Lys Pro
                885                 890                 895

Lys Pro Thr Asp Leu Ile Leu Thr Cys Phe Arg Gly Trp Val Lys Gln
            900                 905                 910

Leu Gln Leu Glu Tyr Pro Arg Asn Glu Val Met Thr Ala Ala Ala Ser
```

```
                915                 920                 925
Gln Gly Leu Thr Arg Lys Arg Val Tyr Ala Val Arg Tyr Lys Val Asn
    930                 935                 940
Glu Asn Pro Leu Tyr Ala Phe Thr Ser Glu His Val Asn Val Leu Leu
945                 950                 955                 960
Thr Arg Thr Glu His Thr Leu Val Trp Lys Thr Leu Gln Gly Asp Pro
                965                 970                 975
Trp Ile Lys His Leu Ser Asn Val Pro Lys Gly Asn Phe Ser Ala Thr
            980                 985                 990
Val Asp Glu Trp His Ala Glu His Glu Arg Ile Met Asn Ala Ile Arg
        995                 1000                1005
Met Pro Thr Pro Glu Val Asn Ala Phe Ser Cys Lys Thr Asn Val
    1010                1015                1020
Cys Trp Ala Lys Ala Leu Val Pro Val Leu Ala Thr Ala Gly Leu
    1025                1030                1035
Lys Leu Ser Gly Ala Gln Trp Thr Glu Leu Phe Pro Gln Phe Glu
    1040                1045                1050
Arg Asp Glu Pro His Ser Ala Thr Phe Ala Leu Asp Val Leu Cys
    1055                1060                1065
Ile Lys Tyr Phe Gly Met Asp Leu Thr Ser Gly Ile Phe Ala Lys
    1070                1075                1080
Pro Thr Val Pro Leu Thr Phe His Pro Val Ser Arg Tyr His Pro
    1085                1090                1095
Gln Ala His Trp Asp Asn Ala Asn Gly Glu Gln Arg Tyr Gly Phe
    1100                1105                1110
Asp Pro Asp Ile Ala Lys Ala Leu Ala Arg Arg Phe Pro Val Phe
    1115                1120                1125
Ser Gln Ala Ala Lys Gly His Ala Ile Ser Pro Ile Leu Gly Thr
    1130                1135                1140
Thr His Thr Leu Ser Ser Arg Asp Asn Tyr Val Pro Val Asn Arg
    1145                1150                1155
Ile Val Pro His Thr Leu Lys Gly Glu Tyr Thr Tyr Val Lys Gln
    1160                1165                1170
Asp Ser Leu Ala Ser Val Leu Ser Ala Val Gln Ala Phe Ser Val
    1175                1180                1185
Leu Val Val Ser Ser Glu Pro Ile Ala Ser Ala Thr Lys Gln Ile
    1190                1195                1200
Thr Trp Val Ala Pro Leu Gly Thr Ala Gly Cys Ile His Thr His
    1205                1210                1215
Arg Leu Pro Trp Gly Phe Pro Lys Met Ser Leu His Asp Ala Val
    1220                1225                1230
Ala Val Asn Met Glu Thr Glu Tyr Arg Gly His His Tyr Gln Gln
    1235                1240                1245
Cys Glu Asp His Val Ala Ile Leu Lys Thr Leu Gly Lys Ser Ala
    1250                1255                1260
Leu Ala Asn Leu Arg Pro Gly Gly Thr Leu Ile Leu Arg Thr Tyr
    1265                1270                1275
Gly Tyr Ala Asp Arg Asn Ser Glu Asn Val Ile Thr Ala Leu Ala
    1280                1285                1290
Arg Lys Phe Ala Arg Val Thr Ala Val Arg Ser Ser Asn Pro Ser
    1295                1300                1305
Ser Asn Thr Glu Ile Tyr Leu Ile Phe Arg Lys Phe Asp Asn Asn
    1310                1315                1320
```

-continued

```
Arg Ser Arg Gln Phe Thr Leu His His Leu Asn Arg Ala Ile Ser
1325                1330                1335

Ala Leu Tyr Glu Ser Pro Cys Asp Pro Asp Gly Val Gly Ala Ala
1340                1345                1350

Pro Ser Tyr Ser Val Ile Arg Gly Asp Ile Thr Ala Thr Asn Ser
1355                1360                1365

His Ala Ile Val Val Pro Val Thr Pro Glu Arg Lys Asp Gly Val
1370                1375                1380

Tyr Arg Ala Cys Ser Lys Lys Trp Gly Pro Leu Pro Arg Leu Glu
1385                1390                1395

Trp Thr Glu Gly Ala Thr Leu Phe Ser Pro Gly Ser Pro Ala Thr
1400                1405                1410

Leu Gln Val Cys Val Pro Ser Leu Gln Asn Thr Asp Thr Thr Ser
1415                1420                1425

Thr Gln Gln Ala Tyr Arg Ala Ile Ala Lys Val Val Val Asp Glu
1430                1435                1440

Gln Ile Pro Ser Leu Ser Leu Pro Val Leu Thr Met Lys Lys Thr
1445                1450                1455

Gly Thr Ala Asp Thr Val Ser Glu Ser Leu Asn His Leu Val Thr
1460                1465                1470

Ala Leu Asp Gln Thr Asp Ala Asn Val Thr Ile Tyr Cys Leu Asp
1475                1480                1485

Lys Ser Arg Leu Ile Lys Ile Lys Glu Val Ile Ala Arg Lys Glu
1490                1495                1500

Ala Val Thr Glu Leu Ile Asp Asp Asp Leu Glu Ile Asp Glu Glu
1505                1510                1515

Leu Thr Trp Val His Pro Asp Ser Cys Leu Arg Asn Arg Thr Gly
1520                1525                1530

Phe Ser Thr Asp Lys Gly Lys Leu Tyr Ser Tyr Leu Glu Gly Thr
1535                1540                1545

Lys Phe His Gln Met Ala Lys Asp Phe Ala Glu Ile Arg Ser Leu
1550                1555                1560

Phe Pro Asp Glu Met Glu Ala Asn Glu His Ile Cys Ser Leu Ile
1565                1570                1575

Leu Gly Glu Thr Ile Asp Gly Ile Arg Glu Arg Cys Pro Val Thr
1580                1585                1590

Asp Asn Pro Pro Ser Ser Pro Pro Lys Thr Val Pro Cys Leu Cys
1595                1600                1605

Met Tyr Ala Met Thr Pro Glu Arg Ala Leu Arg Leu Lys Ser Asn
1610                1615                1620

Ser Val Thr Gln Ile Thr Val Cys Ser Ser Phe Val Leu Lys Lys
1625                1630                1635

His His Ile Lys Gly Val Gln Lys Ile Gln Cys Thr Ala Pro Met
1640                1645                1650

Leu Phe Asn Pro Thr Pro Leu Thr Ser Arg Thr Val Arg Thr Pro
1655                1660                1665

Pro Gln Val Ser Ala Arg Ala Ala Leu Asp Leu Pro Pro Val Ala
1670                1675                1680

Pro Met Pro Ser Val Pro Ala Pro Val Ser Leu Thr Pro Thr Arg
1685                1690                1695

Arg Ala Pro Pro Pro Pro Leu Thr Lys Arg Pro Val Val Val Arg
1700                1705                1710
```

-continued

| | | | | | | | | | | | |
|---|---|---|---|---|---|---|---|---|---|---|---|
| Pro | Ser | Thr | Pro | Pro | Pro | Pro | Pro | Val | Arg | Gln | Thr | Pro | Thr |
| 1715 | | | | 1720 | | | | | 1725 | | | |

| Pro | Val | Leu | Ala | Pro | Arg | Thr | Gly | Ser | Thr | Ala | Ala | Pro | Thr | Pro |
| 1730 | | | | | 1735 | | | | | 1740 | | | |

| Thr | Pro | Arg | Leu | Ser | Leu | Ser | Thr | Asp | Gln | Pro | Ser | Val | Asp | Ile |
| 1745 | | | | | 1750 | | | | | 1755 | | | |

| Ser | Phe | Gly | Asp | Phe | Ser | Pro | Ala | Glu | Thr | Met | Ser | Leu | Met | Leu |
| 1760 | | | | | 1765 | | | | | 1770 | | | |

| Ser | Ser | Pro | Gly | Ser | Asp | Thr | Ala | Ser | Ile | Thr | Phe | Gly | Asp | Phe |
| 1775 | | | | | 1780 | | | | | 1785 | | | |

| Asp | Glu | Asp | Glu | Val | Glu | Ser | Ile | Val | Gly | Arg | Glu | Tyr | Leu | Thr |
| 1790 | | | | | 1795 | | | | | 1800 | | | |

| Gly | Ala | Gly | Gly | Tyr | Ile | Phe | Ser | Ser | Asp | Thr | Gly | Ser | Gly | His |
| 1805 | | | | | 1810 | | | | | 1815 | | | |

| Leu | Gln | Gln | Arg | Ser | Val | Leu | Gln | Asn | Arg | Thr | Glu | Thr | Ile |
| 1820 | | | | | 1825 | | | | | 1830 | | | |

| Ile | Glu | Arg | Val | Thr | His | Asp | Arg | Ile | His | Ala | Pro | Gln | Leu | Asn |
| 1835 | | | | | 1840 | | | | | 1845 | | | |

| Glu | Ala | Arg | Glu | Glu | Val | Leu | Lys | Leu | Lys | Tyr | Gln | Met | Tyr | Pro |
| 1850 | | | | | 1855 | | | | | 1860 | | | |

| Ser | Asp | Ala | Asn | Lys | Ser | Arg | Tyr | Arg | Ala | Arg | Lys | Val | Glu | Asn |
| 1865 | | | | | 1870 | | | | | 1875 | | | |

| Gln | Lys | Ala | Ile | Cys | Ile | Ser | Arg | Leu | Thr | Ala | Gly | Ser | Arg | Ser |
| 1880 | | | | | 1885 | | | | | 1890 | | | |

| Tyr | Ser | Phe | Gly | Thr | Thr | Glu | Ala | Glu | Cys | Tyr | Arg | Glu | Thr | Tyr |
| 1895 | | | | | 1900 | | | | | 1905 | | | |

| Pro | Ala | Val | Met | Tyr | Ser | Ser | Leu | Pro | Ser | Ser | Tyr | Ser | Ala |
| 1910 | | | | | 1915 | | | | | 1920 | | | |

| Pro | Thr | Thr | Ala | Val | Ala | Val | Cys | Asn | Ala | Tyr | Leu | Ala | Ala | Asn |
| 1925 | | | | | 1930 | | | | | 1935 | | | |

| Tyr | Pro | Thr | Val | Ala | Ser | Tyr | Gln | Ile | Thr | Asp | Glu | Tyr | Asp | Ala |
| 1940 | | | | | 1945 | | | | | 1950 | | | |

| Tyr | Leu | Asp | Met | Val | Asp | Gly | Thr | Met | Ala | Cys | Leu | Asp | Thr | Ala |
| 1955 | | | | | 1960 | | | | | 1965 | | | |

| Ser | Phe | Asn | Pro | Ser | Lys | Leu | Arg | Ser | Phe | Pro | Lys | Val | His | Lys |
| 1970 | | | | | 1975 | | | | | 1980 | | | |

| Tyr | Leu | Glu | Pro | Thr | Ile | Arg | Ser | Ala | Val | Pro | Ser | Pro | Phe | Gln |
| 1985 | | | | | 1990 | | | | | 1995 | | | |

| Asn | Thr | Leu | Gln | Asn | Val | Leu | Thr | Ala | Ala | Thr | Lys | Arg | Asn | Cys |
| 2000 | | | | | 2005 | | | | | 2010 | | | |

| Asn | Val | Thr | Gln | Met | Arg | Glu | Leu | Pro | Thr | Leu | Asp | Ser | Ala | Ala |
| 2015 | | | | | 2020 | | | | | 2025 | | | |

| Phe | Asn | Val | Glu | Cys | Phe | Arg | Lys | Tyr | Ala | Cys | Asn | Asn | Asp | Tyr |
| 2030 | | | | | 2035 | | | | | 2040 | | | |

| Trp | Gln | Glu | Tyr | Ala | Asp | Lys | Pro | Ile | Arg | Ile | Thr | Thr | Glu | Tyr |
| 2045 | | | | | 2050 | | | | | 2055 | | | |

| Val | Thr | Ala | Tyr | Val | Ala | Lys | Leu | Lys | Gly | Pro | Lys | Ala | Ala | Ala |
| 2060 | | | | | 2065 | | | | | 2070 | | | |

| Leu | Phe | Ser | Lys | Thr | His | Asp | Leu | Pro | Ala | Leu | Gly | Glu | Val | Pro |
| 2075 | | | | | 2080 | | | | | 2085 | | | |

| Met | Asp | Arg | Phe | Val | Met | Asp | Met | Lys | Arg | Asp | Val | Lys | Val | Thr |
| 2090 | | | | | 2095 | | | | | 2100 | | | |

| Pro | Gly | Ser | Lys | His | Thr | Glu | Glu | Arg | Pro | Lys | Val | Gln | Val | Ile |

-continued

```
    2105                2110                2115

Gln Ala  Ala Glu Pro Leu Ala  Thr Ala Tyr Leu Cys  Gly Ile His
    2120                2125                2130

Arg Glu  Leu Val Arg Arg Leu  Thr Ala Ala Leu Leu  Pro Asn Ile
    2135                2140                2145

His Thr  Leu Phe Asp Met Ser  Ala Glu Asp Phe Asp  Ala Thr Leu
    2150                2155                2160

Ala His  His Phe Lys Lys Gly  Asp Pro Val Leu Glu  Thr Asp Ile
    2165                2170                2175

Ala Ser  Phe Asp Lys Ser Gln  Asp Asp Ala Leu Ala  Leu Thr Gly
    2180                2185                2190

Leu Met  Ile Leu Glu Asp Leu  Gly Val Asp Gln Pro  Leu Met Asp
    2195                2200                2205

Leu Ile  Glu Ala Ala Phe Gly  Asp Ile Thr Ser Thr  His Leu Pro
    2210                2215                2220

Thr Gly  Ala Arg Phe Arg Phe  Gly Ala Met Met Lys  Ser Gly Met
    2225                2230                2235

Phe Leu  Thr Leu Phe Ile Asn  Thr Val Leu Asn Val  Val Ile Ala
    2240                2245                2250

Ser Arg  Val Leu Glu Asp Lys  Leu Thr His Ser Ala  Cys Ala Ala
    2255                2260                2265

Phe Ile  Gly Asp Asp Asn Ile  Ile His Gly Val Ile  Ser Asp Arg
    2270                2275                2280

Ile Met  Ala Asp Arg Cys Ala  Thr Trp Met Asn Met  Glu Val Lys
    2285                2290                2295

Ile Ile  Asp Ala Val Met Gly  Asp Tyr Pro Pro Tyr  Phe Cys Gly
    2300                2305                2310

Gly Phe  Leu Ile Ile Asp Ser  Val Thr Asn Thr Ala  Cys Arg Val
    2315                2320                2325

Ala Asp  Pro Leu Lys Arg Leu  Phe Lys Leu Gly Lys  Pro Leu Thr
    2330                2335                2340

Ala Asp  Asp Asp His Asp Asp  Asp Arg Arg Arg Ala  Leu Glu Asp
    2345                2350                2355

Glu Thr  Lys Ala Trp Phe Arg  Val Gly Ile Arg Glu  Gly Ile Thr
    2360                2365                2370

Ala Ala  Val Ser Ser Arg Tyr  Glu Val Asp Asn Ile  Leu Pro Val
    2375                2380                2385

Leu Leu  Ala Leu Arg Thr Phe  Ala Leu Ser Thr Arg  Asn Phe Ser
    2390                2395                2400

Ala Leu  Arg Gly Thr Leu Lys  Thr Leu Tyr Asn
    2405                2410

<210> SEQ ID NO 4
<211> LENGTH: 3702
<212> TYPE: DNA
<213> ORGANISM: Eilat virus

<400> SEQUENCE: 4
atgttccgca ccaataacaa ccgccaacgt cgtcaacagc cacgctcccg caggcaacgt     60
tcaccctcgc ggcccctgca gcgccgacaa gacgatgcac tctccaaaca ggtccgcgcc    120
ctaactaccg cagttcagaa actagtggtg gcaggaaatc gccgcccacc gccttccccc    180
cgagccaagg cgcctggacc agcccaacca cgaccagcta aagcgcccgt caaaactcca    240
gccaagagag gaccagcccc taagcgtaaa cccggaaaga gagaacgtac cgcgctccgc    300
```

```
ctgcaggcag accgagtctt ccccgtcgtt aatgacaaac aagtcacggt cggctatgct    360
gtagcgctgg aagggcgtgt catgaagcct ttgcacgtca agggcactat tgaccaccct    420
ctccttgcct cactcaagtt taccaaatcc acgtccttcg acatggagta cgccgctcta    480
ccaaccacca tgcgctctga agcctttgct tacaccagcg agcacccaga cgggttctac    540
agctgggtcc atggcgccgt acagtgcacc aacgggcgct tctccatccc tacaggggca    600
ggaggccctg cgacagcggc aggccaatc ctcgacaaca caggcaaagt cgtagccctt    660
gtccttggag gtgcaaatga aggcactcgc acgtctctct cggtagtcac gtggaacaag    720
tcaggcaccg cagccaagac cacacccgac gacacagtgg agtggtccgc catcgtgacc    780
gcactttgcg tactcggcaa cgcctccttc acttgcaccg agccaccgat ttgcttcgac    840
acccatccag gagacaccct cggcatgctc gaggacaacg tcgaccaccc catgtactat    900
gaccttatgt acgccgccct actatgtaac caccagcaaa aacgagcccg tagagccgtc    960
gccccgaaac cggacgaata tcgccttgcg tctccctacg tggggcgatg cgcagcatgc   1020
tcaaacggca tcacctgctt cagccccatc aagcttgaat ccgtatggac aacaccacac   1080
agctcggtcc taaaaatgca actatcggta cttttcggta tagacgaaac aggcaaattg   1140
gacaacacag tcctcagtta catgtccccg acggagcata cggtgaaaag catgccgatc   1200
acggcactaa ccgcatccac aaccggacca tgtatcatca cggccacacg aggctatttc   1260
gcgctggcac agtgcccacc aggtgacgtg ctcactgtag caatgggctc tcatcactgc   1320
tccattgagt ccgagcacct cagaccctca gtgggtcgcg aagaattcgc ctctacaccg   1380
ctccacggcg tccggcgccc gtgctctacc tatgacgccg ccaaatacac cagcacttct   1440
gaaatgaccc tccaccgcgc caaaccgcag gcctcagact cactcctgtc tatcgtaaac   1500
gacactgtcc aaatcaccgt gtcgtccaac ctgaccgtca gttacgagtg cctctgcgac   1560
ggctaccact ccggcttcgt acgtgcaaca acacttatcc ctggatgcac taataccaac   1620
caatgcattg catccgtaaa cgacaagacg cgctggtatc ccaacacgga cgacttcatc   1680
agacacaccg accacagccc cagaggtaaa atcaacgttc cttccccgct agaggcaggt   1740
gaatgcctgg tcccgctagc ccgctcccca gctatccggt actccgaaa tgaggtggag   1800
ctcacactgg tcacgacccg taaggcccctt ttgtccacac ggcaactcgg ctccgaacca   1860
aacgcaacct ctgagtggat cacatcctcc actcgtcgga ccttttactt gcctgccgca   1920
gggctagagt tcacttgggg taacaacgac cccgtccgcg tttggcctca agcctcagcc   1980
gacggggatg cgcacggtct cccacacgaa atcgttgcgt actattacag caggtcccct   2040
ctcttcacca tcgtggccgt caccttatc tctgcaatcg tgctcgcctc gctggccttc   2100
tgttgctgca agtggaccte tttccgatcc gcactccgct cgccatacgc cctggcaccg   2160
aacgcaaccg tacccatgtg tctcacattg ctgtgctgca tccgtcaagc aaaagcagac   2220
acatacttcg acgccgccag ctatctctgg aacaactacc agccgctatt ctgggcacag   2280
ttggcgatac caaccgcctc cattttgtg ctctttaaat gctgctcact cgccgtggct   2340
tttttagctg ttgtgggcgc atcgcttccc ctagcaagcg cccacgaaca tgcggccaat   2400
gttcccaact ctccactctt gtcgtataaa gccgtcgtta cacgccctgg atatacccc    2460
cttgccctag aaattcgggt tttggaaaac cgtatccaac cgacaacact cacccactat   2520
tacacttgct cctaccgcac cgtagtcccg tcgcctacgg tcaaatgctg tggtagttg    2580
cagtgcggtt cttccagtct acccgattac cgctgcaagg tgttcaccgg agtataccca   2640
```

-continued

```
tttatgtggg gaggggccca gtgtttctgc gatactgaga actcccaaat gagtgagagt    2700
tacgtcgaca aggacccgtc ctgccctacc gaccacgcgg aagcggtagc cacccagaac    2760
cccgtggtac gcgccacact acagatcact ataggcaacg ccactactcg caccgacgtg    2820
tacgttaacg gcgtttcacc gagctacact aatggagcga aagtcattgc cgggccgctc    2880
tcctctgtat ggagtccttt cgcagacaag gtggtcatct accagaggcg cgtttacaat    2940
cacgcgttcc ccgaatatgg tgccggcact cctggcactt cggcgacct ccaactcccc     3000 agccttcgcg ccaaggactt tttcgccaac accgggctag tcctcaatcg acccgacact    3060
tcttcgctgc acgtgccgta cacacaagta ccgagcgggt ttgtcacctg gagagaccag    3120
cacttgcctg atcttcaaca aaccgctcca tatggctgcg ccatttcaag cagtccgctg    3180
caggcaatta attgctcgta cggcagtatc cctgtgtcca tcgacattcc cgacgcctcc    3240
ttcacccgct ccttcgacgc accatccgtt tcttcactga aatgcactcc tattgagtgc    3300
gtccactcgg ccgggtacgg aggccttctc agactagact acgtcgccga caaggccggc    3360
acttgcagtc ttcattcgca cagtgatgcc gtccttatga aggattcact cctcagcatt    3420
aacgcaacgg gatcctacac aggtctttc tcgacggcca gccccaagt caagttcacc      3480 atcaccctgt gctcggcgga ggtcagctgc gagactgcgc gcaagccacc actcgaacac    3540
gcctcatcac acccgcacct gacgtcacag actttcgact ccgctatatc aacatccgcc    3600
tggacatggt tgctcagcct attcggaggg tcaatatcac ttgtgaccgt aggcatcttt    3660
attgcggcag ccttgtacat cgtcaattgc agacgtcgct aa                      3702
```

```
<210> SEQ ID NO 5
<211> LENGTH: 1233
<212> TYPE: PRT
<213> ORGANISM: Eilat virus

<400> SEQUENCE: 5

Met Phe Arg Thr Asn Asn Asn Arg Gln Arg Arg Gln Gln Pro Arg Ser
1               5                   10                  15

Arg Arg Gln Arg Ser Pro Ser Arg Pro Leu Gln Arg Arg Gln Asp Asp
                20                  25                  30

Ala Leu Ser Lys Gln Val Arg Ala Leu Thr Thr Ala Val Gln Lys Leu
            35                  40                  45

Val Val Ala Gly Asn Arg Arg Pro Pro Ser Pro Arg Ala Lys Ala
        50                  55                  60

Pro Gly Pro Ala Gln Pro Arg Pro Ala Lys Ala Pro Val Lys Thr Pro
65                  70                  75                  80

Ala Lys Arg Gly Pro Ala Pro Lys Arg Lys Pro Gly Lys Arg Glu Arg
                85                  90                  95

Thr Ala Leu Arg Leu Gln Ala Asp Arg Val Phe Pro Val Val Asn Asp
            100                 105                 110

Lys Gln Val Thr Val Gly Tyr Ala Val Ala Leu Glu Gly Arg Val Met
        115                 120                 125

Lys Pro Leu His Val Lys Gly Thr Ile Asp His Pro Leu Leu Ala Ser
    130                 135                 140

Leu Lys Phe Thr Lys Ser Thr Ser Phe Asp Met Glu Tyr Ala Ala Leu
145                 150                 155                 160

Pro Thr Thr Met Arg Ser Glu Ala Phe Ala Tyr Thr Ser Glu His Pro
                165                 170                 175

Asp Gly Phe Tyr Ser Trp Val His Gly Ala Val Gln Cys Thr Asn Gly
            180                 185                 190
```

-continued

```
Arg Phe Ser Ile Pro Thr Gly Ala Gly Gly Pro Gly Asp Ser Gly Arg
            195                 200                 205
Pro Ile Leu Asp Asn Thr Gly Lys Val Val Ala Leu Val Leu Gly Gly
    210                 215                 220
Ala Asn Glu Gly Thr Arg Thr Ser Leu Ser Val Val Thr Trp Asn Lys
225                 230                 235                 240
Ser Gly Thr Ala Ala Lys Thr Thr Pro Asp Asp Thr Val Glu Trp Ser
                245                 250                 255
Ala Ile Val Thr Ala Leu Cys Val Leu Gly Asn Ala Ser Phe Thr Cys
                260                 265                 270
Thr Glu Pro Pro Ile Cys Phe Asp Thr His Pro Gly Asp Thr Leu Gly
            275                 280                 285
Met Leu Glu Asp Asn Val Asp His Pro Met Tyr Tyr Asp Leu Met Tyr
    290                 295                 300
Ala Ala Leu Leu Cys Asn His Gln Gln Lys Arg Ala Arg Arg Ala Val
305                 310                 315                 320
Ala Pro Lys Pro Asp Glu Tyr Arg Leu Ala Ser Pro Tyr Val Gly Arg
                325                 330                 335
Cys Ala Ala Cys Ser Asn Gly Ile Thr Cys Phe Ser Pro Ile Lys Leu
                340                 345                 350
Glu Ser Val Trp Thr Thr Pro His Ser Ser Val Leu Lys Met Gln Leu
            355                 360                 365
Ser Val Leu Phe Gly Ile Asp Glu Thr Gly Lys Leu Asp Asn Thr Val
    370                 375                 380
Leu Ser Tyr Met Ser Pro Thr Glu His Thr Val Lys Ser Met Pro Ile
385                 390                 395                 400
Thr Ala Leu Thr Ala Ser Thr Thr Gly Pro Cys Ile Ile Thr Ala Thr
                405                 410                 415
Arg Gly Tyr Phe Ala Leu Ala Gln Cys Pro Pro Gly Asp Val Leu Thr
                420                 425                 430
Val Ala Met Gly Ser His His Cys Ser Ile Glu Ser Glu His Leu Arg
            435                 440                 445
Pro Ser Val Gly Arg Glu Glu Phe Ala Ser Thr Pro Leu His Gly Val
    450                 455                 460
Arg Arg Pro Cys Ser Thr Tyr Asp Ala Ala Lys Tyr Thr Ser Thr Ser
465                 470                 475                 480
Glu Met Thr Leu His Arg Ala Lys Pro Gln Ala Ser Asp Ser Leu Leu
                485                 490                 495
Ser Ile Val Asn Asp Thr Val Gln Ile Thr Val Ser Ser Asn Leu Thr
                500                 505                 510
Val Ser Tyr Glu Cys Leu Cys Asp Gly Tyr His Ser Gly Phe Val Arg
            515                 520                 525
Ala Thr Thr Leu Ile Pro Gly Cys Thr Asn Thr Asn Gln Cys Ile Ala
    530                 535                 540
Ser Val Asn Asp Lys Thr Arg Trp Tyr Pro Asn Thr Asp Asp Phe Ile
545                 550                 555                 560
Arg His Thr Asp His Ser Pro Arg Gly Lys Ile Asn Val Pro Phe Pro
                565                 570                 575
Leu Glu Ala Gly Glu Cys Leu Val Pro Leu Ala Arg Ser Pro Ala Ile
                580                 585                 590
Arg Tyr Ser Arg Asn Glu Val Glu Leu Thr Leu Val Thr Arg Lys
            595                 600                 605
```

```
Ala Leu Leu Ser Thr Arg Gln Leu Gly Ser Glu Pro Asn Ala Thr Ser
    610                 615                 620

Glu Trp Ile Thr Ser Ser Thr Arg Arg Thr Phe Tyr Leu Pro Ala Ala
625                 630                 635                 640

Gly Leu Glu Phe Thr Trp Gly Asn Asn Asp Pro Val Arg Val Trp Pro
                645                 650                 655

Gln Ala Ser Ala Asp Gly Asp Ala His Gly Leu Pro His Glu Ile Val
            660                 665                 670

Ala Tyr Tyr Tyr Ser Arg Ser Pro Leu Phe Thr Ile Val Ala Val Thr
        675                 680                 685

Leu Ile Ser Ala Ile Val Leu Ala Ser Leu Ala Phe Cys Cys Cys Lys
    690                 695                 700

Trp Thr Ser Phe Arg Ser Ala Leu Arg Ser Pro Tyr Ala Leu Ala Pro
705                 710                 715                 720

Asn Ala Thr Val Pro Met Cys Leu Thr Leu Leu Cys Cys Ile Arg Gln
                725                 730                 735

Ala Lys Ala Asp Thr Tyr Phe Asp Ala Ala Ser Tyr Leu Trp Asn Asn
            740                 745                 750

Tyr Gln Pro Leu Phe Trp Ala Gln Leu Ala Ile Pro Thr Ala Ser Ile
        755                 760                 765

Phe Val Leu Phe Lys Cys Cys Ser Leu Ala Val Ala Phe Leu Ala Val
    770                 775                 780

Val Gly Ala Ser Leu Pro Leu Ala Ser Ala His Glu His Ala Ala Asn
785                 790                 795                 800

Val Pro Asn Ser Pro Leu Leu Ser Tyr Lys Ala Val Val Thr Arg Pro
                805                 810                 815

Gly Tyr Thr Pro Leu Ala Leu Glu Ile Arg Val Leu Glu Asn Arg Ile
            820                 825                 830

Gln Pro Thr Thr Leu Thr His Tyr Tyr Thr Cys Ser Tyr Arg Thr Val
        835                 840                 845

Val Pro Ser Pro Thr Val Lys Cys Cys Gly Ser Leu Gln Cys Gly Ser
    850                 855                 860

Ser Ser Leu Pro Asp Tyr Arg Cys Lys Val Phe Thr Gly Val Tyr Pro
865                 870                 875                 880

Phe Met Trp Gly Gly Ala Gln Cys Phe Cys Asp Thr Glu Asn Ser Gln
                885                 890                 895

Met Ser Glu Ser Tyr Val Asp Lys Asp Pro Ser Cys Pro Thr Asp His
            900                 905                 910

Ala Glu Ala Val Ala Thr Gln Asn Pro Val Val Arg Ala Thr Leu Gln
        915                 920                 925

Ile Thr Ile Gly Asn Ala Thr Thr Arg Thr Asp Val Tyr Val Asn Gly
    930                 935                 940

Val Ser Pro Ser Tyr Thr Asn Gly Ala Lys Val Ile Ala Gly Pro Leu
945                 950                 955                 960

Ser Ser Val Trp Ser Pro Phe Ala Asp Lys Val Val Ile Tyr Gln Arg
                965                 970                 975

Arg Val Tyr Asn His Ala Phe Pro Glu Tyr Gly Ala Gly Thr Pro Gly
            980                 985                 990

Thr Phe Gly Asp Leu Gln Leu Pro  Ser Leu Arg Ala Lys  Asp Phe Phe
        995                 1000                1005

Ala Asn  Thr Gly Leu Val Leu  Asn Arg Pro Asp Thr  Ser Ser Leu
    1010                1015                1020

His Val  Pro Tyr Thr Gln Val  Pro Ser Gly Phe Val  Thr Trp Arg
```

```
           1025                1030                1035

Asp Gln His Leu Pro Asp Leu Gln Gln Thr Ala Pro Tyr Gly Cys
        1040                1045                1050

Ala Ile Ser Ser Ser Pro Leu Gln Ala Ile Asn Cys Ser Tyr Gly
        1055                1060                1065

Ser Ile Pro Val Ser Ile Asp Ile Pro Asp Ala Ser Phe Thr Arg
        1070                1075                1080

Ser Phe Asp Ala Pro Ser Val Ser Ser Leu Lys Cys Thr Pro Ile
        1085                1090                1095

Glu Cys Val His Ser Ala Gly Tyr Gly Gly Leu Leu Arg Leu Asp
        1100                1105                1110

Tyr Val Ala Asp Lys Ala Gly Thr Cys Ser Leu His Ser His Ser
        1115                1120                1125

Asp Ala Val Leu Met Lys Asp Ser Leu Leu Ser Ile Asn Ala Thr
        1130                1135                1140

Gly Ser Tyr Thr Gly Leu Phe Ser Thr Ala Ser Pro Gln Val Lys
        1145                1150                1155

Phe Thr Ile Thr Leu Cys Ser Ala Glu Val Ser Cys Glu Thr Ala
        1160                1165                1170

Cys Lys Pro Pro Leu Glu His Ala Ser Ser His Pro His Leu Thr
        1175                1180                1185

Ser Gln Thr Phe Asp Ser Ala Ile Ser Thr Ser Ala Trp Thr Trp
        1190                1195                1200

Leu Leu Ser Leu Phe Gly Gly Ser Ile Ser Leu Val Thr Val Gly
        1205                1210                1215

Ile Phe Ile Ala Ala Ala Leu Tyr Ile Val Asn Cys Arg Arg Arg
        1220                1225                1230

<210> SEQ ID NO 6
<211> LENGTH: 133
<212> TYPE: DNA
<213> ORGANISM: Eilat virus

<400> SEQUENCE: 6
cgcgcaactt ctctgcctta cggggaacac ttaagaccct ctacaactaa cctaaatagt      60
gcgcgtatta tcaatactac tagcacacta ttacccgtgt acgtaccaac ggcactactt     120
gcacaagtca aca                                                       133

<210> SEQ ID NO 7
<211> LENGTH: 51
<212> TYPE: RNA
<213> ORGANISM: Eilat virus

<400> SEQUENCE: 7 caugucacc ccgaaugacc acgccaaugc gagagccuuc ucccauugcg c               51

<210> SEQ ID NO 8
<211> LENGTH: 51
<212> TYPE: RNA
<213> ORGANISM: Trocara virus

<400> SEQUENCE: 8
gcaggucacu gccaaugacc augcuaaugc cagagcguuc ucgcaucugg c              51

<210> SEQ ID NO 9
<211> LENGTH: 51
<212> TYPE: RNA
```

<213> ORGANISM: Aura virus

<400> SEQUENCE: 9
gcaggucacu ccgaaugacc augcuaaugc cagagcuuuu ucgcaucugg c        51

<210> SEQ ID NO 10
<211> LENGTH: 51
<212> TYPE: RNA
<213> ORGANISM: Whataroa virus

<400> SEQUENCE: 10
gcaggccacg ccaaaugacc augcuaaugc cagagccuuu ucgcaucugg c        51

<210> SEQ ID NO 11
<211> LENGTH: 51
<212> TYPE: RNA
<213> ORGANISM: Sindbis virus

<400> SEQUENCE: 11
gcaggucacu ccaaaugacc augcuaaugc cagagcauuu ucgcaucugg c        51

<210> SEQ ID NO 12
<211> LENGTH: 51
<212> TYPE: RNA
<213> ORGANISM: Western equine encephalomyelitis virus

<400> SEQUENCE: 12
gcaggucacu gacaacgacc augcuaaugc cagagcauuu ucgcaugugg c        51

<210> SEQ ID NO 13
<211> LENGTH: 51
<212> TYPE: RNA
<213> ORGANISM: Eastern equine encephalomyelitis virus

<400> SEQUENCE: 13
gcaggucacu gacaaugacc augcuaaugc uagggcguuu ucgcaccuag c        51

<210> SEQ ID NO 14
<211> LENGTH: 51
<212> TYPE: RNA
<213> ORGANISM: Venezuelan equine encephalitis virus

<400> SEQUENCE: 14
gcaggucacu gauaaugacc augcuaaugc cagagcguuu ucgcaucugg c        51

<210> SEQ ID NO 15
<211> LENGTH: 51
<212> TYPE: RNA
<213> ORGANISM: Chikungunya virus

<400> SEQUENCE: 15
gcaggucaca ucgaaugacc augcuaaugc uagagcguuc ucgcaucuag c        51

<210> SEQ ID NO 16
<211> LENGTH: 51
<212> TYPE: RNA
<213> ORGANISM: Ross River virus

<400> SEQUENCE: 16
gcaggucaca ccuaaugacc augcuaaugc cagagccuuu ucgcaucugg c        51

<210> SEQ ID NO 17
<211> LENGTH: 51

-continued

```
<212> TYPE: RNA
<213> ORGANISM: Una virus

<400> SEQUENCE: 17
gcaggucacu ccaaaugacc augcgaacgc gagggcuuuc ucgcaccucg c          51

<210> SEQ ID NO 18
<211> LENGTH: 51
<212> TYPE: RNA
<213> ORGANISM: Semliki Forest virus

<400> SEQUENCE: 18
gcaggucaca ccaaaugacc augcaaaugc cagagcauuu ucgcaccugg c          51

<210> SEQ ID NO 19
<211> LENGTH: 51
<212> TYPE: RNA
<213> ORGANISM: Middelburg virus

<400> SEQUENCE: 19
gcaggucaca ccgaaugacc augcuaacgc gagggcguuu ucgcaccuug c          51

<210> SEQ ID NO 20
<211> LENGTH: 51
<212> TYPE: RNA
<213> ORGANISM: Barmah Forest virus

<400> SEQUENCE: 20
gcagaccaca ccaaacgauc augcacacgc gagggcguuu ucgcaccuug c          51

<210> SEQ ID NO 21
<211> LENGTH: 51
<212> TYPE: RNA
<213> ORGANISM: Ndumu virus

<400> SEQUENCE: 21
gcaggucaca ccgaaugacc augcuaaugc aagagcguuu ucgcaucuug c          51

<210> SEQ ID NO 22
<211> LENGTH: 51
<212> TYPE: RNA
<213> ORGANISM: SES virus

<400> SEQUENCE: 22
gcaggucaca ccuaaugacc augccaaugc cagagcuuuu ucgcaucugg c          51

<210> SEQ ID NO 23
<211> LENGTH: 51
<212> TYPE: RNA
<213> ORGANISM: SPD virus

<400> SEQUENCE: 23
caauaggucg ucuaacgacc augccgccgc cagagcuuuc ucccacuugg c          51

<210> SEQ ID NO 24
<211> LENGTH: 8
<212> TYPE: PRT
<213> ORGANISM: Eilat virus

<400> SEQUENCE: 24

Asp Ile Gly Gly Ala Leu Val Glu
1               5
```

```
<210> SEQ ID NO 25
<211> LENGTH: 8
<212> TYPE: PRT
<213> ORGANISM: Eilat virus

<400> SEQUENCE: 25

Gly Val Gly Ala Ala Pro Ser Tyr
1               5

<210> SEQ ID NO 26
<211> LENGTH: 8
<212> TYPE: PRT
<213> ORGANISM: Eilat virus

<400> SEQUENCE: 26

Gly Ala Gly Gly Tyr Ile Phe Ser
1               5

<210> SEQ ID NO 27
<211> LENGTH: 8
<212> TYPE: PRT
<213> ORGANISM: Eilat virus

<400> SEQUENCE: 27

Thr Val Glu Trp Ser Ala Ile Val
1               5

<210> SEQ ID NO 28
<211> LENGTH: 8
<212> TYPE: PRT
<213> ORGANISM: Eilat virus

<400> SEQUENCE: 28

Arg Ala Arg Arg Ala Val Ala Pro
1               5

<210> SEQ ID NO 29
<211> LENGTH: 9
<212> TYPE: PRT
<213> ORGANISM: Trocara virus

<400> SEQUENCE: 29

Asp Ile Gly Gly Ala Ala Leu Val Asp
1               5

<210> SEQ ID NO 30
<211> LENGTH: 8
<212> TYPE: PRT
<213> ORGANISM: Trocara virus

<400> SEQUENCE: 30

Gly Ile Gly Cys Ala Pro Ser Tyr
1               5

<210> SEQ ID NO 31
<211> LENGTH: 8
<212> TYPE: PRT
<213> ORGANISM: Trocara virus

<400> SEQUENCE: 31

Gly Val Gly Gly Tyr Ile Phe Ser
1               5

<210> SEQ ID NO 32
<211> LENGTH: 8
```

```
<212> TYPE: PRT
<213> ORGANISM: Trocara virus

<400> SEQUENCE: 32

Thr Val Lys Trp Ser Ala Ala Thr
1               5

<210> SEQ ID NO 33
<211> LENGTH: 8
<212> TYPE: PRT
<213> ORGANISM: Trocara virus

<400> SEQUENCE: 33

Arg Pro Lys Arg Ser Thr Glu Leu
1               5

<210> SEQ ID NO 34
<211> LENGTH: 8
<212> TYPE: PRT
<213> ORGANISM: Aura virus

<400> SEQUENCE: 34

Asp Ala Gly Ala Ala Leu Val Glu
1               5

<210> SEQ ID NO 35
<211> LENGTH: 8
<212> TYPE: PRT
<213> ORGANISM: Aura virus

<400> SEQUENCE: 35

Gly Ser Gly Ala Ala Pro Ser Tyr
1               5

<210> SEQ ID NO 36
<211> LENGTH: 8
<212> TYPE: PRT
<213> ORGANISM: Aura virus

<400> SEQUENCE: 36

Gly Val Gly Gly Tyr Ile Phe Ser
1               5

<210> SEQ ID NO 37
<211> LENGTH: 8
<212> TYPE: PRT
<213> ORGANISM: Aura virus

<400> SEQUENCE: 37

Thr Val Glu Trp Ser Arg Ala Ile
1               5

<210> SEQ ID NO 38
<211> LENGTH: 8
<212> TYPE: PRT
<213> ORGANISM: Aura virus

<400> SEQUENCE: 38

Arg His Val Arg Ser Thr Pro Thr
1               5

<210> SEQ ID NO 39
<211> LENGTH: 8
<212> TYPE: PRT
<213> ORGANISM: Whataroa virus
```

```
<400> SEQUENCE: 39

Asp Ile Gly Ala Ala Leu Val Glu
1               5

<210> SEQ ID NO 40
<211> LENGTH: 8
<212> TYPE: PRT
<213> ORGANISM: Whataroa virus

<400> SEQUENCE: 40

Gly Val Gly Ala Ala Pro Ser Tyr
1               5

<210> SEQ ID NO 41
<211> LENGTH: 8
<212> TYPE: PRT
<213> ORGANISM: Whataroa virus

<400> SEQUENCE: 41

Gly Val Gly Gly Tyr Ile Phe Ser
1               5

<210> SEQ ID NO 42
<211> LENGTH: 8
<212> TYPE: PRT
<213> ORGANISM: Whataroa virus

<400> SEQUENCE: 42

Thr Glu Glu Trp Ser Ala Ala Ala
1               5

<210> SEQ ID NO 43
<211> LENGTH: 8
<212> TYPE: PRT
<213> ORGANISM: Whataroa virus

<400> SEQUENCE: 43

Arg His Lys Arg Ser Ile Thr Asp
1               5

<210> SEQ ID NO 44
<211> LENGTH: 8
<212> TYPE: PRT
<213> ORGANISM: Sindbis virus

<400> SEQUENCE: 44

Asp Ile Gly Ala Ala Leu Val Glu
1               5

<210> SEQ ID NO 45
<211> LENGTH: 8
<212> TYPE: PRT
<213> ORGANISM: Sindbis virus

<400> SEQUENCE: 45

Gly Val Gly Ala Ala Pro Ser Tyr
1               5

<210> SEQ ID NO 46
<211> LENGTH: 8
<212> TYPE: PRT
<213> ORGANISM: Sindbis virus

<400> SEQUENCE: 46
```

Gly Val Gly Gly Tyr Ile Phe Ser
1               5

<210> SEQ ID NO 47
<211> LENGTH: 8
<212> TYPE: PRT
<213> ORGANISM: Sindbis virus

<400> SEQUENCE: 47

Thr Glu Glu Trp Ser Ala Ala Pro
1               5

<210> SEQ ID NO 48
<211> LENGTH: 8
<212> TYPE: PRT
<213> ORGANISM: Sindbis virus

<400> SEQUENCE: 48

Arg Ser Lys Arg Ser Val Ile Asp
1               5

<210> SEQ ID NO 49
<211> LENGTH: 8
<212> TYPE: PRT
<213> ORGANISM: Western equine encephalomyelitis virus

<400> SEQUENCE: 49

Glu Ala Gly Ala Gly Ser Val Glu
1               5

<210> SEQ ID NO 50
<211> LENGTH: 8
<212> TYPE: PRT
<213> ORGANISM: Western equine encephalomyelitis virus

<400> SEQUENCE: 50

Glu Ala Gly Arg Ala Pro Ala Tyr
1               5

<210> SEQ ID NO 51
<211> LENGTH: 8
<212> TYPE: PRT
<213> ORGANISM: Western equine encephalomyelitis virus

<400> SEQUENCE: 51

Glu Ala Gly Ala Tyr Ile Phe Ser
1               5

<210> SEQ ID NO 52
<211> LENGTH: 8
<212> TYPE: PRT
<213> ORGANISM: Western equine encephalomyelitis virus

<400> SEQUENCE: 52

Ser Glu Ser Trp Ser Leu Val Thr
1               5

<210> SEQ ID NO 53
<211> LENGTH: 8
<212> TYPE: PRT
<213> ORGANISM: Western equine encephalomyelitis virus

<400> SEQUENCE: 53

Arg Gln Lys Arg Ser Ile Thr Asp

```
<210> SEQ ID NO 54
<211> LENGTH: 8
<212> TYPE: PRT
<213> ORGANISM: Eastern equine encephalomyelitis virus

<400> SEQUENCE: 54

Glu Ala Gly Ala Gly Ser Val Glu
1               5

<210> SEQ ID NO 55
<211> LENGTH: 8
<212> TYPE: PRT
<213> ORGANISM: Eastern equine encephalomyelitis virus

<400> SEQUENCE: 55

Glu Ala Gly Arg Ala Pro Ser Ala
1               5

<210> SEQ ID NO 56
<211> LENGTH: 8
<212> TYPE: PRT
<213> ORGANISM: Eastern equine encephalomyelitis virus

<400> SEQUENCE: 56

Glu Ala Gly Ala Tyr Ile Phe Ser
1               5

<210> SEQ ID NO 57
<211> LENGTH: 8
<212> TYPE: PRT
<213> ORGANISM: Eastern equine encephalomyelitis virus

<400> SEQUENCE: 57

Ser Glu Pro Trp Ser Leu Ala Thr
1               5

<210> SEQ ID NO 58
<211> LENGTH: 8
<212> TYPE: PRT
<213> ORGANISM: Eastern equine encephalomyelitis virus

<400> SEQUENCE: 58

Arg Thr Arg Arg Asp Leu Asp Thr
1               5

<210> SEQ ID NO 59
<211> LENGTH: 8
<212> TYPE: PRT
<213> ORGANISM: Venezuelan equine encephalitis virus

<400> SEQUENCE: 59

Glu Ala Gly Ala Gly Ser Val Glu
1               5

<210> SEQ ID NO 60
<211> LENGTH: 8
<212> TYPE: PRT
<213> ORGANISM: Venezuelan equine encephalitis virus

<400> SEQUENCE: 60

Glu Ala Gly Cys Ala Pro Ser Tyr
1               5
```

```
<210> SEQ ID NO 61
<211> LENGTH: 8
<212> TYPE: PRT
<213> ORGANISM: Venezuelan equine encephalitis virus

<400> SEQUENCE: 61

Asp Ala Gly Ala Tyr Ile Phe Ser
1               5

<210> SEQ ID NO 62
<211> LENGTH: 8
<212> TYPE: PRT
<213> ORGANISM: Venezuelan equine encephalitis virus

<400> SEQUENCE: 62

Cys Glu Gln Trp Ser Leu Val Thr
1               5

<210> SEQ ID NO 63
<211> LENGTH: 8
<212> TYPE: PRT
<213> ORGANISM: Venezuelan equine encephalitis virus

<400> SEQUENCE: 63

Arg Lys Arg Arg Ser Thr Glu Glu
1               5

<210> SEQ ID NO 64
<211> LENGTH: 8
<212> TYPE: PRT
<213> ORGANISM: Chikungunya virus

<400> SEQUENCE: 64

Arg Ala Gly Ala Gly Ile Ile Glu
1               5

<210> SEQ ID NO 65
<211> LENGTH: 8
<212> TYPE: PRT
<213> ORGANISM: Chikungunya virus

<400> SEQUENCE: 65

Arg Ala Gly Cys Ala Pro Ser Tyr
1               5

<210> SEQ ID NO 66
<211> LENGTH: 8
<212> TYPE: PRT
<213> ORGANISM: Chikungunya virus

<400> SEQUENCE: 66

Arg Ala Gly Gly Tyr Ile Phe Ser
1               5

<210> SEQ ID NO 67
<211> LENGTH: 8
<212> TYPE: PRT
<213> ORGANISM: Chikungunya virus

<400> SEQUENCE: 67

Ala Glu Glu Trp Ser Leu Ala Ile
1               5

<210> SEQ ID NO 68
```

```
<211> LENGTH: 8
<212> TYPE: PRT
<213> ORGANISM: Chikungunya virus

<400> SEQUENCE: 68

Arg Gln Arg Arg Ser Ile Lys Asp
1               5

<210> SEQ ID NO 69
<211> LENGTH: 8
<212> TYPE: PRT
<213> ORGANISM: Ross River virus

<400> SEQUENCE: 69

Arg Ala Gly Ala Gly Val Val Glu
1               5

<210> SEQ ID NO 70
<211> LENGTH: 8
<212> TYPE: PRT
<213> ORGANISM: Ross River virus

<400> SEQUENCE: 70

Thr Ala Gly Cys Ala Pro Ser Tyr
1               5

<210> SEQ ID NO 71
<211> LENGTH: 8
<212> TYPE: PRT
<213> ORGANISM: Ross River virus

<400> SEQUENCE: 71

Arg Ala Gly Ala Tyr Ile Phe Ser
1               5

<210> SEQ ID NO 72
<211> LENGTH: 8
<212> TYPE: PRT
<213> ORGANISM: Ross River virus

<400> SEQUENCE: 72

Thr Glu Glu Trp Ser Ala Ala Leu
1               5

<210> SEQ ID NO 73
<211> LENGTH: 8
<212> TYPE: PRT
<213> ORGANISM: Ross River virus

<400> SEQUENCE: 73

Arg His Arg Arg Ser Val Thr Glu
1               5

<210> SEQ ID NO 74
<211> LENGTH: 8
<212> TYPE: PRT
<213> ORGANISM: Una virus

<400> SEQUENCE: 74

Arg Ala Gly Ala Gly Val Val Glu
1               5

<210> SEQ ID NO 75
<211> LENGTH: 8
<212> TYPE: PRT
```

```
<213> ORGANISM: Una virus

<400> SEQUENCE: 75

Thr Ala Gly Cys Ala Pro Ala Tyr
1               5

<210> SEQ ID NO 76
<211> LENGTH: 8
<212> TYPE: PRT
<213> ORGANISM: Una virus

<400> SEQUENCE: 76

Arg Ala Gly Gly Tyr Thr Phe Ser
1               5

<210> SEQ ID NO 77
<211> LENGTH: 8
<212> TYPE: PRT
<213> ORGANISM: Una virus

<400> SEQUENCE: 77

Thr Val Glu Trp Ser Ala Pro Leu
1               5

<210> SEQ ID NO 78
<211> LENGTH: 8
<212> TYPE: PRT
<213> ORGANISM: Una virus

<400> SEQUENCE: 78

Arg His Arg Arg Ser Val Thr Gln
1               5

<210> SEQ ID NO 79
<211> LENGTH: 8
<212> TYPE: PRT
<213> ORGANISM: Semliki Forest virus

<400> SEQUENCE: 79

His Ala Gly Ala Gly Val Val Glu
1               5

<210> SEQ ID NO 80
<211> LENGTH: 8
<212> TYPE: PRT
<213> ORGANISM: Semliki Forest virus

<400> SEQUENCE: 80

Thr Ala Gly Cys Ala Pro Ser Tyr
1               5

<210> SEQ ID NO 81
<211> LENGTH: 8
<212> TYPE: PRT
<213> ORGANISM: Semliki Forest virus

<400> SEQUENCE: 81

Arg Ala Gly Ala Tyr Ile Phe Ser
1               5

<210> SEQ ID NO 82
<211> LENGTH: 8
<212> TYPE: PRT
<213> ORGANISM: Semliki Forest virus
```

<400> SEQUENCE: 82

Ser Glu Glu Trp Ser Ala Pro Leu
1               5

<210> SEQ ID NO 83
<211> LENGTH: 8
<212> TYPE: PRT
<213> ORGANISM: Semliki Forest virus

<400> SEQUENCE: 83

Arg His Arg Arg Ser Val Ser Gln
1               5

<210> SEQ ID NO 84
<211> LENGTH: 8
<212> TYPE: PRT
<213> ORGANISM: Middelburg virus

<400> SEQUENCE: 84

Arg Ala Gly Ala Gly Val Val Asn
1               5

<210> SEQ ID NO 85
<211> LENGTH: 8
<212> TYPE: PRT
<213> ORGANISM: Middelburg virus

<400> SEQUENCE: 85

Thr Ala Gly Cys Ala Pro Ser Tyr
1               5

<210> SEQ ID NO 86
<211> LENGTH: 8
<212> TYPE: PRT
<213> ORGANISM: Middelburg virus

<400> SEQUENCE: 86

Arg Ala Gly Ala Tyr Ile Phe Ser
1               5

<210> SEQ ID NO 87
<211> LENGTH: 8
<212> TYPE: PRT
<213> ORGANISM: Middelburg virus

<400> SEQUENCE: 87

Thr Glu Glu Trp Thr Ala Leu Val
1               5

<210> SEQ ID NO 88
<211> LENGTH: 8
<212> TYPE: PRT
<213> ORGANISM: Middelburg virus

<400> SEQUENCE: 88

Arg Arg Arg Arg Gly Leu Thr Glu
1               5

<210> SEQ ID NO 89
<211> LENGTH: 8
<212> TYPE: PRT
<213> ORGANISM: Barmah Forest virus

<400> SEQUENCE: 89

Arg Ala Gly Glu Gly Val Val Glu
1               5

<210> SEQ ID NO 90
<211> LENGTH: 8
<212> TYPE: PRT
<213> ORGANISM: Barmah Forest virus

<400> SEQUENCE: 90

Pro Ala Gly Ser Ala Pro Ala Tyr
1               5

<210> SEQ ID NO 91
<211> LENGTH: 8
<212> TYPE: PRT
<213> ORGANISM: Barmah Forest virus

<400> SEQUENCE: 91

Arg Ala Gly Gly Tyr Ile Phe Ser
1               5

<210> SEQ ID NO 92
<211> LENGTH: 8
<212> TYPE: PRT
<213> ORGANISM: Barmah Forest virus

<400> SEQUENCE: 92

Ser Val Glu Trp Ser Ala Ala Ala
1               5

<210> SEQ ID NO 93
<211> LENGTH: 8
<212> TYPE: PRT
<213> ORGANISM: Barmah Forest virus

<400> SEQUENCE: 93

Arg Pro Lys Arg Ser Val Ala His
1               5

<210> SEQ ID NO 94
<211> LENGTH: 8
<212> TYPE: PRT
<213> ORGANISM: Ndumu virus

<400> SEQUENCE: 94

Arg Ala Gly Ala Gly Val Val Glu
1               5

<210> SEQ ID NO 95
<211> LENGTH: 8
<212> TYPE: PRT
<213> ORGANISM: Ndumu virus

<400> SEQUENCE: 95

Arg Ala Gly Ala Ala Pro Ala Tyr
1               5

<210> SEQ ID NO 96
<211> LENGTH: 8
<212> TYPE: PRT
<213> ORGANISM: Ndumu virus

<400> SEQUENCE: 96

Arg Ala Gly Ala Tyr Ile Phe Ser
1               5

```
<210> SEQ ID NO 97
<211> LENGTH: 8
<212> TYPE: PRT
<213> ORGANISM: Ndumu virus

<400> SEQUENCE: 97

Ser Val Glu Trp Ser Ala Ala Ala
1               5

<210> SEQ ID NO 98
<211> LENGTH: 8
<212> TYPE: PRT
<213> ORGANISM: Ndumu virus

<400> SEQUENCE: 98

Arg His Arg Arg Ala Ala Gln His
1               5

<210> SEQ ID NO 99
<211> LENGTH: 8
<212> TYPE: PRT
<213> ORGANISM: SES virus

<400> SEQUENCE: 99

Arg Ala Gly Ala Gly Val Val Glu
1               5

<210> SEQ ID NO 100
<211> LENGTH: 8
<212> TYPE: PRT
<213> ORGANISM: SES virus

<400> SEQUENCE: 100

Pro Ala Gly Thr Ala Pro Asn Tyr
1               5

<210> SEQ ID NO 101
<211> LENGTH: 8
<212> TYPE: PRT
<213> ORGANISM: SES virus

<400> SEQUENCE: 101

Arg Ala Gly Ala Tyr Ile Phe Ser
1               5

<210> SEQ ID NO 102
<211> LENGTH: 8
<212> TYPE: PRT
<213> ORGANISM: SES virus

<400> SEQUENCE: 102

Thr Val Glu Trp Ser Ala Leu Thr
1               5

<210> SEQ ID NO 103
<211> LENGTH: 8
<212> TYPE: PRT
<213> ORGANISM: SES virus

<400> SEQUENCE: 103

Arg Gly Lys Arg Ser Val Ala Ser
1               5
```

```
<210> SEQ ID NO 104
<211> LENGTH: 8
<212> TYPE: PRT
<213> ORGANISM: SPD virus

<400> SEQUENCE: 104

Gly Ala Gly Ala Thr Ile Ile Asp
1               5

<210> SEQ ID NO 105
<211> LENGTH: 8
<212> TYPE: PRT
<213> ORGANISM: SPD virus

<400> SEQUENCE: 105

Met Val Gly Ala Ala Pro Gly Tyr
1               5

<210> SEQ ID NO 106
<211> LENGTH: 8
<212> TYPE: PRT
<213> ORGANISM: SPD virus

<400> SEQUENCE: 106

Gly Leu Gly Gly Tyr Ile Phe Ser
1               5

<210> SEQ ID NO 107
<211> LENGTH: 8
<212> TYPE: PRT
<213> ORGANISM: SPD virus

<400> SEQUENCE: 107

Ala Ile Pro Trp Thr Arg Ala Pro
1               5

<210> SEQ ID NO 108
<211> LENGTH: 8
<212> TYPE: PRT
<213> ORGANISM: SPD virus

<400> SEQUENCE: 108

Arg Arg Lys Arg Ala Val Ser Thr
1               5

<210> SEQ ID NO 109
<211> LENGTH: 24
<212> TYPE: RNA
<213> ORGANISM: Eilat virus

<400> SEQUENCE: 109
cccucuacaa cuaaccuaaa uagu                                          24

<210> SEQ ID NO 110
<211> LENGTH: 24
<212> TYPE: RNA
<213> ORGANISM: Aura virus

<400> SEQUENCE: 110
accucuacgg ugguccuaaa uaga                                          24

<210> SEQ ID NO 111
<211> LENGTH: 24
<212> TYPE: RNA
<213> ORGANISM: Whataroa virus
```

```
<400> SEQUENCE: 111
agcucuacgg cgguccuaaa uaga                                         24

<210> SEQ ID NO 112
<211> LENGTH: 24
<212> TYPE: RNA
<213> ORGANISM: Sindbis virus

<400> SEQUENCE: 112
aucucuacgg ugguccuaaa uagu                                         24

<210> SEQ ID NO 113
<211> LENGTH: 24
<212> TYPE: RNA
<213> ORGANISM: Western equine encephalomyelitis virus

<400> SEQUENCE: 113
cccucuacgg cugaccuaaa uagu                                         24

<210> SEQ ID NO 114
<211> LENGTH: 24
<212> TYPE: RNA
<213> ORGANISM: Eastern equine encephalomyelitis virus

<400> SEQUENCE: 114
cccucuacgg cugaccuaaa uagu                                         24

<210> SEQ ID NO 115
<211> LENGTH: 24
<212> TYPE: RNA
<213> ORGANISM: Venezuelan equine encephalitis virus

<400> SEQUENCE: 115
cucucuacgg cuaaccugaa ugga                                         24

<210> SEQ ID NO 116
<211> LENGTH: 24
<212> TYPE: RNA
<213> ORGANISM: Chikungunya virus

<400> SEQUENCE: 116
cuuucuacgg cgguccugaa uggg                                         24

<210> SEQ ID NO 117
<211> LENGTH: 24
<212> TYPE: RNA
<213> ORGANISM: Ross River virus

<400> SEQUENCE: 117
accucuacgg ugguccuaaa uaga                                         24

<210> SEQ ID NO 118
<211> LENGTH: 24
<212> TYPE: RNA
<213> ORGANISM: Semliki Forest virus

<400> SEQUENCE: 118
accucuacgg cgguccuaga uugg                                         24

<210> SEQ ID NO 119
<211> LENGTH: 24
<212> TYPE: RNA
```

<213> ORGANISM: Middelburg virus

<400> SEQUENCE: 119
accucuacgg cgguccuaaa uagu                                          24

<210> SEQ ID NO 120
<211> LENGTH: 24
<212> TYPE: RNA
<213> ORGANISM: Barmah Forest virus

<400> SEQUENCE: 120
aucucuacgg ugguccuaaa uagu                                          24

<210> SEQ ID NO 121
<211> LENGTH: 24
<212> TYPE: RNA
<213> ORGANISM: SES virus

<400> SEQUENCE: 121
cgcucuacgg cuguccuaaa uaga                                          24

<210> SEQ ID NO 122
<211> LENGTH: 24
<212> TYPE: RNA
<213> ORGANISM: SPD virus

<400> SEQUENCE: 122
cccucuacgu cuaaccuuaa uauu                                          24

<210> SEQ ID NO 123
<211> LENGTH: 20
<212> TYPE: RNA
<213> ORGANISM: Eilat virus

<400> SEQUENCE: 123
aauuuguuuu uaauauuucc                                               20

<210> SEQ ID NO 124
<211> LENGTH: 19
<212> TYPE: RNA
<213> ORGANISM: Aura virus

<400> SEQUENCE: 124
auuuuguuuu uaauauuuc                                                19

<210> SEQ ID NO 125
<211> LENGTH: 19
<212> TYPE: RNA
<213> ORGANISM: Sindbis virus

<400> SEQUENCE: 125
auuuuguuuu uaacauuuc                                                19

<210> SEQ ID NO 126
<211> LENGTH: 19
<212> TYPE: RNA
<213> ORGANISM: Western equine encephalomyelitis virus

<400> SEQUENCE: 126
auuuuguuuu uaaaauuuc                                                19

<210> SEQ ID NO 127
<211> LENGTH: 19

```
<212> TYPE: RNA
<213> ORGANISM: Eastern equine encephalomyelitis virus

<400> SEQUENCE: 127
auuuuguuuu uaauauuuc                                              19

<210> SEQ ID NO 128
<211> LENGTH: 19
<212> TYPE: RNA
<213> ORGANISM: Venezuelan equine encephalitis virus

<400> SEQUENCE: 128
auuuuguuuu uaauauuuc                                              19

<210> SEQ ID NO 129
<211> LENGTH: 21
<212> TYPE: RNA
<213> ORGANISM: Ross River virus

<400> SEQUENCE: 129
gauuuguuuu uaauauuuua c                                           21

<210> SEQ ID NO 130
<211> LENGTH: 19
<212> TYPE: RNA
<213> ORGANISM: Semliki Forest virus

<400> SEQUENCE: 130
aauugguuuu uaauauuuc                                              19

<210> SEQ ID NO 131
<211> LENGTH: 19
<212> TYPE: RNA
<213> ORGANISM: Middelburg virus

<400> SEQUENCE: 131
cuauugguuu uaauauucc                                              19

<210> SEQ ID NO 132
<211> LENGTH: 21
<212> TYPE: RNA
<213> ORGANISM: Barmah Forest virus

<400> SEQUENCE: 132
auuuguuuuu uaauauuuua c                                           21

<210> SEQ ID NO 133
<211> LENGTH: 25
<212> TYPE: RNA
<213> ORGANISM: SPD virus

<400> SEQUENCE: 133
cuauugguuu uaaaauuuuc aauac                                       25
```

ALPHAVIRUS COMPOSITIONS AND METHODS OF USE

This application is a continuation in part of and claims priority to International Patent Application number PCT/US2011/066996 filed Dec. 22, 2011 (pending) and U.S. Provisional Patent Application Ser. No. 61/459,989 filed Dec. 22, 2010. Each of the above referenced applications is incorporated herein by reference in its entirety.

STATEMENT REGARDING FEDERALLY FUNDED RESEARCH

This invention was made with government support under N01-AI-30027 awarded by the National Institutes of Health/National Institute of Allergy and Infectious Disease. The government has certain rights in the invention.

REFERENCE TO SEQUENCE LISTING

A sequence listing required by 37 CFR 1.821-1.825 is being submitted electronically with this application. The sequence listing is incorporated herein by reference.

BACKGROUND

Current classification of the genus *Alphavirus* includes 29 species that can be classified into nine complexes based on antigenic and/or genetic similarities (Powers et al., *J Virol.*, 2001, 75 (21): 10118-31). Barmah Forest, Ndumu, Middelburg, and Semliki Forest complexes consist of almost exclusively Old World viruses whereas Venezuelan equine encephalitis (VEE), Eastern equine encephalitis (EEE), and Trocara complexes are comprised of New World viruses (id.). Western equine encephalitis (WEE) complex contains both Old World (Whataroa and Sindbis) and New World (Aura) viruses as well as recombinant viruses (WEE, Highland J, Fort Morgan and Buggy Creek) (Powers et al., *J Virol.*, 2001, 75(21):10118-31; Hahn et al., *Proc Natl Acad Sci USA*. 1988, 85(16):5997-6001; Weaver et al., *J. Virol.* 1997, 71:613-623). The latter viruses are decedents of a recombinant virus that obtained nonstructural and capsid genes from an EEE-like virus and the remaining genes from a Sindbis-like virus (Hahn et al., *Proc Natl Acad Sci USA*. 1988, 85(16):5997-6001; Weaver et al., *J. Virol.* 1997, 71:613-623). Lastly, the aquatic alphavirus, salmonid alphavirus (SAV), consists of two species, salmon pancreatic disease virus (SPDV) and sleeping sickness virus (SDV) that are distantly related to all other alphaviruses (Weston et al., *J Virol.* 2002, 76(12):6155-63).

Most alphaviruses are maintained in natural cycles between arthropod vectors, mainly mosquitoes, and susceptible vertebrate hosts (Strauss and Strauss. The alphaviruses: gene expression, replication, and evolution. *Microbiol. Rev.* 1994, 58(3): 491-562). Occasionally, these cycles can spill over into the human and animal populations, and can cause disease. Human infections with Old World viruses such as Ross River (RRV), chikungunya (CHIKV), and Sindbis (SINV) are characterized by febrile illness, rash and polyarthritis (id.). In contrast, infections with New World viruses, Venezuelan equine encephalitis (VEEV), Eastern equine encephalitis (EEEV) and Western equine encephalitis (WEEV), can cause fatal encephalitis. The ability of alphaviruses to infect both invertebrates and vertebrates facilitates a broad host range that enables the viruses to be maintained in ecological niches with sporadic outbreaks in humans and animals. As such, alphaviruses have been shown to either naturally or experimentally infect many vertebrate and invertebrate hosts. Alphaviruses have been shown to infect mosquito species encompassing three genera (*Aedes* sp., *Culex* sp., *Anopheles* sp.) as well as ticks and lice (Griffin. Alphaviruses, In: Fields B N, Knipe D M, Howley P M, editors. Virology. 5th edition. New York, N.Y.: Lippincott-Raven; Pages 1023-68; Linthicum et al., *J Med. Entomol.* 1991, 28(3):405-9; La Linn et al., *J Virol.* 2001, 75(9):4103-9). Vertebrate hosts include fish, equids, birds, amphibians, reptiles, rodents, pigs, humans and non-human primates (Griffin. Alphaviruses, In: Fields B N, Knipe D M, Howley P M, editors. Virology. 5th edition. New York, N.Y.: Lippincott-Raven; Pages 1023-68; Burton et al., *Science* 1966, 154(752):1029-31). Consequently, they can be readily cultured in vitro in many vertebrate and invertebrate cell lines (Way et al., *J Gen Virol.* 1976, 30(1):123-30; Sarver and Stollar, *Virology* 1977, 80(2):390-400; Igarashi, *J Gen Virol.* 1978, 40(3):531-44). Whereas distantly related fish alphaviruses, which are not known to have arthropod vectors, exhibit a narrow host range that is at least partially due to temperature (Weston et al., *Virology* 1999, 256(2):188-95; Villoing et al., *J Virol.* 2000, 74(1):173-83; Graham et al., *J Fish Dis.* 2008, 31(11):859-68).

The viral factor(s) that underlie the broad host range of mosquito-borne alphaviruses are poorly understood. Host-restricted viruses may provide insight into these factor(s) and provide vector delivery platforms for expression or attenuation in specific hosts. But until the present invention, no mosquito-only alphaviruses were known in the genus *Alphavirus*.

SUMMARY

Described herein is a new alphavirus, Eilat virus (EILV), including nucleic acid compositions, protein compositions, viral compositions, and methods of using the same.

Certain embodiments are directed to a recombinant alphavirus expression cassette comprising an alphavirus nucleic acid segment having a nucleic acid sequence that is at least 95% identical to the nucleic acid sequence of SEQ ID NO:1 or a fragment thereof. In certain aspects the expression cassette is incorporated into isolated nucleic acids, expression vectors, or plasmids comprising all or part of an EILV nucleic acid sequence (SEQ ID NO:1). In certain aspects the nucleic acid is a recombinant DNA. The EILV nucleic acids can have at least 80, 85, 90, 95, 98, 99, or 100% sequence identity to SEQ ID NO:1 or any 10, 20, 30, 40, 50, 100, 200, 300, 400, 500, 600, 700, 800, 1000, 2000, 3000, 4000, 5000, 6000, 7000, 8000, 9000, 10000, 11000 consecutive nucleotide segment thereof, including all values and ranges there between. In certain aspects, a nucleic acid comprises a nucleotide sequence that is at least 80, 85, 90, 95, 98, 99, or 100% identical to all or a part of the non-structural protein coding region of EILV (nucleotides 57 to 7304 of SEQ ID NO:1, or any 10, 20, 30, 40, 50, 100, 200, 300, 400, 500, 600, 700, 800, 1000, 2000, 3000, 4000, 5000, 6000, or 7000 consecutive nucleotide segment thereof, including all values and ranges there between). In a further aspect, a nucleic acid comprises a nucleotide sequence that is at least 80, 85, 90, 95, 98, 99, or 100% identical to all or a part of the structural protein coding region of EILV (nucleotides 7387 to 11088 of SEQ ID NO:1, or any 10, 20, 30, 40, 50, 100, 200, 300, 400, 500, 600, 700, 800, 1000, 2000, 3000, 4000, 5000, 6000, 7000, 8000, 9000, or 10000 consecutive nucleotide segment thereof, including all values and ranges there between). In certain aspects, the nucleotide segments specifically bind EILV nucleic acids and distinguish EILV from other alphaviruses under the appropriate conditions. In certain aspects the nucleotide segments are synthetic oligonucleotides. In a further aspect the oligonucleotide is a DNA oligonucleotide or analog thereof. The EILV nucleic acids can be isolated or recombinant nucleic acids or included in a recombinant alphavirus replicon, a virus, an alphavirus, a viral particle, an alphavirus particle, an expression cassette, a host cell, an alphavirus vector, and the like. In still a further aspect, an alphavirus nucleic acid sequence can comprise a heterologous nucleic acid segment. In certain aspects, the heterologous nucleic acid segment can encode a therapeutic protein, an antigen, a toxin, or a marker.

Certain aspects are directed to an isolated, recombinant, and/or purified EILV polypeptide or peptide having at least 85, 90, 95, 98, 99, or 100% amino acid sequence identity to all or part of the amino acid sequence of SEQ ID NO:3 (EILV non-structural polyprotein) or SEQ ID NO:5 (EILV structural polyprotein). The term a "polyprotein" refers to a polypeptide that is post-translationally cleaved to yield more than one polypeptide. "Polypeptide" refers to any peptide or protein comprising a chain or polymer of amino acids joined to each other by peptide bonds. "Polypeptide" refers to both short chains of 100 amino acids or less, commonly referred to as peptides, and to longer chains, generally referred to as proteins. "Polypeptides" may contain amino acids other than the 20 gene-encoded amino acids. "Polypeptides" include amino acid sequences modified either by natural processes, such as post-translational processing, or by chemical modification techniques, which are well known in the art. In certain aspects, the isolated and/or purified EILV protein has at least 85, 90, 95, 98, 99, or 100% amino acid sequence identity to all or part of the amino acid sequence of an EILV non-structural protein including: an EILV nsP1 (amino acids 1 to 543 of SEQ ID NO:3, or any peptide having 5, 10, 15, 20, 30, 40, 50, 60, 70, 80, 90, 100, 200, 300, or 400 consecutive amino acids of SEQ ID NO:3 including all values and ranges there between), an EILV nsP2 (amino acids 544 to 1352 of SEQ ID NO:3, or any peptide of 5, 10, 15, 20, 30, 40, 50, 60, 70, 80, 90, 100, 200, 300, 400, 500, 600, or 700 consecutive amino acids of SEQ ID NO:3 including all values and ranges there between), an EILV nsP3 (amino acids 1353 to 1808 of SEQ ID NO:3, or any peptide of 5, 10, 15, 20, 30, 40, 50, 60, 70, 80, 90, 100, 200, 300, or 400 consecutive amino acids of SEQ ID NO:3 including all values and ranges there between) or an EILV nsP4 (amino acids 1809 to 2415 of SEQ ID NO:3, or any peptide of 5, 10, 15, 20, 30, 40, 50, 60, 70, 80, 90, 100, 200, 300, 400, or 500 consecutive amino acids of SEQ ID NO:3 including all values and ranges there between). In certain aspects, the isolated and/or purified EILV protein has at least 85, 90, 95, 98, 99, or 100% amino acid sequence identity to all or part of the amino acid sequence of an EILV structural protein including: an EILV C protein (amino acids 1 to 255 of SEQ ID NO:5, or any peptide of 5, 10, 15, 20, 30, 40, 50, 60, 70, 80, 90, 100, or 200 consecutive amino acids of SEQ ID NO:5 including all values and ranges there between), an EILV E2 protein (amino acids 319 to 739 of SEQ ID NO:5, or any peptide of 5, 10, 15, 20, 30, 40, 50, 60, 70, 80, 90, 100, 200, or 300 consecutive amino acids of SEQ ID NO:5 including all values and ranges there between), an EILV E1 protein (amino acids 795 to 1233 of SEQ ID NO:5, or any peptide of 5, 10, 15, 20, 30, 40, 50, 60, 70, 80, 90, 100, 200, or 300 consecutive amino acids of SEQ ID NO:5 including all values and ranges there between), an EILV E3 protein (amino acids 256 to 318 of SEQ ID NO:5, or any peptide of 5, 10, 15, 20, 30, 40, or 50 consecutive amino acids of SEQ ID NO:5 including all values and ranges there between), or an EILV 6K (amino acids 740 to 794 of SEQ ID NO:5, or any peptide of 5, 10, 15, 20, 30, or 40 consecutive amino acids of SEQ ID NO:5 including all values and ranges there between). In certain aspects, an immunogenic composition comprises all or part of 1, 2, 3, 4, 5, 6, 7, 8, or 9 EILV proteins. In a further aspect, an immunogenic composition comprises all or part of one or more EILV structural proteins. In another aspect, an immunogenic composition comprises all or part of one or more EILV non-structural proteins.

Other embodiments are directed to alphaviruses comprising all or part of the EILV nucleic acid sequence of SEQ ID NO: 1. In certain aspects the alphavirus is a recombinant alphavirus. Certain embodiments are directed to an alphavirus having a genome comprising (a) an alphavirus nucleic acid segment that is at least 95% identical to a corresponding segment of SEQ ID NO:1 and (b) a heterologous gene. In certain aspects, the alphavirus is chimeric and comprises certain segments of an EILV alphavirus and other segments from a non-EILV alphavirus. A non-EILV alphavirus includes, but is not limited to Ross River (RRV), chikungunya (CHIKV), Sindbis (SINV) Venezuelan equine encephalitis (VEEV), Eastern equine encephalitis (EEEV) and Western equine encephalitis (WEEV). In certain embodiments the chimeric alphavirus only replicates in an arthropod host. Such chimeric alphaviruses can comprise an EILV nucleic acid with 1, 2, 3, 4, or 5 of the structural gene regions coding for C, E3, E2, 6K, or E1 proteins substituted with a corresponding non-EILV region or segment.

Still further embodiments are directed to immunogenic compositions comprising an EILV nucleic acid, EILV polypeptide, EILV virus, or alphavirus comprising all or part of an EILV nucleic acid or all or part of 1, 2, 3, 4, 5, 6, 7, 8, or 9 EILV proteins. Certain aspects are directed to one or more recombinant EILV nucleic acid, recombinant EILV polypeptide, recombinant EILV virus, or recombinant alphavirus comprising all or part of an recombinant EILV nucleic acid or all or part of 1, 2, 3, 4, 5, 6, 7, 8, or 9 recombinant EILV proteins. Certain embodiments are directed to virus like particle comprising a recombinant nucleic acid described herein.

Pharmaceutical formulations, such as vaccines, of the present invention comprise an immunogenic amount of alphavirus or viral particle comprising alphavirus proteins or antigens, as disclosed herein, in combination with a pharmaceutically acceptable carrier.

Other embodiments are directed to alphaviruses as arthropod expression systems. These expression systems include all or part of the EILV nucleic acid sequence of SEQ ID NO:1 and a heterologous gene, e.g., a toxin, for expression in arthropods, e.g., mosquitoes. For example, the heterologous gene can be a gene (e.g., antisense or short interfering nucleotide) that disrupts replication or hinders transmission of an arthropod-borne infectious disease including, but not limited to, alphavirus infections (e.g., Chikungunya), flavivirus infections (e.g., Dengue), and malaria (*Plasmodium*). See, e.g., Ito et al. "Transgenic anopheline mosquitoes impaired in transmission of a malaria parasite." *Nature* 417: 452-455 (2002); Olson K E et al. "Genetically Engineered Resistance to Dengue-2 Virus Transmission in Mosquitoes." *Science* 272(5263):884-86 (1996). In still other embodiments, the heterologous gene can be toxic to the arthropod (e.g., a bacterial gene such as from *Wolbachia*), thus killing or reducing the longevity of the arthropod. See, e.g., Moreira L et al. "A *Wolbachia* Symbiont in *Aedes aegypti* Limits Infection with Dengue, Chikungunya, and *Plasmodium*." *Cell* 139:1268-78 (2009).

The term "recombinant" refers to an artificial combination of two otherwise separated segments of nucleic acid, e.g., by chemical synthesis or by the manipulation of isolated segments of nucleic acids by genetic engineering techniques.

An "immunogenic amount" is an amount of alphavirus or viral particles comprising alphavirus antigens sufficient to evoke an immune response in a subject administered an immunogenic composition. An amount of from about $10^1$ to about $10^{10}$ plaque forming units (pfu) per dose is believed suitable, depending upon the age and species of the subject being treated. Subjects that can be administered immunogenic amounts of a composition described herein, e.g., EILV virus or host-range restricted EILV-containing alphavirus chimeras, include but are not limited to human, mammal, and other animal subjects (e.g., horse, donkey, mouse, hamster, monkeys), including livestock and laboratory animals. Administration may be by any suitable route, such as intraperitoneal, intravenous, subcutaneous, or intramuscular injection.

The term "alphavirus" has its conventional meaning, and includes the various species of alphaviruses, including the newly identified Eilat virus, as well as Eastern Equine Encephalitis virus (EEE), Venezuelan Equine Encephalitis virus (VEE), Everglades virus, Mucambo virus, Pixuna virus, Western Equine Encephalitis virus (WEE), Sindbis virus, South African Arbovirus No. 86, Semliki Forest virus, Middelburg virus, Chikungunya virus, O'nyong-nyong virus, Ross River virus, Barmah Forest virus, Getah virus, Sagiyama virus, Bebaru virus, Mayaro virus, Una virus, Aura virus, Whataroa virus, Babanki virus, Kyzylagach virus, Highlands J virus, Fort Morgan virus, Ndumu virus, Buggy Creek virus, and the like.

The term "alphavirus replicon" is used to refer to a nucleic acid molecule expressing alphavirus nonstructural protein genes such that it can direct its own replication (amplification).

The term "alphavirus replicon particle" refers to a virion or virion-like structural complex incorporating an alphavirus replicon.

*Alphavirus*-permissive cells are cells that, upon transfection with the viral RNA transcript, are capable of producing viral particles.

The term "expression vector" refers to a nucleic acid that is capable of directing the expression of a sequence(s) or gene(s) of interest. The vector construct can include a 5' sequence capable of initiating transcription of a nucleic acid, e.g., all or part of an alphavirus. Expressed nucleic acid can code for biologically active alphavirus non-structural proteins (e.g., nsP1, nsP2, nsP3, and nsP4), and an alphavirus RNA polymerase recognition sequence. In addition, the vector construct may include a viral junction region. The vector may also include nucleic acid molecule(s) to allow for production of virus, a 5' promoter that is capable of initiating the synthesis of viral RNA in vitro from cDNA, as well as one or more restriction sites, and a polyadenylation sequence. In addition, the constructs may contain selectable markers such as Neo, SV2 Neo, hygromycin, phleomycin, histidinol, and DHFR. Furthermore, the constructs can include plasmid sequences for replication in host cells and other functionalities known in the art. In certain aspects the vector construct is a DNA construct.

"Expression cassette" refers to a recombinantly produced nucleic acid molecule capable of directing the expression of one or more proteins. The expression cassette includes a promoter capable of directing the expression of a target protein(s), and a sequence encoding one or more proteins, e.g., proteins comprising alphavirus structural protein(s) or heterologous nucleic acids in the context of alphavirus. Optionally, the expression cassette may include transcription termination, splice recognition, and polyadenylation addition sites. Promoters include the CMV, MMTV, MoMLV, and adenovirus VA1RNA promoters. In addition, the expression cassette may contain selectable markers such as Neo, SV2 Neo, hygromycin, phleomycin, histidinol, and DHFR.

"Virus-like particle" refers to an infective and/or immunogenic non-virus particle containing viral nucleic acids and/or proteins. In certain aspects, viral envelope proteins are included in a lipid bilayer or a viral nucleic acid is encapsulated within a lipid bilayer.

"Antigen" refers to a molecule containing one or more epitopes (either linear, conformational or both) that will stimulate a host's immune system to make a humoral and/or cellular antigen-specific response. The term is used interchangeably with the term "immunogen." The term "antigen" denotes both subunit antigens (i.e., antigens that are separate and discrete from a whole organism with which the antigen is associated in nature), as well as non-replicative, killed, attenuated, or inactivated bacteria, viruses, fungi, parasites or other microbes.

An "immune response" to an antigen or composition is the development in a subject of a humoral and/or a cellular immune response to an antigen present in the composition of interest. A "humoral immune response" refers to an immune response mediated by antibody molecules, while a "cellular immune response" is one mediated by T-lymphocytes and/or other white blood cells.

A composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular antigen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, for example, Erickson et al., J. Immunol. 151:4189-4199, 1993; Doe et al., Eur. J. Immunol. 24:2369-2376, 1994. Recent methods of measuring cell-mediated immune response include measurement of intracellular cytokines or cytokine secretion by T-cell populations, or by measurement of epitope specific T-cells (e.g., by the tetramer technique) (reviewed by McMichael, A. J. and O'Callaghan, C. A., J. Exp. Med. 187(9):1367-1371, 1998; Mcheyzer-Williams, M. G. et al., Immunol. Rev. 150:5-21, 1996; Lalvani, A. et al., J. Exp. Med. 186:859-865, 1997).

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

FIGS. 2A-2B. (A) Alignment of putative nsP1 conserved sequence element (CSE) within the genus *Alphavirus*. Nucleotides identical to EILV are displayed with dots. (B) Alignment of putative polyprotein cleavage sites within the genus *Alphavirus*. Amino acids identical to EILV are displayed with dots.

FIGS. 3A-3C. (A) Alignments of putative subgenomic promoter (A) and 3' CSE (B) within the genus *Alphavirus*. Nucleotides identical to EILV are displayed with dots. (C) Phylogenetic tree of representative *Alphavirus* species generated from concatenated nonstructural and structural genes nucleotides by using Bayesian method. Mid-point rooted tree is shown with posterior probabilities on major branches.

FIG. 4. Alignments of putative E1 fusion peptide and ribosomal binding site within the genus *Alphavirus*. Amino acids identical to EILV are displayed with dots.

FIGS. 5A-5B. Phylogenetic trees of representative *Alphavirus* species generated from structural (A) and nonstructural (B) gene nucleotides by using Bayesian method. Mid-point rooted trees are shown with posterior probabilities on major branches.

FIGS. 6A-6B. Complement fixation (A) and hemagglutination-inhibition (B) tests with Eilat virus and other alphavirus antigens and hyperimmune mouse ascitic fluids (MIAF).
* Reciprocal of heterologous titer/reciprocal of homologous titer.

FIGS. 12A-12B. Illustrates the infectivity of EILV/SIN structural construct across various host cells. (A) Diagram of an EILV/SIN marker construct. (B) Results of infection of cell lines with a virus comprising the EILV/SIN marker genome, light and fluorescent image.

FIGS. 13A-13B. Illustrates the infectivity of EILV/EEEV structural construct across various host cells. (A) Diagram of an EILV/EEEV marker construct. (B) Results of infection of cell lines with a virus comprising the EILV marker genome, light and fluorescent image.

DESCRIPTION

Figure 1A:
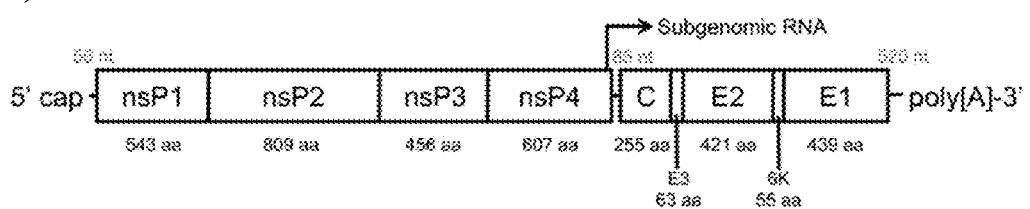
FIGS. 1A-1B. (A) Diagram of the EILV genome. Amino acid size of each protein is provided, as well as the intergenic region, 5' and 3'UTR nucleotide size. (B) Cloning strategy of full-length Eilat virus cDNA clone. Endonuclease sites within EILV sequence, and pRS2 restriction sites and sequence provided.

The genus *Alphavirus* in the family Togaviridae is comprised of small, spherical, enveloped viruses with a genome consisting of single strand, positive-sense RNA approximately 11-12 kb in length (Kuhn R J. Togaviridae: The viruses and their replication, In: Fields B N, Knipe D M, Howley P M, editors. Virology. 5th edition. New York, N.Y.: Lippincott-Raven; Pages 1001-22). The genome contains two open reading frames: the 5' two-thirds of the genome encodes four nonstructural proteins (nsP1, nsP2, nsP3, and nsP4); and the 3' one-third of the genome encodes for structural proteins (Capsid, E2, E1). Alphaviruses enter susceptible cells via receptor-mediated endocytosis and replicate in the cytoplasm of infected cells (id.). Following internalization, low endocytic pH induces a conformational change that exposes E1 fusion peptide and results in the release of the nucleocapsid (id.).

Since the genome of alphaviruses are capped at the 5' end and have a poly A tail at the 3' end, the viral RNA serves as mRNA for translation of nonstructural proteins (id.). The resulting polyprotein is sequentially cleaved into four proteins that are responsible for RNA replication, modification, and proteolytic cleavage (id.). Non-structural proteins facilitate the synthesis of negative and positive strands as well as the transcription of subgenomic mRNA encoding structural proteins (id.). Following translation, E1 and E2 are processed and glycosylated, and E1/E2 heterodimers are inserted into the host plasma membrane (id.). Capsid proteins interact with one genomic RNA copy to form the nucleocapsid, which interacts with the cytoplasmic tail of E2 protein to initiate virion budding from host cell membranes to commence another infectious cycle (id.).

Representative examples of alphaviruses include Aura (ATCC VR-368), Bebaru virus (ATCC VR-600, ATCC VR-1240), Cabassou (ATCC VR-922), Chikungunya virus (ATCC VR-64, ATCC VR-1241), Eastern equine encephalomyelitis virus (ATCC VR-65, ATCC VR-1242), Fort Morgan (ATCC VR-924), Getah virus (ATCC VR-369, ATCC VR-1243), Kyzylagach (ATCC VR-927), Mayaro (ATCC VR-66), Mayaro virus (ATCC VR-1277), Middleburg (ATCC VR-370), Mucambo virus (ATCC VR-580, ATCC VR-1244), Ndumu (ATCC VR-371), Pixuna virus (ATCC VR-372, ATCC VR-1245), Ross River virus (ATCC VR-373, ATCC VR-1246), Semliki Forest (ATCC VR-67, ATCC VR-1247), Sindbis virus (ATCC VR-68, ATCC VR-1248), Tonate (ATCC VR-925), Triniti (ATCC VR-469), Una (ATCC VR-374), Venezuelan equine encephalomyelitis (ATCC VR-69), Venezuelan equine encephalomyelitis virus (ATCC VR-923, ATCC VR-1250 ATCC VR-1249, ATCC VR-532), Western equine encephalomyelitis (ATCC VR-70, ATCC VR-1251, ATCC VR-622, ATCC VR-1252), Whataroa (ATCC VR-926), and Y-62-33 (ATCC VR-375), all of which are incorporated herein by reference.

I. Eilat Virus

Described herein is a new alphavirus, Eilat virus (EILV), isolated from a pool of *Anopheles coustani* mosquitoes collected in the Negev desert of Israel. Phylogenetic analyses places EILV as a sister to the Western Equine Encephalitis (WEE) antigenic complex within the main Glade of mosquito-borne alphaviruses. Electron microscopy revealed that, like other alphaviruses, EILV virions are spherical, roughly 60-70 nm in diameter and bud from the plasma membrane of mosquito cells in culture. EILV readily infects a variety of insect cells with little overt cytopathology. However, in contrast to all other alphaviruses, EILV does not infect various mammalian and avian cell lines at 37° C. Evolutionarily, these findings indicate that EILV lost its ability to infect vertebrate cells. Thus, one use of EILV is in reverse genetic studies to assess the determinants of alphavirus host range. The EILV genome (SEQ ID NO:1) includes a 5' promoter, a non-structural protein (nsPs) coding segment (SEQ ID NO:2), an intergenic region containing a subgenomic promoter (SEQ ID NO:6), a structural protein (sPs) coding region (SEQ ID NO:4), 3' promoter, and a poly-A tail.

In one embodiment, the present invention provides an isolated nucleic acid comprising a coding segment having at least 80, 85, 90, 95, 98, 99, or 100% sequence identity to SEQ ID NO:1 or a fragment thereof. A "fragment" can be any 10, 20, 30, 40, 50, 100, 200, 300, 400, 500, 600, 700, 800, 1000, 2000, 3000, 4000, 5000, 6000, 7000, 8000, 9000, 10000, 11000 consecutive nucleotide segment thereof, including all values and ranges there between.

In some embodiments, the coding segment comprises a non-structural EILV coding region, e.g., SEQ ID NO:2, or a fragment thereof. In some embodiments, the coding segment encodes a non-structural EILV protein, or fragment thereof, e.g., nsP1, nsP2, nsP3, and/or nsP4. In one embodiment, all four of nsP1, nsP2, nsP3, and nsP4 are encoded.

In some embodiments, the coding segment comprises a structural EILV coding region, e.g., SEQ ID NO:4, or a fragment thereof. In some embodiments, the coding segment encodes a structural EILV protein or fragment thereof, e.g., C, E1, E2, E3, and/or 6K. In some embodiments, the coding segment encodes structural EILV protein C, E1, and/or E2.

In one embodiment, the present invention provides a chimera encoding at least one EILV protein or fragment thereof and a heterologous gene. In one embodiment, the chimera encodes at least one structural EILV protein; in another, it encodes at least one non-structural EILV protein. The heterologous gene can be, e.g., a therapeutic protein, an antigen, a toxin, or a marker. An antigen can be, e.g., a structural protein of another virus, e.g., a non-EILV alphavirus, e.g., VEEV, EEEV, or WEEV. In one embodiment, the heterologous gene encodes C, E1, and/or E2 of a non-EILV alphavirus. In one embodiment, the chimera encodes all three of C, E1, and E2 of a non-EILV alphavirus. Alternatively, the antigen can be a non-viral antigen. Such viral and non-viral antigens are useful in the manufacture of immunogenic compositions, and in methods for eliciting immune response in mammals including humans as discussed below.

In another embodiment, the heterologous gene is selected for selective expression in arthropods. Particular genes of interest include those that disrupt replication or hinder transmission of an arthropod-borne infectious disease and/or reduce the lifetime of the arthropod. Particularly useful hosts for such host-selective expression systems include mosquitoes (*Aedes* sp., *Culex* sp., *Anopheles* sp.). In one embodiment, the heterologous gene is expressed in *Aedes* sp., e.g., *Aedes albopictus* or *Aedes aegypti*.

In certain embodiments, the isolated nucleic acid is incorporated into an alphavirus vector capable of replicating in arthropods, e.g., *Aedes* sp., but not in mammals, e.g., humans.

II. Pharmaceutical Compositions

Certain embodiments are directed to pharmaceutical or immunogenic compositions comprising an alphavirus nucleic acid, alphavirus vector, alphavirus particle, alphavirus protein, or alphavirus virus, in combination with a pharmaceutically acceptable carrier, diluent, adjuvant, or recipient.

Briefly, the compositions described herein may be formulated in crude or purified forms. To produce virus in a crude form, virus-producing cells may first be cultivated in a bioreactor, wherein viral particles are released from the cells into the culture media. Virus may then be preserved in crude form by adding a formulation buffer to the culture media containing the virus to form an aqueous suspension. Within certain embodiments, the formulation buffer is an aqueous solution that contains one or more saccharide, high molecular weight structural additive, and buffering component in water. The aqueous solution may also contain one or more amino acids.

The virus or viral particle can be formulated in a purified form. More specifically, before adding the formulation buffer, the crude virus or viral particle described above may be clarified by passing it through a filter and then concentrated, e.g., by a cross flow concentrating system (Filtron Technology Corp., Nortborough, Mass.). DNase can be added to the concentrate to digest exogenous DNA. The digest is then filtered to remove excess media components and to establish the virus or viral particle in a more desirable buffered solution. The filtrate may then be passed over an affinity column, e.g., Sephadex S-500 gel column, and a purified virus or viral particle is eluted. A sufficient amount of formulation buffer is then added to this eluate to reach a desired final concentration of the constituents and to minimally dilute the virus or viral particle. The aqueous suspension may then be stored, e.g., at −70° C., or immediately dried. The formulation buffer may be an aqueous solution that contains one or more saccharide, high molecular weight structural additive, and/or buffering component in water. The aqueous solution may also contain one or more amino acids.

Crude virus or viral particle may also be purified by ion exchange column chromatography. Briefly, crude virus or viral particles may be clarified by passing it through a filter, followed by loading the filtrate onto a column containing a highly sulfonated cellulose matrix. The virus or viral particle may then be eluted from the column in purified form by using a high salt buffer, and the high salt buffer exchanged for a more desirable buffer by passing the eluate over a molecular exclusion column. A sufficient amount of formulation buffer is then added to the purified virus or viral particle and the aqueous suspension is either dried immediately or stored, e.g., at −70° C.

The aqueous suspension in crude or purified form can be dried by lyophilization or evaporation at ambient temperature.

In certain aspects, the aqueous solutions used for formulation are composed of a saccharide, high molecular weight structural additive, a buffering component, and water. The solution may also include one or more amino acids. The components act to preserve the activity of the virus or viral particle upon freezing and lyophilization or drying through evaporation. A saccharide can be lactose, or other saccharides, such as sucrose, mannitol, glucose, trehalose, inositol, fructose, maltose, or galactose. In addition, combinations of saccharides can be used, for example, lactose and mannitol, or sucrose and mannitol.

The high molecular weight structural additive aids in preventing viral aggregation during freezing and provides structural support in the lyophilized or dried state. Within the context of the present invention, structural additives are considered to be of "high molecular weight" if they are greater than 5000 m.w. In certain aspects, a high molecular weight structural additive is human serum albumin. However, other substances may also be used, such as hydroxyethyl-cellulose, hydroxymethyl-cellulose, dextran, cellulose, gelatin, or polyvinylpyrrolidone.

The amino acids, if present, function to further preserve viral or viral particle integrity upon cooling and thawing of the aqueous suspension. A preferred amino acid is arginine, but other amino acids such as lysine, ornithine, serine, glycine, glutamine, asparagine, glutamic acid or aspartic acid can also be used.

The buffering component maintains a relatively constant pH. A variety of buffers may be used, depending on the pH range desired, preferably between 7.0 and 7.8. Suitable buffers include phosphate buffer, citrate buffer, and tromethamine.

In certain aspects, a viral or viral particle formulation can contain a neutral salt to adjust the final formulation to an appropriate iso-osmotic salt concentration. Suitable neutral salts include sodium chloride, potassium chloride or magnesium chloride.

The lyophilized or dehydrated viruses can be reconstituted using a variety of substances, such as water. In certain instances, dilute salt solutions that bring the final formulation to isotonicity may also be used.

III. Examples

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Eilat Virus, a Newly Identified Host Restricted *Alphavirus*

A. Results
Virus Isolation.
EILV was one of 91 viruses collected during a survey of the Negev desert in Israel between 1982-84 (Muriu et al., *Malar J.* 2008, 7:43). Mosquitoes were collected from many parts of the desert including in the city of Eilat and the isolation was from a pool of *Anopheles coustani* (Fornadel et al., *Vector Borne Zoonotic Dis.* 2011, 11(8):1173-9). Preliminary characterization showed that the virus was unable to grow in mammalian cells but could grow to high titers in insect cells.

Figure 1B:
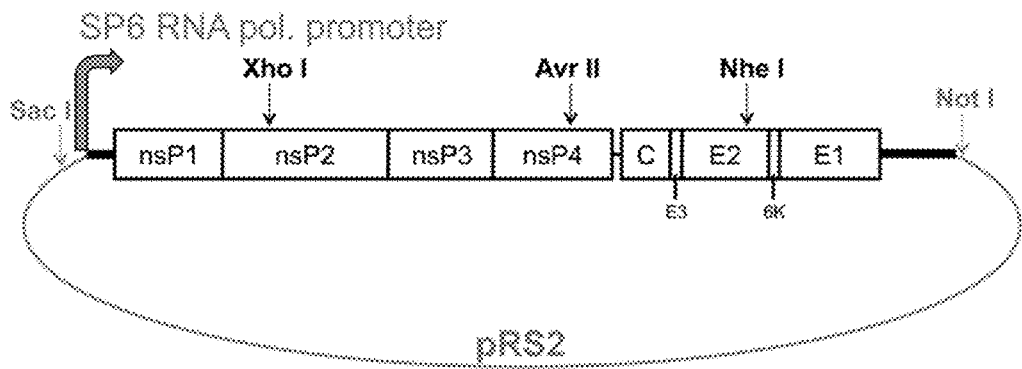

Genomic Analysis.
The sequence of EILV was determined by 454 sequencing. EILV genomic sequence was translated and compared with Sindbis virus to determine the length of each gene product. A schematic of EILV genome is shown in FIG. 1. The length of untranslated regions (UTRs), intergenic region, and each gene product is similar to that of other alphaviruses. The coding region nucleotides and deduced amino acids of EILV were compared with other members within the genus. The nucleotide and amino acid identity of EILV with other members ranged from 57%-43% and 58% to 28%, respectively (Table 1).

TABLE 1

Comparison of nucleotide and amino acid identity of structural and nonstructural coding regions of alphaviruses. Upper diagonal displays percent amino acid identity; lower diagonal contains percent nucleotide identity.

|       | EV | TROV | AURAV | WHATV | SINV | WEEV | EEEV | VEEV | CHIKV |
|-------|----|------|-------|-------|------|------|------|------|-------|
| EV    |    | 52   | 43    | 58    | 44   | 37   | 36   | 37   | 49    |
| TROV  | 53 |      | 43    | 57    | 43   | 38   | 38   | 39   | 51    |
| AURAV | 55 | 57   |       | 47    | 65   | 38   | 39   | 51   | 41    |
| WHATV | 57 | 56   | 61    |       | 55   | 39   | 39   | 39   | 53    |

TABLE 1-continued

Comparison of nucleotide and amino acid identity of structural and nonstructural coding regions of alphaviruses. Upper diagonal displays percent amino acid identity; lower diagonal contains percent nucleotide identity.

| | | | | | | | | | |
|---|---|---|---|---|---|---|---|---|---|
| SINV | 56 | 57 | 61 | 70 | | 39 | 39 | 52 | 40 |
| WEEV | 52 | 54 | 55 | 58 | 57 | | 70 | 46 | 40 |
| EEEV | 51 | 53 | 53 | 54 | 54 | 64 | | 47 | 41 |
| VEEV | 51 | 54 | 54 | 55 | 54 | 58 | 60 | | 41 |
| CHIKV | 52 | 53 | 53 | 55 | 54 | 53 | 54 | 54 | |
| RRV | 51 | 53 | 54 | 55 | 55 | 55 | 55 | 54 | 62 |
| UNAV | 52 | 54 | 54 | 54 | 55 | 53 | 54 | 53 | 62 |
| SFV | 53 | 53 | 54 | 55 | 55 | 54 | 55 | 54 | 62 |
| MIDV | 52 | 53 | 54 | 55 | 54 | 53 | 54 | 54 | 60 |
| BFV | 52 | 52 | 53 | 54 | 53 | 53 | 54 | 53 | 56 |
| NDUV | 51 | 52 | 53 | 54 | 53 | 53 | 53 | 53 | 58 |
| SESV | 50 | 51 | 52 | 52 | 51 | 52 | 52 | 52 | 54 |
| SPDV | 43 | 44 | 44 | 44 | 45 | 44 | 45 | 45 | 45 |

| | RRV | UNAV | SFV | MIDV | BFV | NDUV | SESV | SPDV |
|---|---|---|---|---|---|---|---|---|
| EV | 48 | 39 | 28 | 39 | 38 | 49 | 47 | 28 |
| TROV | 52 | 39 | 28 | 39 | 38 | 51 | 47 | 29 |
| AURAV | 41 | 41 | 30 | 40 | 39 | 41 | 37 | 21 |
| WHATV | 54 | 41 | 31 | 41 | 40 | 53 | 49 | 30 |
| SINV | 41 | 41 | 31 | 41 | 39 | 41 | 37 | 22 |
| WEEV | 40 | 40 | 30 | 40 | 39 | 40 | 38 | 21 |
| EEEV | 41 | 40 | 30 | 40 | 40 | 40 | 38 | 21 |
| VEEV | 40 | 40 | 30 | 40 | 39 | 40 | 38 | 22 |
| CHIKV | 66 | 48 | 36 | 46 | 42 | 58 | 53 | 30 |
| RRV | | 49 | 38 | 47 | 42 | 60 | 53 | 30 |
| UNAV | 64 | | 59 | 46 | 42 | 44 | 39 | 22 |
| SFV | 65 | 66 | | 36 | 33 | 33 | 29 | 29 |
| MIDV | 62 | 61 | 63 | | 59 | 44 | 39 | 22 |
| BFV | 57 | 56 | 58 | 58 | | 42 | 39 | 22 |
| NDUV | 58 | 57 | 59 | 59 | 57 | | 53 | 29 |
| SESV | 54 | 54 | 54 | 54 | 54 | 54 | | 29 |
| SPDV | 46 | 45 | 46 | 45 | 45 | 43 | 43 | |

In both analyses, EILV had the highest identity to Whataroa virus (WHATV) and lowest identity to SPDV. Amino acid comparison of individual protein was also performed (Table 2). EILV polymerase, nsP4, displayed the highest amino acid identity with other alphaviruses, whereas nsP3 had the least. Overall, EILV proteins shared greater identity with Aura (AURAV), WHATV and STNV than other members. The putative cleavage sites for the polyproteins were also compared (FIG. 2B). The nsP4 cleavage site was the most conserved within the genus even amongst the distantly related aquatic alphaviruses, SESV and SPDV. The cleavage sites of EILV non-structural and structural proteins had a greater identity with Trocara (TROV), AURAV, WHATV and STNV.

TABLE 2

Comparison of individual EILV proteins within the genus Alphavirus. Percent amino acid identities are shown.

| Virus | nsP1 | nsP2 | nsP3 | nsP4 | capsid | E3 | E2 | 6k | E1 |
|---|---|---|---|---|---|---|---|---|---|
| Trocara | 64 | 58 | 30 | 72 | 49 | 41 | 34 | 41 | 46 |
| Aura | 73 | 60 | 36 | 74 | 53 | 46 | 36 | 36 | 47 |
| Whataroa | 72 | 65 | 36 | 74 | 50 | 42 | 43 | 40 | 49 |
| Sindbis | 71 | 65 | 34 | 77 | 53 | 45 | 40 | 45 | 50 |
| WEE | 57 | 49 | 29 | 68 | 43 | 44 | 42 | 38 | 49 |
| EEE | 56 | 50 | 29 | 69 | 43 | 42 | 36 | 40 | 47 |
| VEE | 56 | 51 | 29 | 68 | 40 | 47 | 34 | 39 | 45 |
| Chikungunya | 56 | 53 | 34 | 69 | 44 | 43 | 36 | 44 | 42 |
| Ross River | 60 | 52 | 30 | 69 | 41 | 45 | 35 | 25 | 42 |
| Una | 58 | 53 | 32 | 71 | 42 | 45 | 36 | 28 | 43 |
| Semliki Forest | 58 | 53 | 36 | 69 | 42 | 53 | 35 | 28 | 43 |
| Middelburg | 59 | 53 | 37 | 70 | 42 | 46 | 37 | 32 | 42 |
| Barmah Forest | 58 | 52 | 35 | 70 | 45 | 42 | 32 | 34 | 42 |
| Ndumu | 60 | 52 | 32 | 70 | 42 | 50 | 33 | 18 | 42 |

TABLE 2-continued

Comparison of individual EILV proteins within the genus Alphavirus. Percent amino acid identities are shown.

| Virus | nsP1 | nsP2 | nsP3 | nsP4 | capsid | E3 | E2 | 6k | E1 |
|---|---|---|---|---|---|---|---|---|---|
| SES | 53 | 51 | 28 | 65 | 44 | 47 | 30 | 42 | 42 |
| SPD | 41 | 38 | 21 | 52 | 31 | 25 | 24 | 26 | 36 |

Figure 3C:
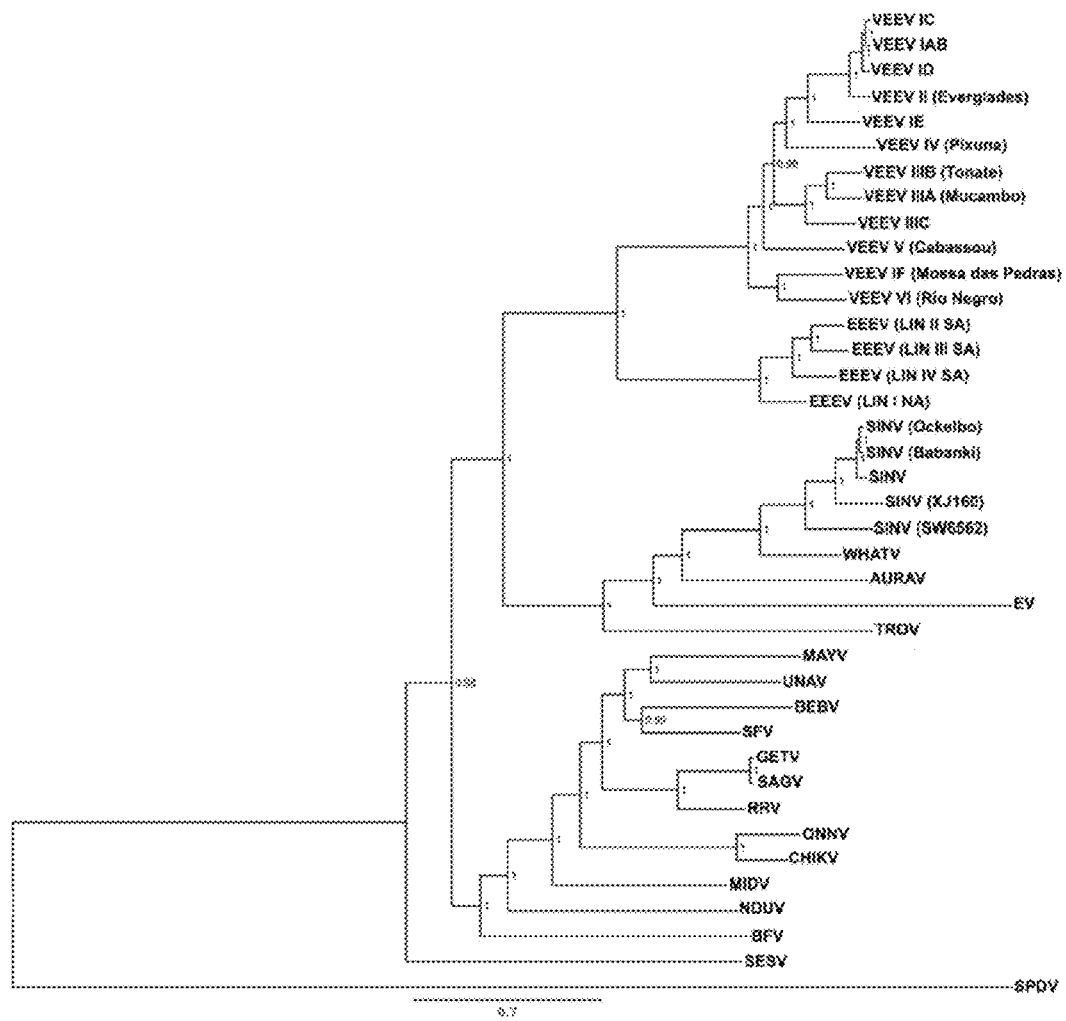

The four conserved sequence elements (CSE) were also compared. First CSE is located in the 5' UTR that serves as a core promoter for RNA synthesis and is structurally conserved. Utilizing mFold EILV 5'UTR could form hairpin structures similar to that of SINV (data not shown). The second CSE is a 51 nt sequence within nsP1 gene which likely functions as a replication enhancer. EILV nsP1 CSE shared identity with AURAV, WHATV and SINV (FIG. 2). Similar to 5' CSE, EILV nsP1 CSE was able to form similar hairpin structures as SINV (data not shown). The third CSE is the 24-nt subgenomic promoter that serves as the promoter for transcription of the subgenomic RNA. EILV subgenomic CSE shared significant identity with WEEV and EEEV (FIG. 3A). Lastly, the 3' CSE is a 19-nt element located immediately before the poly-A tail, which serves as the promoter for negative strand synthesis. EILV 3' CSE was almost identical to AURAV, EEEV, VEEV and SFV (FIG. 3B).

Lastly, the putative E1 fusion peptide and ribosomal binding site in capsid of EILV were also compared. EILV E1 fusion peptide was identical to WHATV and shared significant identity with SINV, WEEV, EEEV, VEEV and CHIKV (FIG. 4). Whereas the ribosomal binding site showed greater sequence divergence, with greater identity with AURAV and SINV (FIG. 4). Many of the amino acid differences in the EILV ribosomal binding site were present in other viruses.

Phylogenetic Analysis.

Figure 5A:
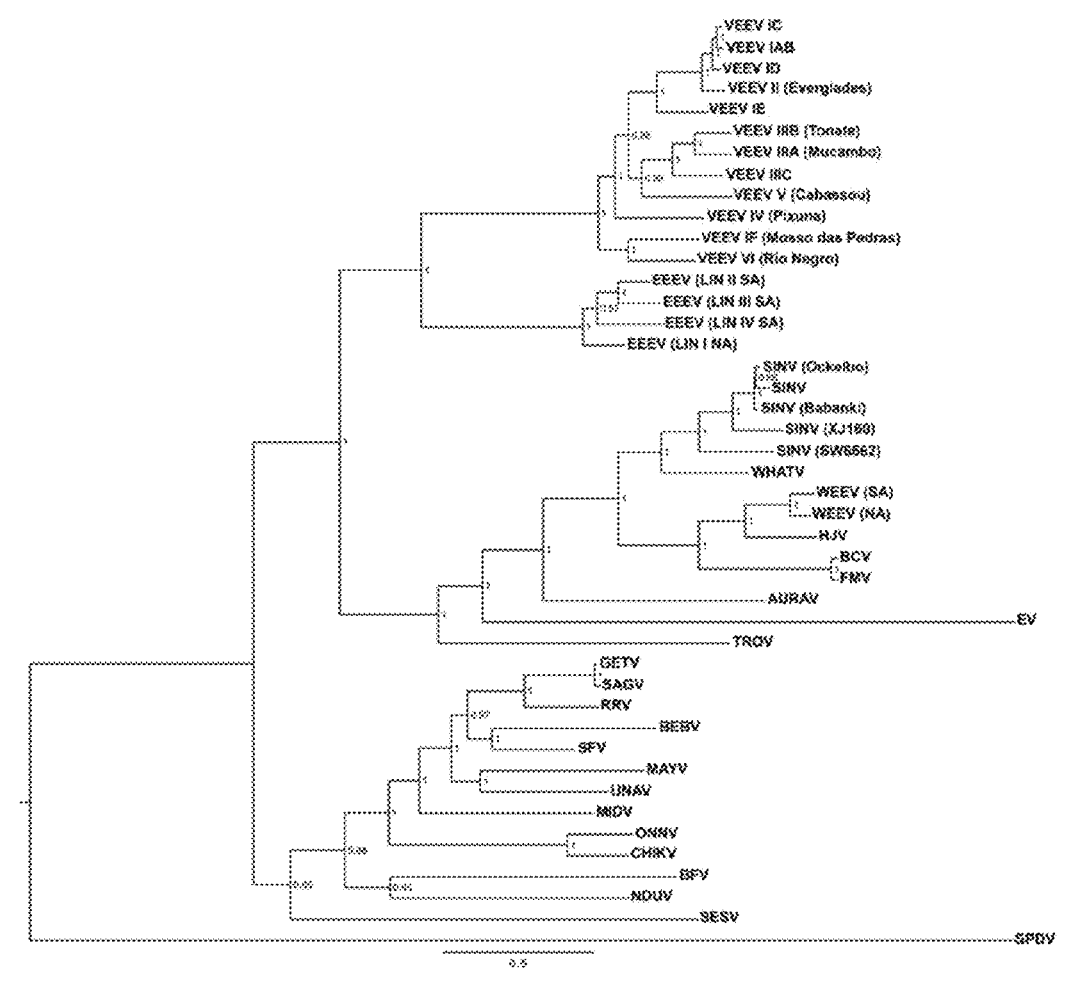
Figure 5B:
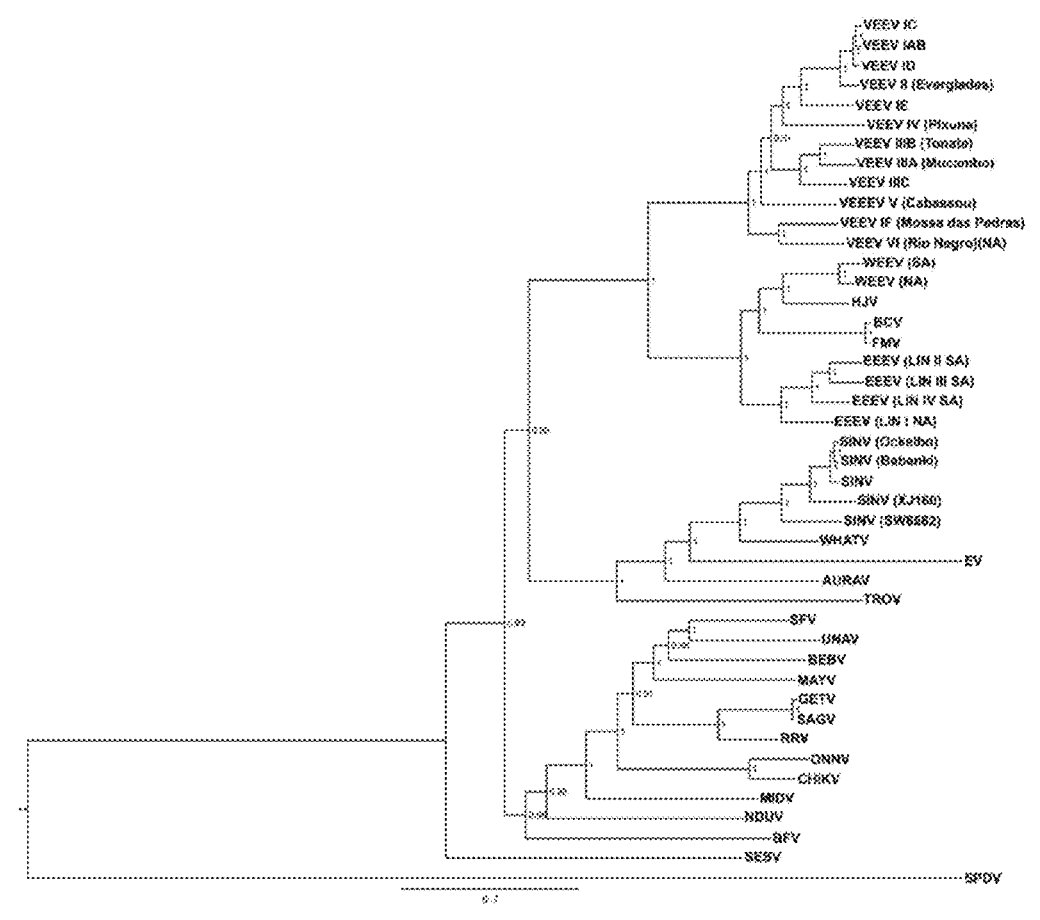

Neighbor joining, maximum likelihood and Bayesian methods were utilized to determine the relationship of EILV within the alphavirus genus. Trees were generated using full-length, non-structural and structural nucleotide alignments. The full-length and structural nucleotide analysis utilizing all three methods placed EILV sister to the WEE complex (FIG. 5A, FIG. 3C, and data not shown) with high posterior and bootstrap support. The analysis of the non-structural alignment showed some inconsistency. The neighbor joining method placed EILV sister to WEE complex where as Bayesian and maximum likelihood analyses placed EILV within the WEE complex basal to WHATV (FIG. 5B, and data not shown).

Serological Analysis.

Both complement fixation (CF) and hemagglutination inhibition (HI) tests were also performed to determine the antigenic relationship of EILV with the genus. In CF test, EILV antigen did not cross react with sera against most members and had minimal cross reactivity with TROV, AURAV, SINV, EEEV, and VEEV (FIG. 6A). In HI test, EILV anti-sera minimally cross-reacted with TROV, SINV, WEEV, and EEEV (FIG. 6B). Purified EILV did not hemagglutinate and EILV anti-sera yielded high background with homologous antigen therefore these data were removed from the analysis.

Rescue of Infectious EILV Clone, In Vitro Characterization and TEM.

Figure 7A:
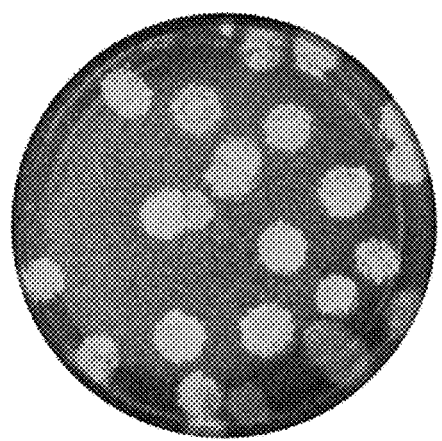
FIGS. 7A-7B. In vitro characterization of Eilat virus. EILV plaque size 3 days post infection on C7/10 cells in a 6-well plate (A). Synthesis of virus-specific RNA in C7/10 cells infected with EILV and SINV, analyzed by agarose gel electrophoresis (B). Lane 1=mock-infected cells, lane 2=SINV, lane 3=EILV.
Figure 7B:
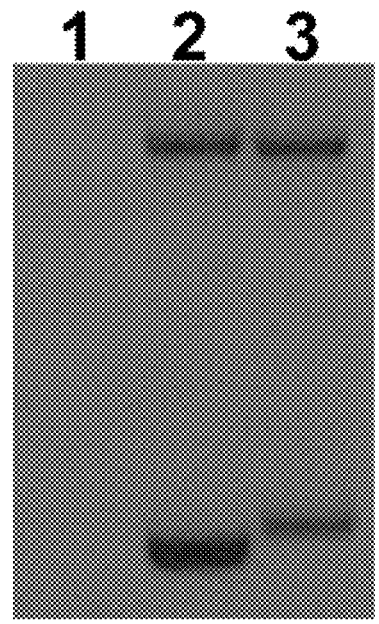
Figures 8A, 8B:
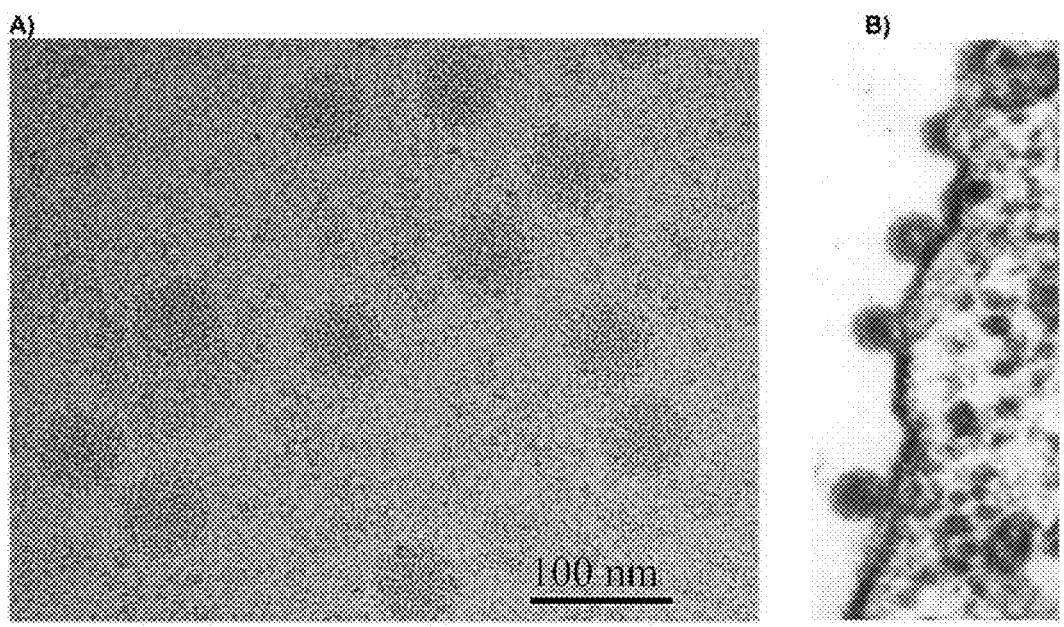
FIGS. 8A-8B. Eilat virus particle morphology by cryo-EM and TEM. EILV virions embedded in vitreous ice (A). Virions budding from the surface of C7/10 cells (B).

EILV cDNA clone was constructed utilizing standard molecular techniques. Virus did not cause any overt cytopathology on C7/10, however at lower cell density EILV infected cells grew at a slower rate (data not shown). EILV formed 3-4 mm plaques 3 days post infection on C7/10 cells (FIG. 7A). RNA analysis of EILV infected C7/10 demonstrated that EILV could produce similar RNA species as SINV, indicating the synthesis of genomic RNA as well as expression of subgenomic RNA (FIG. 7B). TEM analysis of EILV virions showed that the virions are spherical in shape, roughly 60-70 nm in diameter and bud from the plasma membrane (FIGS. 8A-8B).

In Vitro Host Range.

Representative vertebrate (Vero, BHK-21, 293, NIH 3T3, and DEF) and invertebrate (C6/36, C7/10, Cu. tarsalis, and P. papatasi) cell lines were used to determine the in vitro host range of EILV. SINV was used as a positive control as it has been shown to have a broad in vitro host range (Way et al., *J Gen Virol*. 1976, 30(1):123-30; Sarver and Stollar, *Virology*. 1977, 80(2):390-400; Igarashi, *J Gen Virol*. 1978, 40(3):531-44).

Figures 9A, 9B:
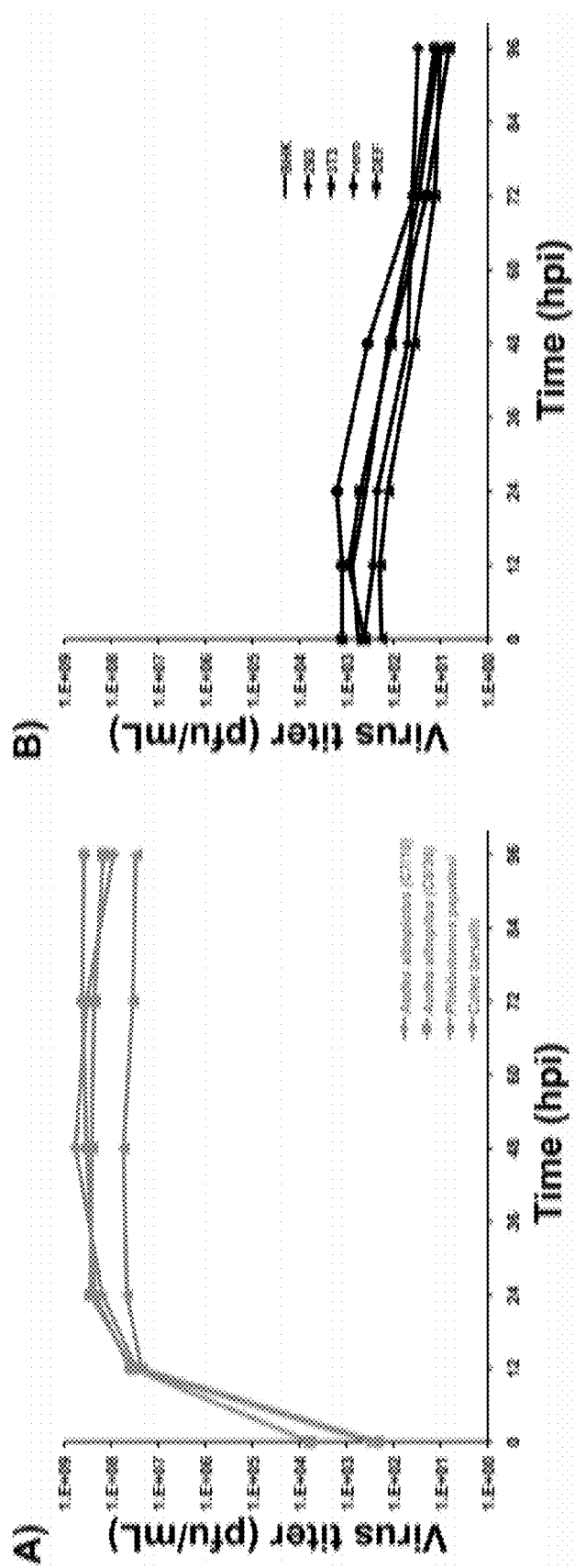
FIGS. 9A-9B. Growth kinetics of Eilat virus on representative invertebrate (A) and vertebrate (B) cell lines. Monolayers were infected at MOI of 10. Supernatants were collected at indicated intervals post-infection and titrated on C7/10 cell monolayers. Each data point represents the average titer of samples taken from triplicate infections.
Figures 10A, 10B, 10C:
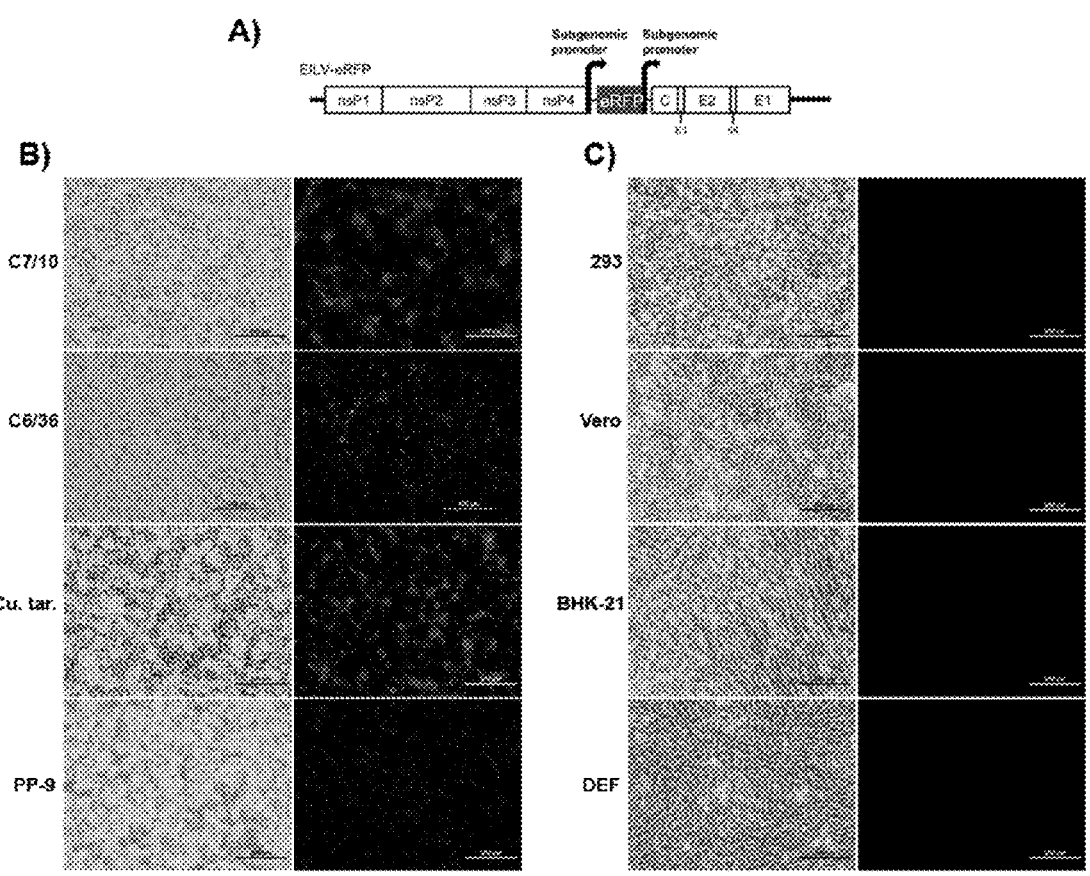
FIGS. 10A-10C. Illustrates the infectivity of EILV across various host cells. (A) Diagram of an EILV marker construct. (B) Results of infection of insect cell lines with a virus comprising the EILV marker genome, light and fluorescent image. (C) Results of infection of vertebrate cell lines with a virus comprising the EILV marker genome, light and fluorescent image.

Both SINV and EILV were able to infect *Cu. tarsalis, P. papatasi*, C6/36, and C7/10 cells (FIG. 9A and data not shown). EILV grew rapidly to high titers (>$10^7$ pfu/mL) 12-hrs-post infection (hpi) with peak titer ranging from $5\times10^7$ to $5\times10^8$ pfu/mL at 48-hpi. Although both SINV and EILV were able to infect all four invertebrate cell lines, the infection did not yield any overt cytopathology (data not shown). All vertebrate cell lines were readily infected by SINV and showed extensive cytopathology at 12-hpi (data not shown). Whereas EILV was unable to infect any of the vertebrate cell lines tested and no overt cytopathology was observed (FIG. 9B and data not shown). The initial EILV inoculum decayed significantly by 72-hpi and was barely above the limit of detection at 96-hpi. These results were also confirmed by infection with EILV-eRFP at MOI of 10 (FIG. 10). EILV infected invertebrate cells expressed eRFP 24-hrs-post-infection, whereas no fluorescent signal was observed in any vertebrate cell lines up to 4-days-post-infection (FIGS. 10B-10C).

Analysis of EILV RNA Replication in Vertebrate Cells.

Figures 11A, 11B:
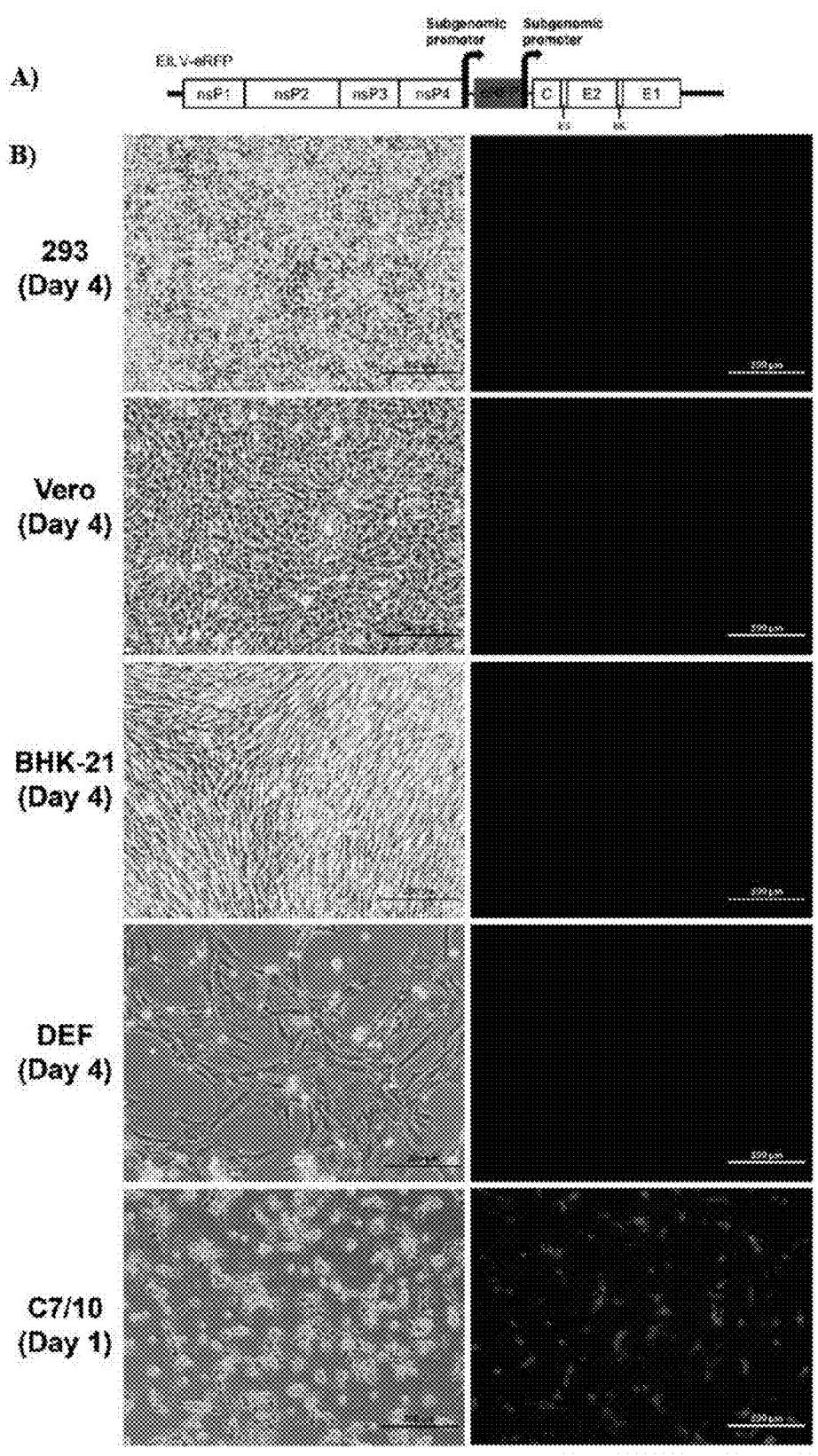
FIGS. 11A-11B. Illustrates results of electroporation of an EILV encoding ribonucleic acid across various host cells. (A) Diagram of an EILV marker construct. (B) Light image and fluorescent image of various cell lines four days post electroporation.

To ascertain whether the host range restriction was present at the RNA levels, EILV-eRFP clone was in vitro transcribed and electroporated into vertebrate and invertebrate cells. EILV-eRFP was unable to replicate in vertebrate cells up to 4 days-post-electroporation, whereas it readily replicated in invertebrate cells (FIGS. 11A-11B). This indicates that the EILV RNA itself in incapable of replication in vertebrate cells.

Chimeric Virus Host Range.

Figures 13A, 13B:
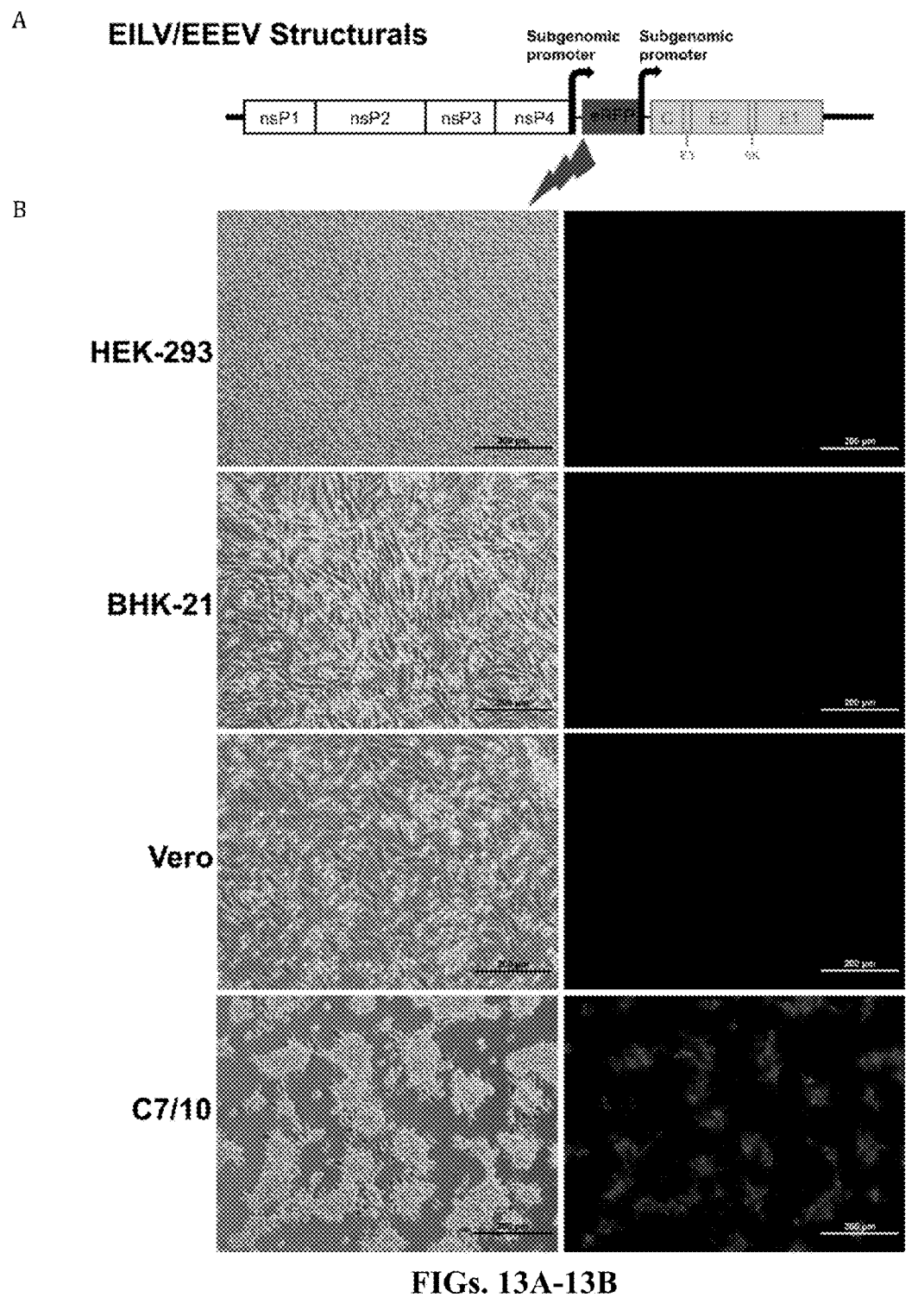

Representative vertebrate and invertebrate cell lines were used to determine the in vitro host range of EILV/SIN and EILV/EEEV chimeras (FIG. 12 and FIG. 13). The chimeras were EILV backbones having the structural proteins substituted with sindbis virus (SIN) or eastern equine encephalitis virus (EEEV) structural protein genes. The chimeric virus maintained the EILV host range, i.e., arthropod specific replication.

B. Materials and Methods:

Viruses and Cells.

Eilat and Sindbis (Eg 339) viruses were obtained from Arbovirus Reference Center at the University of Texas Medical Branch. Both viruses were amplified on C7/10 cells and stored at −80° C.

Vero, baby hamster kidney (BHK-21), human embryonic kidney (HEK-293), Duck embryo fibroblast (DEF), mouse fibroblast (NIH 3T3), and *Aedes albopictus* (C6/36 and C7/10) cell lines were obtained from the American Type Culture Collection. *Culex tarsalis* and *Phlebotomus papatasi* cells were obtained from the Arbovirus Reference Center at the University of Texas Medical Branch. Cell lines were propagated under conditions of 37° C. or 28° C. and 5% $CO_2$ in Dulbecco's modified Eagle's medium containing 10% fetal bovine serum, sodium pyruvate (1 mM), and Penicillin (100 units/mL)-Streptomycin (100 µg/ml). C6/36, C7/10 and *Culex tarsalis* media was additionally supplemented with 1% tryptose phosphate broth solution (Sigma). *Phlebotomus papatasi* cells were maintained in Schneider's media (Sigma) supplemented with 10% fetal bovine serum and Penicillin (100 units/mL)-Streptomycin (100 µg/ml).

Genomic Sequencing.

EILV genome was sequenced by 454 sequencing (Roche Diagnostics Corp.). Briefly, viral RNA was extracted using TRIzol LS (Invitrogen), DNase I (Ambion) treated and cDNA was generated by reverse transcription utilizing Superscript II system (Invitrogen) using random hexamers linked to an arbitrary 17-mer primer sequence. The cDNA was RNase H treated and randomly amplified by PCR with random hexamer linked 17-mer primer. Products were purified (Qiagen) and ligated to specific adapters for sequencing on the 454 Genome Sequencer FLX (454 Life Sciences) without fragmentation. The removal of primer sequences, redundancy filtering, and sequence assembly was performed by utilizing software programs at the GreenePortal website (available on the WorldWideWeb at tako.cpmc.columbia.edu/Tools/). Sequence gaps were filled by using primers based on pyrosequencing in both directions with ABI PRISM Big Dye Terminator 1.1 Cycle Sequencing kits on ABI PRISM 3700 DNA Analyzers (Perkin-Elmer Applied Biosystems). The terminal sequences for each virus were amplified using the Clontech Smarter RACE kit (Clontech). Full-length genome was verified by classical dideoxy sequencing using primers designed from the draft sequence to create products of 1,000 basepairs (bp) with 500 bp overlaps.

Cloning and Rescue of Full-Length Infectious EILV Clone.

EILV cDNA clone was constructed utilizing standard molecular techniques. Briefly, EILV RNA was obtained by infecting C7/10 cells. Viral RNA was isolated from cell culture supernatant using the QIAamp Viral RNA Mini kit (Qiagen). cDNA was produced by using random hexamers and Superscript III (Invitrogen). cDNA fragments were amplified with Phusion DNA polymerase (New England BioLabs) and EILV primers. Amplified PCR products were purified using QIAquick Gel Extraction Kit (Qiagen). Fragments were cloned into pRS2 (FIG. 1B). The full-length cDNA clone was confirmed by ABI PRISM Big Dye sequencing (Applied Biosystems). EILV infectious clone was rescued using standard techniques. EILV cDNA was linearized with Not I and in vitro transcribed using SP6 RNA polymerase transcription kit (Ambion). Approximately 4 μg of RNA was electroporated into C7/10 cells and supernatants were harvested at 48 hrs post-electroporation and stored at −80° C.

Phylogenetic Analysis.

Phylogenetic analysis was performed. *Alphavirus* sequences were downloaded from GenBank, aligned in SeaView utilizing the MUSCLE algorithm (Edgar, 2004, *Nucleic Acids Research*, 32:1792-97; Gouy et al., 2010. *Molecular Biology and Evolution,* 27:221-224). The sequences were aligned by deducing the amino acid sequence from open reading frames (ORFs) aligned and then returned to nucleotide sequences for subsequent analyses. Sequences were aligned as deduced amino acids (aa) from ORFs and then returned to nucleotide sequences for most analyses. The two ORFs were concatenated, and the C-terminus of nsP3 and the N-terminus of the capsid genes were removed from the analysis as these sequences display significant sequences divergence and produce poor alignments. Following manual adjustments, the complete alignment was split into non-structural and structural protein ORFs. Three analyses were performed; neighbor joining (NJ), maximum-likelihood (ML), and Bayesian. NJ analysis was performed utilizing PAUP* version 4.0 (Swofford, 1998, PAUP*: phylogenetic analysis using parsimony (*and other methods), version 4. Sunderland, Mass.: Sinauer Associates). Trees were generated utilizing p-distance algorithm and the robustness of NJ phylogeny was evaluated by bootstrap resampling of 1,000 replicates. ML and Bayesian analyses were performed utilizing the PHYLIP package and Metropolis-coupled Markov Chain Monte Carlo (MCMCMC) in MrBayes v3.1.2, respectively (Felsenstein, 1989, *Cladistics*, 5, 164-166; Ronquist and Huelsenbeck, 2003, *Bioinformatics* 19, 1572-74). Model test in PAUP was used to identify the best-fit nucleotide substitution model, GTR+I+G model (Posada and Crandall, 1998, *Bioinformatics* 14, 817-18). The robustness of ML and Bayesian phylogeny was evaluated by booststrap resampling of 100 and five million generations, respectively.

Serologic Tests.

Complement fixation (CF) and Hemagglutination-inhibition (HI) tests were performed using microtechniques described previously (Beaty et al., 1989, Arboviruses. Schmidt N J, Emmons R W, eds. Diagnostic Procedures for Viral, Rickettsial and Chlamydial Infections, Sixth Edition, Washington D.C.: American Public Health Association, 797-855). CF was performed using two full units of guinea pig complement and titers were recorded as the highest dilutions giving 3 or 4 fixation of complement on a scale of 0 to 4. HI tests were performed using immune sera and acetone-extracted ascitic fluids. Antigens and anti-sera were obtained from the Arbovirus Reference Center at the University of Texas Medical Branch.

Transmission Electron Microscopy.

Thin section and cryo-electron (cryo-EM) microscopy were performed as described previously (Ito and Rikihisa, 1981. Techniques for electron microscopy of rickettsiae. Burgdorfer W, Anacker R L, eds. Rickettsiae and Rickettsial Diseases. New York: Academic Press, 213-27; Travassos da Rosa et al., *Am J Trop Med Hyg.* 2001, 64(1-2):93-7; Sherman and Weaver, *J Virol.,* 2010, 84(19):9775-82). Briefly, monolayers of C7/10 cells infected at MOI of 10, 24 hours-post-infection, cell were fixed in 1.25% formaldehyde, 2.5% glutaraldehyde, 0.03% trinitrophenol and 0.03% $CaCl_2$ in 0.05 M cacodylate buffer pH 7.3, and washed in washed in 0.1 M cacodylate buffer. Cells were scraped, pelleted 1% $OsO_4$ in 0.1 M cacodylate buffer, en bloc stained with 1% uranyl acetate in 0.1 M maleate buffer pH 5.2, dehydrated in ethanol and embedded in Poly/Bed 812 (Polysciences). Ultrathin sections were cut on Reichert Ultracut S ultramicrotome, stained with 2% aqueous uranyl acetate and 0.4% lead citrate, and examined in a Philips 201 electron microscope at 60 kV.

For cryo-EM, virus was amplified on C7/10 cells at MOI of 0.5. 48-hrs-post-infection supernatants were harvested and clarified by centrifugation at 2,000 g for 10 min. Virus was precipitated overnight at 4° C. by adding polyethylene glycol and NaCl to 7% and 2.3% (wt/vol) concentrations, respectively. Virus was pelleted by centrifugation at 4,000 g for 30 min at 4° C. and precipitate was resuspended in TEN buffer (0.05 M Tris-HCl [pH 7.4], 0.1 M NaCl, 0.001 M EDTA). Virus was loaded onto a 20-to-70% continuous sucrose (wt/vol) gradient in TEN buffer and centrifuged at 270,000 g for 1 hr. Following centrifugation, visible virus band was harvested using a Pasteur pipette and centrifuged 4 times through an Amicon Ultra-4 100-kDa-cutoff filter (Millipore) and resuspened in 1 mL of TEN buffer. The purified virus was applied to the holey films (R2×2 Quantifoil; Micro Tools GmbH; or C-flat; Protochips), blotted with filter paper, and plunged into liquid ethane cooled in a liquid nitrogen bath. Frozen grids were stored under liquid nitrogen and transferred to a cryo-specimen 626 holder (Gatan, Inc.) under liquid nitrogen before being loaded into a JEOL 2200FS electron microscope, equipped with an in-column energy filter (omega type) and a field emission gun (FEG) operating at 200 keV.

RNA Analysis.

C7/10 monolayers were infected with SINV or EILV at MOI of 10, 4 hrs-post-infection cells were be labeled with [$^3$H]uridine (20 μCi/ml) in the presence of dactinomycin (ActD) (1 μg/ml) for 3 hrs. Following labeling total cellular RNA was isolated by TRIzol (Invitrogen), denatured with glyoxal in dimethyl sulfoxide and analyzed by agarose gel electrophoresis using previously described conditions (Gorchakov et al., *J Virol.,* 2004 78(1):61-75).

Plaque Assay.

Virus titration was performed on freshly confluent C7/10 cell monolayers in six-well plates. Duplicate wells were infected with 0.1-ml aliquots from serial 10-fold dilutions in growth medium, 0.4 mL of growth media was added to each well to prevent cell desiccation, and virus was adsorbed for 2 hrs. Following incubation, the virus inoculum was removed, and cell monolayers were overlaid with 3 mL of overlay containing 1:1 mixture of 2% tragacanth and 2×MEM with 5% FBS, 2% tryptose phosphate broth solution, 2% Pen-Strep. Cells were incubated at 28° C. in 5% $CO_2$ for 3 days for plaque development, the overlay was removed, and monolayers were fixed with 3 mL of 10% formaldehyde in PBS for 30 mins. Cells were stained with 2% crystal violet in 30% methanol for 5 min at RT and excess stain was removed under running water and plaques will be counted.

One-Step Growth Curves.

Growth curves were performed on representative vertebrate and invertebrate cell lines in triplicates. Three independent dilution curves of EILV and a single dilution of STNV virus stocks were performed to obtain a MOI of 10. Each replicate was used to infect 50% confluent monolayers in 25 cm² flasks. Virus was adsorbed in 1 ml of growth medium for 2 hrs at 37° C. or 29° C. with occasional rocking to prevent cell desiccation. After the inoculum was removed, monolayers were rinsed five times with 12 ml of PBS to remove unbound virus, and 5 ml of growth medium was added to each flask. 0.5-ml aliquot were taken immediately after as a "time hr 0" (T0) sample and replaced with 0.5 ml of fresh medium. Flasks were placed at 37° C. or 28° C. and further samples were taken at 12, 24, 48, 72, and 96 hrs-post-infection. All samples were flash frozen in ethanol-dry ice and stored at −80 C for titration.

Infection with EILV-eRFP Construct.

EILV construct encoding enhanced red fluorescent protein (eRFP) under control of subgenomic promoter was constructed utilizing standard cloning techniques. Representative vertebrate (293-HEK, Vero, BHK-21, DEF, NIH 3T3), and invertebrate cell lines (C6/36, C7/10 *Culex tarsalis* and *Phlebotomus papatasi*) cell lines were infected at an MOI of 10. Light and fluorescent microscopy images were obtained at 24 hour intervals post infection.

Electroporation of EILV-eRFP RNA in Vertebrate Cells.

EILV-eRFP cDNA was linearized with Not I and in vitro transcribed using SP6 RNA polymerase transcription kit (Ambion). ≈4 µg of RNA was electroporated into representative vertebrate (293-HEK, Vero, BHK-21, DEF, NIH 3T3), and invertebrate cell lines (C6/36, C7/10). Light and fluorescent microscopy images were obtained at 24 hour intervals post infection. SINV-eGFP replicon was utilized as positive control.

The invention claimed is:

1. A recombinant alphavirus expression cassette comprising (i) an alphavirus nucleic acid segment having a nucleic acid sequence that is at least 95% identical to the nucleic acid sequence of at least 100 consecutive nucleotides of SEQ ID NO: 1 and (ii) a heterologous nucleic acid segment.

2. The expression cassette of claim 1, wherein the alphavirus nucleic acid segment has a nucleic acid sequence that is the nucleic acid sequence of at least 100 consecutive nucleotides of SEQ ID NO: 1.

3. The expression cassette of claim 1, wherein the expression cassette is comprised in a pRS2 plasmid backbone.

4. A host cell comprising an expression vector of claim 1.

5. The expression cassette of claim 1, wherein the heterologous nucleic acid segment encodes heterologous alphavirus structural proteins.

6. An alphavirus produced by the cell of claim 4.

7. An immunogenic composition comprising the alphavirus of claim 6.

8. A method of stimulating an immune response in a subject comprising administering an effective amount of an immunogenic composition of claim 7.

* * * * *